United States Patent
Grossi De Sa et al.

(10) Patent No.: US 10,975,386 B2
(45) Date of Patent: Apr. 13, 2021

(54) METHOD AND COMPOSITIONS FOR CONTROLLING PEST INSECTS ON PLANTS BY SILENCING GENES OF THE CHITIN SYNTHASE AND OF THE VITELLOGENIN FAMILY, AS WELL AS ALTERNATIVELY BY EXPRESSING THE GENE OF A CRY TOXIN

(71) Applicants: EMBRAPA EMPRESA BRASILEIRA DE PESQUISA AGROPECUÁRIA, Brasília (BR); FUNDAÇÃO UNIVERSIDADE DE BRASÍLIA—FUB—UNB, Brasília (BR)

(72) Inventors: Maria Fátima Grossi De Sa, Brasília (BR); Roberta Ramos Coelho, Brasília (BR); Alexandre Augusto Pereira Fimino, Porto Alegre (BR); Leonardo Lima Pepino De Macedo, Brasília (BR); Maria Cristina Mattar Da Silva, Brasília (BR); Isabela Tristan Lourenço, Brasília (BR); José Dijair Antonino De Souza Júnior, Brasília (BR)

(73) Assignees: EMBRAPA EMPRESA BRASILEIRA DE PESQUISA AGROPECUÁRIA, Brasilia (BR); FUNDAÇÃO UNIVERSIDADE DE BRASÍLIA—FUB—UNB, Brasilia (BR)

( * ) Notice: Subject to any disclaimer, the term of this patent is extended or adjusted under 35 U.S.C. 154(b) by 332 days.

(21) Appl. No.: 15/105,641

(22) PCT Filed: Dec. 18, 2014

(86) PCT No.: PCT/BR2014/050049
§ 371 (c)(1),
(2) Date: Sep. 15, 2016

(87) PCT Pub. No.: WO2015/089616
PCT Pub. Date: Jun. 25, 2015

(65) Prior Publication Data
US 2017/0029843 A1 Feb. 2, 2017

(30) Foreign Application Priority Data

Dec. 18, 2013 (BR) .................... BR102013032649-6

(51) Int. Cl.
*C12N 15/82* (2006.01)
*C12N 15/11* (2006.01)
*C12N 15/113* (2010.01)

(52) U.S. Cl.
CPC ........ *C12N 15/8286* (2013.01); *C12N 15/111* (2013.01); *C12N 15/1137* (2013.01); *C12N 15/8218* (2013.01); *C12N 2330/51* (2013.01); *Y02A 40/146* (2018.01)

(58) Field of Classification Search
CPC .................................. C12N 15/8286
USPC ........................................ 800/285
See application file for complete search history.

(56) References Cited

U.S. PATENT DOCUMENTS

2009/0192117 A1* 7/2009 Herrmann .............. A01N 57/16
514/44 R

OTHER PUBLICATIONS

Trewitt et al. J. Mol. Evol. 34 (6), 478-492 (1992).*
Nakasu et al. 2010 J. of Invertebrate Pathology 104:227-230.*
Thomas et al. 2001, The Plant Journal 25(4):417-425.*

* cited by examiner

*Primary Examiner* — Li Zheng
(74) *Attorney, Agent, or Firm* — Sughrue Mion, PLLC

(57) ABSTRACT

The present invention relates to the control of pest infestation by inhibiting or reducing the expression of genes of the family of chitin synthase and of vitellogenin, as well as through the expression of the toxin Cry8ka5. The invention further provides method and compositions for controlling pests, by feeding the pest with one or more double-stranded RNA molecules provided by the present invention, as well as double-stranded RNA molecule provided by the present invention, as well as through the action of the toxin Cry8ka5 on the target insect. The invention further describes a method of obtaining transgenic plants that express double-stranded RNA molecules and the toxin protein Cry8ka5. The present invention is preferably used for cotton plants.

30 Claims, 4 Drawing Sheets
Specification includes a Sequence Listing.

SEQUENCE LISTING

```
<160> NUMBER OF SEQ ID NOS: 20

<210> SEQ ID NO 1
<211> LENGTH: 185
<212> TYPE: DNA
<213> ORGANISM: Anthonomus grandis

<400> SEQUENCE: 1
aagtagacgc tcacgtatcc agaaggaaaa ccgtggcgga cttggcgaaa aacaaagaca      60
gaaaacgtgc agtcatcaac gacttggatt ccgccttta aagcccgtat ggcaaaaaat     120
acgtaaagga gaagacgcgt ggagtggctt tacctaggaa aactttggca gcaattcaca     180
gaaga                                                                 185

<210> SEQ ID NO 2
<211> LENGTH: 400
<212> TYPE: DNA
<213> ORGANISM: Anthonomus grandis

<400> SEQUENCE: 2
tcatcaaatc tatatggctg gttatgacaa gaatatgtat gttagtatcc cagtcaacgc      60
aaggctcgaa atggatgtga aatctaagga agctaaaatt gaattcgaag ttgaacaaca     120
gcaacaagat tctcgtttag tgcacattac tagcactccc tacacctcaa gaagtgatgt     180
tatggcaatt agtcctgtag ctttgagacc aaacacatat gtaattaagt cccacaggaa     240
caaccacaga tattttgact tcaatttcgg caaaaaagaa actggtttaa cattccgggg     300
atggggacac catcctgaac aaagtatcgg atttaatgat ttagtatcta tgtggcaatc     360
acgcggagtt gctggtgtat gggaacaatt atgggacaaa                           400

<210> SEQ ID NO 3
<211> LENGTH: 185
<212> TYPE: DNA
<213> ORGANISM: Anthonomus grandis

<400> SEQUENCE: 3
tcttctgtga attgctgcca aagtttttcct aggtaaagcc actccacgcg tcttctcctt      60
tacgtatttt ttgccatacg ggctttaaaa ggcggaatcc aagtcgttga tgactgcacg     120
ttttctgtct ttgttttcg ccaagtccgc cacggttttc cttctggata cgtgagcgtc     180
tactt                                                                 185

<210> SEQ ID NO 4
<211> LENGTH: 400
<212> TYPE: DNA
<213> ORGANISM: Anthonomus grandis
```

<400> SEQUENCE: 4

```
tttgtcccat aattgttccc atacaccagc aactccgcgt gattgccaca tagatactaa      60
atcattaaat ccgatacttt gttcaggatg gtgtccccat ccccggaatg ttaaaccagt     120
ttctttttttg ccgaaattga agtcaaaata tctgtggttg ttcctgtggg acttaattac    180
atatgtgttt ggtctcaaag ctacaggact aattgccata acatcacttc ttgaggtgta    240
gggagtgcta gtaatgtgca ctaaacgaga tcttgttgc tgttgttcaa cttcgaattc      300
aattttagct tccttagatt tcacatccat ttcgagcctt gcgttgactg ggatactaac    360
atacatattc ttgtcataac cagccatata gatttgatga                           400
```

<210> SEQ ID NO 5
<211> LENGTH: 1971
<212> TYPE: DNA
<213> ORGANISM: Bacillus thuringiensis

<400> SEQUENCE: 5

```
atggggaggc acttgcttca tctttatctt atgatccttc ctgatacctt gatgagaatg      60
agaccaaata tgcacttca gaacatgaat tataaggatt atttgagaat gtcagaggga      120
tatgacaaca agtactttgc caatcctgag gttttcgcag ctccaggtgg aatcactact    180
ggtattacta tcgttacaaa attgcttggt tggcttggat tgccattcgc tggtgaaacc    240
ggaatggcat tgaattttat tcttggattg ctttggccaa cttctggtaa tccttgggct    300
gaattgatga tattggtgga agaattgatc aatcaaaaga ttgaggagac cgttaggaac    360
aaggcacttg cagatcttgg aaactcagga agagctcttc agtcatatct taacgctttc    420
gaagattggc aaaagaatcc aaatattttc agatcaaaag agcttgttaa ggaaaggttc    480
tctaatgctg aacactcatt gaggactgaa atgtcatcat tcgcaataag aggttttgag   540
attcctctttt tggctacata cgcccaagct gctaatttgc atcttttctt gatcaaggat   600
attcaaatct acgtaagga atggggttac acccaagcag acatcgacct tttctacaga     660
gaacaagttg aatttactaa ggaatataca gagcactgta ttaatatcta taatgatgga    720
ttgaaccagc ttaagggatc aaacgctaag cagtggattg cattcaacag gtttagaagg   780
gaaatgacat tgacagtttt ggacgttgtg gctctttttc ctaactacga cgtgaggatg   840
tatcctatca aaactaccac agagttgacc aggacaatat atactgatcc tttgggttat   900
actaagaccg ttcatcatc tactccacca tggtgcaatt atggatcttc ttttttcatac    960
attgagtcag ttgctattcc tgctccttca ttggtgaaat ggcttttctca aatagaaatc   1020
tactcaaagt ctgctagggc cacacctcaa tctgctgact actgggctgg tcataccatt   1080
acataccatt actcaggtga tgatggacaa gcagttgcta actatggtga caggactaat   1140
ccagtgatag tgaataggta caacttcgaa caggctgata tatacagggt ttcatcatct   1200
gttgcttcat caaccacctc tggagttaag ttgcttacta ctaaggctat atttgatgga   1260
atatcaacta acaacggact tgtttcatac atgtacgaaa acttttcaaa tttttttaat   1320
gagcttaaag acaccatcac tgaacttcct gtgcaaattt cttctcctcc aacatacggt   1380
gacgcagaac agtactctca cagattgtct tatgtgtcta atgctcctac agagtactct   1440
tctggaggac accttattct tggacttata cctgtgcttg gttgaccca tacctcactt    1500
acccaaacca accaaatcca ctcagattct atcacacaaa ttcctgctgt gaaggcaaat   1560
tctgtgtctt cttatgtgac tgttgaaaaa ggtacaggtt ttactggagg agatttggtt   1620
aaattttcta caggtttcat gtctactggt attcaattca atttgaaaat tgaggagggt   1680
```

-continued

```
aaaagataca gaattagaat tagatatgca gccgatgtta atgccactct ttctgcattg    1740
ggtcttaacg atgccttcat taacattgag tctacaatgt cacaggacac tcctcttaaa    1800
tataacgatt ttcagtatgc cgaggccgat aaaacagttc atttgtataa cccaagattc    1860
tcattgtatt tggagaactc tgaccagtct ggtaaatcta tctatattga taggatcgag    1920
ttcatcccag ttgataacgg atctttgaac caccatcatc atcatcatta a             1971
```

<210> SEQ ID NO 6
<211> LENGTH: 652
<212> TYPE: PRT
<213> ORGANISM: Bacillus thuringiensis

<400> SEQUENCE: 6

```
Met Gly Arg His Leu Leu His Leu Tyr Leu Met Ile Leu Pro Asp Thr
1               5                   10                  15

Leu Met Arg Met Arg Pro Asn Asn Ala Leu Gln Asn Met Asn Tyr Lys
            20                  25                  30

Asp Tyr Leu Arg Met Ser Glu Gly Tyr Asp Asn Lys Tyr Phe Ala Asn
        35                  40                  45

Pro Glu Val Phe Ala Ala Pro Gly Gly Ile Thr Thr Gly Ile Thr Ile
    50                  55                  60

Val Thr Lys Leu Leu Gly Trp Leu Gly Leu Pro Phe Ala Gly Glu Thr
65                  70                  75                  80

Gly Met Ala Leu Asn Phe Ile Leu Gly Leu Leu Trp Pro Thr Ser Gly
                85                  90                  95

Asn Pro Trp Ala Glu Leu Met Ile Leu Val Glu Leu Ile Asn Gln
            100                 105                 110

Lys Ile Glu Glu Thr Val Arg Asn Lys Ala Leu Ala Asp Leu Gly Asn
        115                 120                 125

Ser Gly Arg Ala Leu Gln Ser Tyr Leu Asn Ala Phe Glu Asp Trp Gln
    130                 135                 140

Lys Asn Pro Asn Ile Phe Arg Ser Lys Glu Leu Val Lys Glu Arg Phe
145                 150                 155                 160

Ser Asn Ala Glu His Ser Leu Arg Thr Glu Met Ser Ser Phe Ala Ile
                165                 170                 175

Arg Gly Phe Glu Ile Pro Leu Leu Ala Thr Tyr Ala Gln Ala Ala Asn
            180                 185                 190

Leu His Leu Phe Leu Ile Lys Asp Ile Gln Ile Tyr Gly Lys Glu Trp
        195                 200                 205

Gly Tyr Thr Gln Ala Asp Ile Asp Leu Phe Tyr Arg Glu Gln Val Glu
    210                 215                 220

Phe Thr Lys Glu Tyr Thr Glu His Cys Ile Asn Ile Tyr Asn Asp Gly
225                 230                 235                 240

Leu Asn Gln Leu Lys Gly Ser Asn Ala Lys Gln Trp Ile Ala Phe Asn
                245                 250                 255

Arg Phe Arg Arg Glu Met Thr Leu Thr Val Leu Asp Val Val Ala Leu
            260                 265                 270

Phe Pro Asn Tyr Asp Val Arg Met Glu Thr Tyr Pro Ile Lys Thr Thr
        275                 280                 285

Thr Glu Leu Thr Arg Thr Ile Tyr Thr Asp Pro Leu Gly Tyr Thr Lys
    290                 295                 300

Thr Gly Ser Ser Ser Thr Pro Pro Trp Cys Asn Tyr Gly Ser Ser Phe
305                 310                 315                 320
```

```
Ser Tyr Ile Glu Ser Val Ala Ile Pro Ala Pro Ser Leu Val Lys Trp
            325                 330                 335

Leu Ser Gln Ile Glu Ile Tyr Ser Lys Ser Ala Arg Ala Thr Pro Gln
        340                 345                 350

Ser Ala Asp Tyr Trp Ala Gly His Thr Ile Thr Tyr His Tyr Ser Gly
    355                 360                 365

Asp Asp Gly Gln Ala Val Ala Asn Tyr Gly Asp Arg Thr Asn Pro Val
370                 375                 380

Ile Val Asn Arg Tyr Asn Phe Glu Gln Ala Asp Ile Tyr Arg Val Ser
385                 390                 395                 400

Ser Ser Val Ala Ser Ser Thr Thr Ser Gly Val Lys Leu Leu Thr Thr
                405                 410                 415

Lys Ala Ile Phe Asp Gly Ile Ser Thr Asn Asn Gly Leu Val Ser Tyr
            420                 425                 430

Met Tyr Glu Lys Leu Ser Asn Phe Phe Asn Glu Leu Lys Asp Thr Ile
        435                 440                 445

Thr Glu Leu Pro Val Gln Ile Ser Ser Pro Pro Thr Tyr Gly Asp Ala
    450                 455                 460

Glu Gln Tyr Ser His Arg Leu Ser Tyr Val Ser Asn Ala Pro Thr Glu
465                 470                 475                 480

Tyr Ser Ser Gly Gly His Leu Ile Leu Gly Leu Ile Pro Val Leu Gly
                485                 490                 495

Trp Thr His Thr Ser Leu Thr Gln Thr Asn Gln Ile His Ser Asp Ser
            500                 505                 510

Ile Thr Gln Ile Pro Ala Val Lys Ala Asn Ser Val Ser Ser Tyr Val
        515                 520                 525

Thr Val Glu Lys Gly Thr Gly Phe Thr Gly Gly Asp Leu Val Lys Phe
    530                 535                 540

Ser Thr Gly Phe Met Ser Thr Gly Ile Gln Phe Asn Leu Lys Ile Glu
545                 550                 555                 560

Glu Gly Lys Arg Tyr Arg Ile Arg Ile Arg Tyr Ala Ala Asp Val Asn
                565                 570                 575

Ala Thr Leu Ser Ala Leu Gly Leu Asn Asp Ala Phe Ile Asn Ile Glu
            580                 585                 590

Ser Thr Met Ser Gln Asp Thr Pro Leu Lys Tyr Asn Asp Phe Gln Tyr
        595                 600                 605

Ala Glu Ala Asp Lys Thr Val His Leu Tyr Asn Pro Arg Phe Ser Leu
    610                 615                 620

Tyr Leu Glu Asn Ser Asp Gln Ser Gly Lys Ser Ile Tyr Ile Asp Arg
625                 630                 635                 640

Ile Glu Phe Ile Pro Val Asp Asn Gly Ser Leu Asn
                645                 650
```

<210> SEQ ID NO 7
<211> LENGTH: 11346
<212> TYPE: DNA
<213> ORGANISM: Artificial Sequence
<220> FEATURE:
<223> OTHER INFORMATION: Synthetic nucleotide sequence

<400> SEQUENCE: 7

```
ctgacgcgcc ctgtagcggc gcattaagcg cggcgggtgt ggtggttacg cgcagcgtga    60
ccgctacact tgccagcgcc ctagcgcccg ctcctttcgc tttcttccct tcctttctcg   120
ccacgttcgc cggctttccc cgtcaagctc taaatcgggg gctcccttta gggttccgat   180
```

```
ttagtgcttt acggcacctc gacccccaaaa aacttgatta gggtgatggt tcacgtagtg      240
ggccatcgcc ctgatagacg gttttttcgcc ctttgacgtt ggagtccacg ttctttaata      300
gtggactctt gttccaaact ggaacaacac tcaaccctat ctcggtctat tcttttgatt      360
tataagggat tttgccgatt tcggcctatt ggttaaaaaa tgagctgatt taacaaaaat      420
ttaacgcgaa ttttaacaaa atattaacgc ttacaatttg ccattcgcca ttcaggctgc      480
gcaactgttg ggaagggcga tcggtgcggg cctcttcgct attacgccag ctggcgaaag      540
ggggatgtgc tgcaaggcga ttaagttggg taacgccagg gttttcccag tcacgacgtt      600
gtaaaacgac ggccagtgaa ttgtaatacg actcactata gggcgacccg gcgcgccgaa      660
ttcccgggga tccttatgta tttccaactt tcattaacaa tataatcgca tataaatgaa      720
aaatcgtttc caggataata ttttgatgaa atctcatatt attgttcgta ctcggattga      780
tgttgaaggc ttgaagcgct tcaaattata gaccagatta tttaagtttt tcttttgttt      840
actccatatc aatttgatcc attatactac ctaagaaaat ttaggtaaca tagaattatt      900
tattgttata gtaaaaaaaa ggaaaaccac aaaaataatc tacttttacg tatatactat      960
tttcatgaca taagtaatta agttgtacaa cttttttta atgaaaagag agagtaaatt     1020
tatcatgttc atgtgtagtt acctcgtgaa taaccgacgg ttatatagac gcctaacatg     1080
aattgttcag ttgaagacag ttcaaaacat gtgtttcact ctaaaatcct caacaaaaaa     1140
aaagtgttaa aatttgtaaa cctcttttcaa gcaaaaaaag aaaaagtgtt agaatcccaa     1200
gattctttca taatccggaa tcttggctga aaacgtataa agagattga cgtagtaaca     1260
aggagtcttg gtatgcttcc atgcttttta tccttttttg tcatggaacc atgatttggt     1320
taccatttat tatgtaaccg aaattttcat tgtaataatg aatatttaaa ttttttagcaa     1380
aaaaaaacaa aaaaaaacaa ggagtcttgt cttcgttctc aaatttcaga gctcttgcac     1440
ttttcaagag ttttactttg atgagtgaga catttgtctt tttagtgttt attttctaaa     1500
cttaaaatag tagcatcaac atcactcaat tataattctt aagatgttgt agaaaaatat     1560
tttatagatg gaaagtaatc gatattaaga caaataagaa accaaaccgg actttgtgtt     1620
cagaccgaat caaatctgaa ttggagaaat tatggtggag gcgaaagtca acggaactaa     1680
agtataaaac caaatgtcaa aaataaaacc caatttttcat ccttaaacga acctgctgaa     1740
accctaattt cgattaccaa ttccgatcta aaaagaagtc atggaagcca ttgattccgc     1800
aatcgatcct ctcagagatt tcgctaagag cagtgttcgt ctcgtccagc gctgtcacaa     1860
acccgatcgc aagggtaacg ccttttctca aaaaaatctc atttccgatt tttgatctgt     1920
agattagggt tttctgaaat tttgatatca tttgtaattg aattggttat cagaattcac     1980
gaaagtagct gtgcgtacgg cgattggatt tgtggtgatg ggattcgttg gattcttcgt     2040
gaagctcgtt ttcatcccaa tcaacaacat catcgttgga tcttcttagt gtagtacttt     2100
ctttacgagg taattgatct cgcattatat atctacattt tggttatgtt acttgacata     2160
tagtcattga ttcaatagtt ctgttaattc ctttaaagat catttgact agaccacatt     2220
cttggttcat tcctcaataa tttgtaatca tattggtgga tatagaagta gattggttat     2280
agatcagata gtggaagact ttaggatgaa tttcagctag tttttttttt tggcttattg     2340
tctcaaaaga ttagtgcttt gctgtctcca ttgcttctgc tatcgacacg cttctgtctc     2400
cttgtatctt tattatatct attcgtccca tgagttttgt ttgttctgta ttcgttcgct     2460
ctggtgtcat ggatggagtc tctgttccat gtttctgtaa tgcatgttgg gttgtttcat     2520
gcaagaaatg ctgagataaa cactcatttg tgaaagtttc taaactctga atcgcgctac     2580
```

```
aggcaatgct ccgaggagta ggaggagaag aacgaaccaa acgacattat cagcccttg    2640 aggaagctct tagttttgtt attgttttg tagccaaatt ctccattctt attccatttt    2700
cacttatctc ttgttcctta tagaccttat aagtttttta ttcatgtata caaattatat    2760
tgtcatcaag aagtatcttt aaaatctaaa tctcaaatca ccaggactat gttttgtcc     2820 aattcgtgga accaacttgc agcttgtatc cattctctta accaataaaa aagaaagaa     2880 agatcaattt gataaattc tcagccacaa attctacatt taggtttag catatcgaag      2940 gctcaatcac aaatacaata gatagactag agattccagc gtcacgtgag ttttatctat    3000
aaataaagga ccaaaaatca atcccgagg gcattttcgt aatccaacat aaaacccta      3060 aacttcaagt ctcattttta aacaaatcat gttcacaagt ctcttcttct tctctgtttc    3120
tctatctctt gctcatcttt ctcctgaacc atggcggcgg caacaacaac aacaacaaca   3180
tcttcttcga tctccttctc caccaaacca tctccttcct cctccaaatc accattacca   3240
atctccagat tctccctccc attccccta accccaaca aatcatcctc ctcctcccgc     3300
cgccgcggta tcaaatccag ctctcccctcc tccatctccg ccgtgctcaa cacaaccacc  3360
aatgtcacaa ccactccctc tccaaccaaa cctaccaaac ccgaaacatt catctcccga   3420
ttcgctccag atcaaccccg caaaggcgct gatatcctcg tcgaagcttt agaacgtcaa   3480
ggcgtagaaa ccgtattcgc ttaccctgga ggtgcatcaa tggagattca ccaagcctta   3540
acccgctctt cctcaatccg taacgtcctt cctcgtcacg aacaaggagg tgtattcgca   3600
gcagaaggat acgctcgatc ctcaggtaaa ccaggtatct gtatagccac ttcaggtccc   3660
ggagctacaa atctcgttag cggattagcc gatgcgttgt tagatagtgt tcctcttgta   3720
gcaatcacag acaagtccc tcgtcgtatg attggtacag atgcgtttca agagactccg    3780
attgttgagg taacgcgttc gattacgaag cataactatc ttgtgatgga tgttgaagat   3840
atccctagga ttattgagga agctttcttt ttagctactt ctggtagacc tggacctgtt   3900
ttggttgatg ttcctaaaga tattcaacaa cagcttgcga ttcctaattg ggaacaggct   3960
atgagattac ctggttatat gtctaggatg cctaaacctc cggaagattc tcatttggag   4020
cagattgtta ggttgatttc tgagtctaag aagcctgtgt tgtatgttgg tggtggttgt   4080
ttgaattcta gcgatgaatt gggtaggttt gttgagctta cgggtatccc tgttgcgagt   4140
acgttgatgg ggctgggatc ttatccttgt gatgatgagt tgtcgttaca tatgcttgga   4200
atgcatggga ctgtgtatgc aaattacgct gtggagcata tgatttgtt gttggcgttt   4260 ggggtaaggt ttgatgatcg tgtcacgggt aagcttgagg cttttgctag tagggctaag   4320
attgttcata ttgatattga ctcggctgag attgggaaga ataagactcc tcatgtgtct   4380
gtgtgtggtg atgttaagct ggcttttgcaa gggatgaata aggttcttga gaaccgagcg   4440
gaggagctta agcttgattt tggagtttgg aggaatgagt tgaacgtaca gaaacagaag   4500
tttccgttga gctttaagac gtttggggaa gctattcctc cacagtatgc gattaaggtc   4560
cttgatgagt tgactgatgg aaaagccata ataagtactg gtgtcgggca acatcaaatg   4620
tgggcggcgc agttctacaa ttacaagaaa ccaaggcagt ggctatcatc aggaggcctt   4680
ggagctatgg gatttggact tcctgctgcg attggagcgt ctgttgctaa ccctgatgcg   4740
atagttgtgg atattgacgg agatggaagc tttataatga atgtgcaaga gctagccact   4800
attcgtgtag agaatcttcc agtgaaggta cttttattaa acaaccagca tcttggcatg   4860
gttatgcaat gggaagatcg gttctacaaa gctaaccgag ctcacacatt tctcggtgat   4920
```

```
ccggctcagg aggacgagat attcccgaac atgttgctgt ttgcagcagc ttgcgggatt   4980
ccagcggcga gggtgacaaa gaaagcagat ctccgagaag ctattcagac aatgctggat   5040
acaccaggac cttacctgtt ggatgtgatt tgtccgcacc aagaacatgt gttgccgatg   5100
atcccgaatg gtggcacttt caacgatgtc ataacgaaag gagatggccg gattaaatac   5160
tgagagatga aaccggtgat tatcagaacc ttttatggtc tttgtatgca tatggtaaaa   5220
aaacttagtt tgcaatttcc tgtttgtttt ggtaatttga gtttctttta gttgttgatc   5280
tgcctgcttt ttggtttacg tcagactact actgctgttg ttgtttggtt tcctttcttt   5340
catttttataa ataataatc cggttcggtt tactccttgt gactggctca gtttggttat   5400
tgcgaaatgc gaatggtaaa ttgagtaatt gaaattcgtt attagggttc taagctgttt   5460
taacagtcac tgggttaata tctctcgaat cttgcatgga aaatgctctt accattggtt   5520
tttaattgaa atgtgctcat atgggccgtg gtttccaaat taaataaaac tacgatgtca   5580
tcgagaagta aaatcaactg tgtccacatt atcagttttg tgtatacgat gaaatagggt   5640
aattcaaaat ctagcttgat atgccttttg gttcatttta accttctgta aacatttttt   5700
cagattttga acaagtaaat ccaaaaaaaa aaaaaaaaa tctcaactca acactaaatt   5760
attttaatgt ataaaagatg cttaaaacat ttggcttaaa agaagaagc taaaaacata   5820
gagaactctt gtaaattgaa gtatgaaaat atactgaatt gggtattata tgaattttc   5880
tgatttagga ttcacatgat ccaaaaagga aatccagaag cactaatcag acattggaag   5940
taggaatatt tcaaaaagtt ttttttttt aagtaagtga caaaagcttt taaaaaatag   6000
aaaagaaact agtattaaag ttgtaaattt aataaacaaa agaatttttt tatatttttt   6060
catttcttt tccagcatga ggttatgatg gcaggatgtg gatttcattt ttttcctttt   6120
gatagccttt taattgatct attataattg acgaaaaat attagttaat tatagatata   6180
ttttaggtag tattagcaat ttacacttcc aaaagactat gtaagttgta aatatgatgc   6240
gttgatctct tcatcattca atggttagtc aaaaaaataa aagcttaact agtaaactaa   6300
agtagtcaaa aattgtactt tagtttaaaa tattagaata atccaaaacg acatttatgt   6360
gaaacaaaaa caatactcga gagtgaagta gcagagataa tagttattac agtagcagta   6420
ataaaataaa atacatttta ttacaaaaaa acgtacaaga ggtccgcgaa gatagccaat   6480
gagaacgcaa aagacaacc caattctcct atttttttat taaatatttc tagaagaaag   6540
ggtaaattac gccccacggt cacaaaacta ttaataagat catatattta tcactcaact   6600
tccaaaagtt acaaaatgat tattaaacta ttcaaaagtt ttatttcaag tcattggatt   6660
gttaaaatag catttgtatg gatttccctg ttcacattgc ctacatcaat cgaagcctct   6720
cattcccctt ctttttttata gattaagttt ttttttataa aacaatttta aacatcatga   6780
atctctgaac taaaatttaa ataacttttt tcttcgatct ttgacattga ttgttaaatt   6840
aacttgaatc taaggtttgt tctacttgtt gataaataca gatccatcgt gttgatcatt   6900
gaatcgtcac ttggagctca ctcatcggac ttaaaaaaaa aaccttaaca acctagtgac   6960
ttaaataaaa cttttgaata gtttactgac tattttgtaa ctttttaaag ttaagtgact   7020
aaaacgtgaa catactaata gtttagtgac ctcggttgat tttacccaaa aaattattat   7080
tcaacctctc gtcctctcct ttttacacct ttttattatt ttttattttt tctctttact   7140
ttgttttttt agctatttcc agcgactact aaacaaaata aaaattagcc caggacagga   7200
ggatctctca gctactttt ctctcaaaat ttctccaatt agctctgtaa ttttctattt   7260
tgtttctctt tattttagat ttttttggt ccgtgttaat cttcgttgaa ggcgatctag   7320
```

```
ctttgatttg aatttcattt tttttctttt ttccttttaa gatacttttt tgtttgtttt    7380
agggtttagg cgtcatcaaa tctatatggc tggttatgac aagaatatgt atgttagtat    7440
cccagtcaac gcaaggctcg aaatggatgt gaaatctaag gaagctaaaa ttgaattcga    7500
agttgaacaa cagcaacaag attctcgttt agtgcacatt actagcactc cctacacctc    7560
aagaagtgaa agtagacgct cacgtatcca gaaggaaaac cgtggcggac ttggcgaaaa    7620
acaaagacag aaaacgtgca gtcatcaacg acttggattc cgccttttaa agcccgtatg    7680
gcaaaaaata cgtaaaggag aagacgcgtg gagtggcttt acctaggaaa actttggcag    7740
caattcacag aagatctttt ttccttttag tataaaatag ttaagtgatg ttaattagta    7800
tgattataat aatatagttg ttataattgt gaaaaaataa tttataaata tattgtttac    7860
ataaacaaca tagtaatgta aaaaaatatg acaagtgatg tgtaagacga agaagataaa    7920
agttgagagt aagtatatta tttttaatga atttgatcga acatgtaaga tgatatacta    7980
gcattaatat ttgttttaat cataatagta attctagctg gtttgatgaa ttaaatatca    8040
atgataaaat actatagtaa aaataagaat aaataaatta aaataatatt tttttatgat    8100
taatagttta ttatataatt aaatatctat accattacta aatattttag tttaaaagtt    8160
aataaatatt ttgttagaaa ttccaatctg cttgtaattt atcaataaac aaaatattaa    8220
ataacaagct aaagtaacaa ataatatcaa actaatagaa acagtaatct aatgtaacaa    8280
aacataatct aatgctaata taacaaagcg caagatctat cattttatat agtattattt    8340
tcaatcaaca ttcttattaa tttctaaata atacttgtag ttttattaac ttctaaatgg    8400
attgactatt aattaaatga attagtcgaa catgaataaa caaggtaaca tgatagatca    8460
tgtcattgtg ttatcattga tcttacattt ggattgtctt ctgtgaattg ctgccaaagt    8520
tttcctaggt aaagccactc cacgcgtctt ctcctttacg tatttttttgc catacgggct    8580 ttaaaaggcg gaatccaagt cgttgatgac tgcacgtttt ctgtctttgt ttttcgccaa    8640
gtccgccacg gttttccttc tggatacgtg agcgtctact ttcacttctt gaggtgtagg    8700
gagtgctagt aatgtgcact aaacgagaat cttgttgctg ttgttcaact tcgaattcaa    8760
ttttagcttc cttagatttc acatccattt cgagccttgc gttgactggg atactaacat    8820
acatattctt gtcataacca gccatataga tttgatgacg atcgttcaaa catttggcaa    8880
taaagtttct taagattgaa tcctgttgcc ggtcttgcga tgattatcat ataatttctg    8940
ttgaattacg ttaagcatgt aatatttaac atgtaatgca tgacgttatt tatgagatgg    9000
gtttttatga ttagagtccc gcaattatac atttaatacg cgatagaaaa caaaatatcg    9060
cgcgcaaact tggataaatt atcgcgcgcg gtgtcatcta tgaggactag atcggctcga    9120
gggtaccgtc gacctgcagg ggatatcctc gaggttccct ttagtgaggg ttaattgcga    9180
gcttggcgta atcatggtca gctgtttc ctgtgtgaaa ttgttatccg ctcacaattc    9240
cacacaacat acgagccgga agcataaagt gtaaagcctg gggtgcctaa tgagtgagct    9300
aactcacatt aattgcgttg cgctcactgc ccgctttcca gtcgggaaac ctgtcgtgcc    9360
agctgcatta atgaatcggc caacgcgcgg ggagaggcgg tttgcgtatt gggcgctctt    9420
ccgcttcctc gctcactgac tcgctgcgct cggtcgttcg gctgcggcga gcggtatcag    9480
ctcactcaaa ggcggtaata cggttatcca cagaatcagg ggataacgca ggaaagaaca    9540
tgtgagcaaa aggccagcaa aaggccagga accgtaaaaa ggccgcgttg ctggcgtttt    9600
tccataggct ccgccccccct gacgagcatc acaaaaatcg acgctcaagt cagaggtggc    9660
```

-continued

```
gaaacccgac aggactataa agataccagg cgtttccccc tggaagctcc ctcgtgcgct      9720
ctcctgttcc gaccctgccg cttaccggat acctgtccgc ctttctccct tcgggaagcg      9780
tggcgctttc tcatagctca cgctgtaggt atctcagttc ggtgtaggtc gttcgctcca      9840
agctgggctg tgtgcacgaa ccccccgttc agcccgaccg ctgcgcctta tccggtaact      9900
atcgtcttga gtccaacccg gtaagacacg acttatcgcc actggcagca gccactggta      9960
acaggattag cagagcgagg tatgtaggcg gtgctacaga gttcttgaag tggtggccta     10020
actacggcta cactagaaga acagtatttg gtatctgcgc tctgctgaag ccagttacct     10080
tcggaaaaag agttggtagc tcttgatccg gcaaacaaac caccgctggt agcggtggtt     10140 ttttttgtttg caagcagcag attacgcgca gaaaaaaagg atctcaagaa gatcctttga     10200
tcttttctac ggggtctgac gctcagtgga acgaaaactc acgttaaggg attttggtca     10260
tgagattatc aaaaaggatc ttcacctaga tccttttaaa ttaaaaatga agttttaaat     10320
caatctaaag tatatatgag taaacttggt ctgacagtta ccaatgctta atcagtgagg     10380
cacctatctc agcgatctgt ctatttcgtt catccatagt tgcctgactc cccgtcgtgt     10440
agataactac gatacgggag ggcttaccat ctggccccag tgctgcaatg ataccgcgag     10500
acccacgctc accggctcca gatttatcag caataaacca gccagccgga agggccgagc     10560
gcagaagtgg tcctgcaact ttatccgcct ccatccagtc tattaattgt tgccgggaag     10620
ctagagtaag tagttcgcca gttaatagtt tgcgcaacgt tgttgccatt gctacaggca     10680
tcgtggtgtc acgctcgtcg tttggtatgg cttcattcag ctccggttcc caacgatcaa     10740
ggcgagttac atgatccccc atgttgtgca aaaaagcggt tagctccttc ggtcctccga     10800
tcgttgtcag aagtaagttg gccgcagtgt tatcactcat ggttatggca gcactgcata     10860
attctcttac tgtcatgcca tccgtaagat gcttttctgt gactggtgag tactcaacca     10920
agtcattctg agaatagtgt atgcggcgac cgagttgctc ttgcccggcg tcaatacggg     10980
ataataccgc gccacatagc agaactttaa aagtgctcat cattggaaaa cgttcttcgg     11040
ggcgaaaact ctcaaggatc ttaccgctgt tgagatccag ttcgatgtaa cccactcgtg     11100
cacccaactg atcttcagca tcttttactt tcaccagcgt ttctgggtga gcaaaaacag     11160
gaaggcaaaa tgccgcaaaa aagggaataa gggcgacacg gaaatgttga atactcatac     11220
tcttcctttt tcaatattat tgaagcattt atcagggtta ttgtctcatg agcggataca     11280
tatttgaatg tatttagaaa aataaacaaa tagggggttcc gcgcacattt ccccgaaaag     11340
tgccac                                                                11346
```

<210> SEQ ID NO 8
<211> LENGTH: 14364
<212> TYPE: DNA
<213> ORGANISM: Artificial Sequence
<220> FEATURE:
<223> OTHER INFORMATION: Synthetic nucleotide sequence

<400> SEQUENCE: 8

```
ctgacgcgcc ctgtagcggc gcattaagcg cggcgggtgt ggtggttacg cgcagcgtga        60
ccgctacact tgccagcgcc ctagcgcccg ctcctttcgc tttcttcccct tcctttctcg       120 ccacgttcgc cggctttccc cgtcaagctc taaatcgggg gctcccttta gggttccgat       180
ttagtgcttt acggcacctc gaccccaaaa aacttgatta gggtgatggt tcacgtagtg       240
ggccatcgcc ctgatagacg gtttttcgcc ctttgacgtt ggagtccacg ttctttaata       300
gtggactctt gttccaaact ggaacaacac tcaaccctat ctcggtctat tcttttgatt       360
```

```
tataagggat tttgccgatt tcggcctatt ggttaaaaaa tgagctgatt taacaaaaat    420
ttaacgcgaa ttttaacaaa atattaacgc ttacaatttg ccattcgcca ttcaggctgc    480
gcaactgttg ggaagggcga tcggtgcggg cctcttcgct attacgccag ctggcgaaag    540
ggggatgtgc tgcaaggcga ttaagttggg taacgccagg gttttcccag tcacgacgtt    600
gtaaaacgac ggccagtgaa ttgtaatacg actcactata gggcgacccg gcgcgccgaa    660
ttcccgggga tccttatgta tttccaactt cattaacaa tataatcgca tataaatgaa    720
aaatcgtttc caggataata ttttgatgaa atctcatatt attgttcgta ctcggattga    780
tgttgaaggc ttgaagcgct tcaaattata gaccagatta tttaagtttt tcttttgttt    840
actccatatc aatttgatcc attatactac ctaagaaaat ttaggtaaca tagaattatt    900
tattgttata gtaaaaaaaa ggaaaaccac aaaaataatc tacttttacg tatatactat    960
tttcatgaca taagtaatta agttgtacaa cttttttta atgaaaagag agagtaaatt    1020
tatcatgttc atgtgtagtt acctcgtgaa taaccgacgg ttatatagac gcctaacatg    1080
aattgttcag ttgaagacag ttcaaaacat gtgtttcact ctaaaatcct caacaaaaaa    1140
aaagtgttaa aatttgtaaa cctctttcaa gcaaaaaaag aaaaagtgtt agaatcccaa    1200
gattctttca taatccggaa tcttggctga aaacgtataa aagagattga cgtagtaaca    1260
aggagtcttg gtatgcttcc atgctttta tccttttttg tcatggaacc atgatttggt    1320
taccatttat tatgtaaccg aaattttcat tgtaataatg aatatttaaa tttttagcaa    1380
aaaaaaacaa aaaaaaacaa ggagtcttgt cttcgttctc aaatttcaga gctcttgcac    1440
ttttcaagag ttttactttg atgagtgaga catttgtctt tttagtgttt attttctaaa    1500
cttaaaatag tagcatcaac atcactcaat tataattctt aagatgttgt agaaaaatat    1560
tttatagatg gaaagtaatc gatattaaga caaataagaa accaaaccgg actttgtgtt    1620
cagaccgaat caaatctgaa ttggagaaat tatggtggag gcgaaagtca acggaactaa    1680
agtataaaac caaatgtcaa aaataaaacc caattttcat ccttaaacga acctgctgaa    1740
accctaattt cgattaccaa ttccgatcta aaaagaagtc atggaagcca ttgattccgc    1800
aatcgatcct ctcagagatt tcgctaagag cagtgttcgt ctcgtccagc gctgtcacaa    1860
acccgatcgc aagggtaacg ccttttctca aaaaatctc atttccgatt tttgatctgt    1920
agattagggt tttctgaaat tttgatatca tttgtaattg aattggttat cagaattcac    1980
gaaagtagct gtgcgtacgg cgattggatt tgtggtgatg ggattcgttg gattcttcgt    2040
gaagctcgtt ttcatcccaa tcaacaacat catcgttgga tcttcttagt gtagtacttt    2100
ctttacgagg taattgatct cgcattatat atctacattt tggttatgtt acttgacata    2160
tagtcattga ttcaatagtt ctgttaattc ctttaaagat catttgact agaccacatt    2220 cttggttcat tcctcaataa tttgtaatca tattggtgga tatagaagta gattggttat    2280
agatcagata gtgaagact ttaggatgaa tttcagctag ttttttttttt tggcttattg    2340 tctcaaaaga ttagtgcttt gctgtctcca ttgcttctgc tatcgacacg cttctgtctc    2400
cttgtatctt tattatatct attcgtccca tgagttttgt ttgttctgta ttcgttcgct    2460
ctggtgtcat ggatggagtc tctgttccat gtttctgtaa tgcatgttgg gttgtttcat    2520
gcaagaaatg ctgagataaa cactcatttg tgaaagtttc taaactctga atcgcgctac    2580
aggcaatgct ccgaggagta ggaggagaag aacgaaccaa acgacattat cagccctttg    2640
aggaagctct tagttttgtt attgttttg tagccaaatt ctccattctt attccatttt    2700
```

```
cacttatctc ttgttcctta tagaccttat aagttttta ttcatgtata caaattatat    2760
tgtcatcaag aagtatcttt aaaatctaaa tctcaaatca ccaggactat gttttttgtcc   2820 aattcgtgga accaacttgc agcttgtatc cattctctta accaataaaa aaagaaagaa   2880
agatcaattt gataaatttc tcagccacaa attctacatt taggttttag catatcgaag   2940
gctcaatcac aaatacaata gatagactag agattccagc gtcacgtgag ttttatctat   3000
aaataaagga ccaaaaatca aatcccgagg gcattttcgt aatccaacat aaaacccctta 3060 aacttcaagt ctcattttta aacaaatcat gttcacaagt ctcttcttct tctctgtttc    3120
tctatctctt gctcatcttt ctcctgaacc atggcggcgg caacaacaac aacaacaaca  3180
tcttcttcga tctccttctc caccaaacca tctccttcct cctccaaatc accattacca    3240
atctccagat tctccctccc attcccccta acccccaaca aatcatcctc ctcctcccgc    3300
cgccgcggta tcaaatccag ctctccctcc tccatctccg ccgtgctcaa cacaaccacc  3360
aatgtcacaa ccactccctc tccaaccaaa cctaccaaac ccgaaacatt catctcccga    3420
ttcgctccag atcaaccccg caaaggcgct gatatcctcg tcgaagcttt agaacgtcaa    3480
ggcgtagaaa ccgtattcgc ttaccctgga ggtgcatcaa tggagattca ccaagcctta   3540
acccgctctt cctcaatccg taacgtcctt cctcgtcacg aacaaggagg tgtattcgca   3600
gcagaaggat acgctcgatc ctcaggtaaa ccaggtatct gtatagccac ttcaggtccc   3660
ggagctacaa atctcgttag cggattagcc gatgcgttgt tagatagtgt tcctcttgta     3720
gcaatcacag gacaagtccc tcgtcgtatg attggtacag atgcgtttca agagactccg    3780
attgttgagg taacgcgttc gattacgaag cataactatc ttgtgatgga tgttgaagat    3840
atccctagga ttattgagga agcttttcttt ttagctactt ctggtagacc tggacctgtt    3900
ttggttgatg ttcctaaaga tattcaacaa cagcttgcga ttcctaattg gaacaggct    3960 atgagattac ctggttatat gtctaggatg cctaaacctc cggaagattc tcatttggag   4020
cagattgtta ggttgatttc tgagtctaag aagcctgtgt tgtatgttgg tggtggttgt    4080
ttgaattcta gcgatgaatt gggtaggttt gttgagctta cgggtatccc tgttgcgagt    4140
acgttgatgg gctgggatc ttatccttgt gatgatgagt tgtcgttaca tatgcttgga    4200
atgcatggga ctgtgtatgc aaattacgct gtggagcata gtgatttgtt gttggcgttt    4260
ggggtaaggt ttgatgatcg tgtcacgggt aagcttgagg cttttgctag tagggctaag   4320
attgttcata ttgatattga ctcggctgag attgggaaga ataagactcc tcatgtgtct    4380
gtgtgtggtg atgttaagct ggcttttgcaa gggatgaata aggttcttga aaccgagcg   4440 gaggagctta agcttgattt tggagtttgg aggaatgagt tgaacgtaca gaaacagaag   4500
tttccgttga gctttaagac gtttggggaa gctattcctc cacagtatgc gattaaggtc   4560
cttgatgagt tgactgatgg aaaagccata ataagtactg gtgtcgggca acatcaaatg    4620
tgggcggcgc agttctacaa ttacaagaaa ccaaggcagt ggctatcatc aggaggcctt    4680
ggagctatgg gatttggact tcctgctgcg attggagcgt ctgttgctaa ccctgatgcg   4740
atagttgtgg atattgacgg agatggaagc tttataatga atgtgcaaga gctagccact   4800
attcgtgtag agaatcttcc agtgaaggta ctttttattaa acaaccagca tcttggcatg    4860
gttatgcaat gggaagatcg gttctacaaa gctaaccgag ctcacacatt tctcggtgat    4920
ccggctcagg aggacgagat attcccgaac atgttgctgt ttgcagcagc ttgcgggatt    4980
ccagcggcga gggtgacaaa gaaagcagat ctccgagaag ctattcagac aatgctggat   5040
acaccaggac cttacctgtt ggatgtgatt tgtccgcacc aagaacatgt gttgccgatg    5100
```

```
atcccgaatg gtggcacttt caacgatgtc ataacggaag gagatggccg gattaaatac    5160
tgagagatga aaccggtgat tatcagaacc ttttatggtc tttgtatgca tatggtaaaa    5220
aaacttagtt tgcaatttcc tgtttgtttt ggtaatttga gtttctttta gttgttgatc    5280
tgcctgcttt ttggtttacg tcagactact actgctgttg ttgtttggtt tccttttcttt   5340 cattttataa ataaataatc cggttcggtt tactccttgt gactggctca gtttggttat    5400
tgcgaaatgc gaatggtaaa ttgagtaatt gaaattcgtt attagggttc taagctgttt    5460
taacagtcac tgggttaata tctctcgaat cttgcatgga aaatgctctt accattggtt    5520
tttaattgaa atgtgctcat atgggccgtg gtttccaaat aaataaaac tacgatgtca     5580 tcgagaagta aaatcaactg tgtccacatt atcagttttg tgtatacgat gaaatagggt    5640
aattcaaaat ctagcttgat atgccttttg gttcatttta accttctgta acatttttt    5700 cagattttga acaagtaaat ccaaaaaaaa aaaaaaaaa tctcaactca acactaaatt    5760
attttaatgt ataaaagatg cttaaaacat ttggcttaaa agaaagaagc taaaaacata    5820
gagaactctt gtaaattgaa gtatgaaaat atactgaatt gggtattata tgaattttc     5880 tgatttagga ttcacatgat ccaaaaagga aatccagaag cactaatcag acattggaag    5940
taggaatatt tcaaaaagtt ttttttttt aagtaagtga caaaagcttt taaaaaatag    6000
aaaagaaact agtattaaag ttgtaaattt aataaacaaa agaaatttt tatattttt     6060 catttctttt tccagcatga ggttatgatg gcaggatgtg gatttcattt ttttccttt     6120 gatagccttt taattgatct attataattg acgaaaaaat attagttaat tatagatata    6180
ttttaggtag tattagcaat ttacacttcc aaaagactat gtaagttgta aatatgatgc    6240
gttgatctct tcatcattca atggttagtc aaaaaaataa aagcttaact agtaaactaa    6300
agtagtcaaa aattgtactt tagtttaaaa tattagaata atccaaaacg acatttatgt    6360
gaaacaaaaa caatactcga gagtgaagta gcagagataa tagttattac agtagcagta    6420
ataaaataaa atacatttta ttacaaaaaa acgtacaaga ggtccgcgaa gatagccaat    6480
gagaacgcaa aagacaacc caattctcct atttttttat taaatatttc tagaagaaag    6540
ggtaaattac gccccacggt cacaaaacta ttaataagat catatattta tcactcaact    6600
tccaaaagtt acaaaatgat tattaaacta ttcaaaagtt ttatttcaag tcattggatt    6660
gttaaaatag catttgtatg gatttccctg ttcacattgc ctacatcaat cgaagcctct    6720
cattccccct cttttttata gattaagttt ttttttataa aacaattta aacatcatga    6780 atctctgaac taaaatttaa ataacttttt tcttcgatct ttgacattga ttgttaaatt    6840
aacttgaatc taaggtttgt tctacttgtt gataaataca gatccatcgt gttgatcatt    6900
gaatcgtcac ttggagctca ctcatcggac ttaaaaaaaa aaccttaaca acctagtgac    6960
ttaaataaaa cttttgaata gtttactgac tattttgtaa cttttaaag ttaagtgact    7020 aaaacgtgaa catactaata gtttagtgac ctcggttgat tttacccaaa aaattattat    7080
tcaacctctc gtcctctcct ttttacacct ttttattatt ttttatttt tctctttact    7140 ttgttttttt agctatttcc agcgactact aaacaaaata aaaattagcc caggacagga    7200
ggatctctca gctactttt ctctcaaaat ttctccaatt agctctgtaa ttttctattt    7260
tgtttctctt tattttagat ttttttggt ccgtgttaat cttcgttgaa ggcgatctag    7320
ctttgatttg aatttcattt ttttctttt ttccttttaa gatactttt tgtttgtttt    7380 agggtttagg cgtcatcaaa tctatatggc tggttatgac aagaatatgt atgttagtat    7440
```

```
cccagtcaac gcaaggctcg aaatggatgt gaaatctaag gaagctaaaa ttgaattcga    7500
agttgaacaa cagcaacaag attctcgttt agtgcacatt actagcactc cctacacctc    7560
aagaagtgaa agtagacgct cacgtatcca gaaggaaaac cgtggcggac ttggcgaaaa    7620
acaaagacag aaaacgtgca gtcatcaacg acttggattc cgccttttaa agcccgtatg    7680
gcaaaaaata cgtaaaggag aagacgcgtg gagtggcttt acctaggaaa actttggcag    7740
caattcacag aagatctttt ttcctttag tataaaatag ttaagtgatg ttaattagta    7800
tgattataat aatatagttg ttataattgt gaaaaaataa tttataaata tattgtttac    7860
ataaacaaca tagtaatgta aaaaaatatg acaagtgatg tgtaagacga agaagataaa    7920
agttgagagt aagtatatta tttttaatga atttgatcga acatgtaaga tgatatacta    7980
gcattaatat ttgttttaat cataatagta attctagctg gtttgatgaa ttaaatatca    8040
atgataaaat actatagtaa aaataagaat aaataaatta aaataatatt tttttatgat    8100
taatagttta ttatataatt aaatatctat accattacta aatattttag tttaaaagtt    8160
aataaatatt ttgttagaaa ttccaatctg cttgtaattt atcaataaac aaaatattaa    8220
ataacaagct aaagtaacaa ataatatcaa actaatagaa acagtaatct aatgtaacaa    8280
aacataatct aatgctaata taacaaagcg caagatctat cattttatat agtattattt    8340
tcaatcaaca ttcttattaa tttctaaata atacttgtag ttttattaac ttctaaatgg    8400
attgactatt aattaaatga attagtcgaa catgaataaa caaggtaaca tgatagatca    8460
tgtcattgtg ttatcattga tcttacattt ggattgtctt ctgtgaattg ctgccaaagt    8520
tttcctaggt aaagccactc cacgcgtctt ctccttacg tatttttgc catacgggct    8580 ttaaaaggcg gaatccaagt cgttgatgac tgcacgtttt ctgtctttgt ttttcgccaa    8640
gtccgccacg gttttccttc tggatacgtg agcgtctact ttcacttctt gaggtgtagg    8700
gagtgctagt aatgtgcact aaacgagaat cttgttgctg ttgttcaact tcgaattcaa    8760
ttttagcttc cttagatttc acatccattt cgagccttgc gttgactggg atactaacat    8820
acatattctt gtcataacca gccatataga tttgatgacg atcgttcaaa catttggcaa    8880 taaagttttct taagattgaa tcctgttgcc ggtcttgcga tgattatcat ataatttctg    8940
ttgaattacg ttaagcatgt aatatttaac atgtaatgca tgacgttatt tatgagatgg    9000
gtttttatga ttagagtccc gcaattatac atttaatacg cgatagaaaa caaaatatcg    9060
cgcgcaaact tggataaatt atcgcgcgcg gtgtcatcta tgaggactag atcggctcga    9120
gggtacccct atttatagtt gaggttcaag gaccaaacaa taaatagccc attatctcaa    9180
ggacaaaaaa aaaattatcc catgccactt tttcaaagtc aactttaggg tgctaaactt    9240
gcaccacttg gattgtttgc cattaaaatt gtctgccatt aatcataatg ttaacatagg    9300
ttaccattga gtaccgaatg agttcccttta atggcaacat tttaggtact aaaactcgaa    9360
ggttcatcga taccgcttta gcggcagctt tcgggaggtt tttggtgagg aagaaaccgc    9420
agttgccttg atcgtcttcg attcgagtgc agctaccata cgcttcgtcg atcgaaccga    9480
catgggttcg gaccaagtgg ttcagtttca aaatggctcg atgtttaagc cctcttctgt    9540
tctttaaaag caaagaacaa cccctatac gaaaagaat attagggagc atcatggacc    9600
tttctttgcc tacataccaa ttagggctta atgattccga gctcacaaca atggcgaatt    9660
ggttcttata tgtttgaaac aaatggttca caagatcaat ggctataaca ctcgcacgac    9720
aaaaaggaca acacaaagag agatcaaaaa aacccgacac caaggggcat caagtaataa    9780
acagccccca cagcttcaaa ctaagttcct ttctttcttt ttttgacttt ctttcaaggg    9840
```

```
aagaaaggag agaaagattt tatgctttt  ttattataaa ataaataaaa aaacagctgg    9900
ccgccatggg gaggcacttg cttcatcttt atcttatgat ccttcctgat accttgatga    9960
gaatgagacc aaataatgca cttcagaaca tgaattataa ggattatttg agaatgtcag   10020
agggatatga caacaagtac tttgccaatc ctgaggtttt cgcagctcca ggtggaatca   10080
ctactggtat tactatcgtt acaaaattgc ttggttggct tggattgcca ttcgctggtg   10140
aaaccggaat ggcattgaat tttattcttg gattgctttg gccaacttct ggtaatcctt   10200
gggctgaatt gatgatattg gtggaagaat tgatcaatca aaagattgag agaccgttta   10260
ggaacaaggc acttgcagat cttggaaact caggaagagc tcttcagtca tatcttaacg   10320
ctttcgaaga ttggcaaaag aatccaaata ttttcagatc aaaagagctt gttaaggaaa   10380
ggttctctaa tgctgaacac tcattgagga ctgaaatgtc atcattcgca ataagaggtt   10440
ttgagattcc tctttggct  acatacgccc aagctgctaa tttgcatctt ttcttgatca   10500
aggatattca aatctacggt aaggaatggg gttacaccca agcagacatc gacctttct    10560
acagagaaca agttgaattt actaaggaat atacagagca ctgtattaat atctataatg   10620
atggattgaa ccagcttaag ggatcaaacg ctaagcagtg gattgcattc aacaggttta   10680
gaagggaaat gacattgaca gtttggacg  ttgtggctct ttttcctaac tacgacgtga   10740
ggatgtatcc tatcaaaact accacagagt tgaccaggac aatatatact gatcctttgg   10800
gttatactaa gaccggttca tcatctactc caccatggtg caattatgga tcttctttt    10860
catacattga gtcagttgct attcctgctc cttcattggt gaaatggctt tctcaaatag   10920
aaatctactc aaagtctgct agggccacac ctcaatctgc tgactactgg gctggtcata   10980
ccattacata ccattactca ggtgatgatg acaagcagt  tgctaactat ggtgacagga   11040
ctaatccagt gatagtgaat aggtacaact tcgaacaggc tgatatatac agggtttcat   11100
catctgttgc ttcatcaacc acctctggag ttaagttgct tactactaag gctatatttg   11160
atggaatatc aactaacaac ggacttgttt catacatgta cgaaaaactt tcaaattttt   11220
ttaatgagct taaagacacc atcactgaac ttcctgtgca aatttcttct cctccaacat   11280
acggtgacgc agaacagtac tctcacagat tgtcttatgt gtctaatgct cctacagagt   11340
actcttctgg aggacacctt attcttggac ttatacctgt gcttggttgg acccatacct   11400
cacttacccc aaccaaccaa atccactcag attctatcac acaaattcct gctgtgaagg   11460
caaattctgt gtcttcttat gtgactgttg aaaaaggtac aggttttact ggaggagatt   11520
tggttaaatt ttctacaggt ttcatgtcta ctggtattca attcaatttg aaaattgagg   11580
agggtaaaag atacagaatt agaattagat atgcagccga tgttaatgcc actctttctg   11640
cattgggtct taacgatgcc ttcattaaca ttgagtctac aatgtcacag gacactcctc   11700
ttaaatataa cgattttcag tatgccgagg ccgataaaac agttcatttg tataacccaa   11760
gattctcatt gtatttggag aactctgacc agtctggtaa atctatctat attgatagga   11820
tcgagttcat cccagttgat aacggatctt tgaaccacca tcatcatcat cattaacgat   11880
cgttcaaaca tttggcaata agtttcttta agattgaatc ctgttgccgg tcttgcgatg   11940
attatcatat aatttctgtt gaattacgtt aagcatgtaa tatttaacat gtaatgcatg   12000
acgttattta tgagatgggt ttttatgatt agagtcccgc aattatacat ttaatacgcg   12060
atagaaaaca aaatatcgcg cgcaaacttg gataaaattat cgcgcgcggt gtcatctatg   12120
aggactagat cggggtaccg gatccgtcga cctgcagggg atatcctcga ggttccttt    12180
```

```
agtgagggtt aattgcgagc ttggcgtaat catggtcata gctgtttcct gtgtgaaatt   12240
gttatccgct cacaattcca cacaacatac gagccggaag cataaagtgt aaagcctggg   12300
gtgcctaatg agtgagctaa ctcacattaa ttgcgttgcg ctcactgccc gctttccagt   12360
cgggaaacct gtcgtgccag ctgcattaat gaatcggcca acgcgcgggg agaggcggtt   12420
tgcgtattgg gcgctcttcc gcttcctcgc tcactgactc gctgcgctcg tcgttcggc    12480 tgcggcgagc ggtatcagct cactcaaagg cggtaatacg ttatccaca gaatcagggg     12540 ataacgcagg aaagaacatg tgagcaaaag gccagcaaaa ggccaggaac cgtaaaaagg    12600
ccgcgttgct ggcgtttttc cataggctcc gcccccctga cgagcatcac aaaaatcgac    12660
gctcaagtca gaggtggcga aacccgacag gactataaag ataccaggcg tttccccctg    12720
gaagctccct cgtgcgctct cctgttccga ccctgccgct taccggatac ctgtccgcct    12780
ttctcccttc gggaagcgtg gcgctttctc atagctcacg ctgtaggtat ctcagttcgg    12840
tgtaggtcgt tcgctccaag ctgggctgtg tgcacgaacc ccccgttcag cccgaccgct    12900
gcgccttatc cggtaactat cgtcttgagt ccaacccggt aagacacgac ttatcgccac    12960
tggcagcagc cactggtaac aggattagca gagcgaggta tgtaggcggt gctacagagt    13020
tcttgaagtg gtggcctaac tacggctaca ctagaagaac agtatttggt atctgcgctc    13080
tgctgaagcc agttaccttc ggaaaaagag ttggtagctc ttgatccggc aaacaaacca    13140
ccgctggtag cggtggtttt tttgtttgca agcagcagat tacgcgcaga aaaaaggat     13200 ctcaagaaga tcctttgatc ttttctacgg ggtctgacgc tcagtggaac gaaaactcac    13260
gttaagggat tttggtcatg agattatcaa aaaggatctt cacctagatc cttttaaatt    13320
aaaaatgaag ttttaaatca atctaaagta tatatgagta aacttggtct gacagttacc    13380
aatgcttaat cagtgaggca cctatctcag cgatctgtct atttcgttca tccatagttg    13440
cctgactccc cgtcgtgtag ataactacga tacgggaggg cttaccatct ggccccagtg    13500
ctgcaatgat accgcgagac ccacgctcac cggctccaga tttatcagca ataaccagc     13560 cagccggaag ggccgagcgc agaagtggtc ctgcaacttt atccgcctcc atccagtcta    13620
ttaattgttg ccgggaagct agagtaagta gttcgccagt taatagtttg cgcaacgttg    13680
ttgccattgc tacaggcatc gtggtgtcac gctcgtcgtt tggtatggct tcattcagct    13740
ccggttccca acgatcaagg cgagttacat gatcccccat gttgtgcaaa aaagcggtta    13800
gctccttcgg tcctccgatc gttgtcagaa gtaagttggc cgcagtgtta tcactcatgg    13860
ttatggcagc actgcataat tctcttactg tcatgccatc cgtaagatgc ttttctgtga    13920
ctggtgagta ctcaaccaag tcattctgag aatagtgtat gcggcgaccg agttgctctt    13980
gcccggcgtc aatacgggat aataccgcgc cacatagcag aactttaaaa gtgctcatca    14040
ttggaaaacg ttcttcgggg cgaaaactct caaggatctt accgctgttg agatccagtt    14100
cgatgtaacc cactcgtgca cccaactgat cttcagcatc ttttactttc accagcgttt    14160
ctgggtgagc aaaaacagga aggcaaaatg ccgcaaaaaa gggaataagg gcgacacgga    14220
aatgttgaat actcatactc ttccttttc aatattattg aagcatttat cagggttatt     14280
gtctcatgag cggatacata tttgaatgta tttagaaaaa taaacaaata ggggttccgc    14340
gcacatttcc ccgaaaagtg ccac                                          14364

<210> SEQ ID NO 9
<211> LENGTH: 1011
<212> TYPE: DNA
<213> ORGANISM: Gossypium spp.
```

<400> SEQUENCE: 9

```
agtgaagtag cagagataat agttattaca gtagcagtaa taaaataaaa tacattttat      60
tacaaaaaaa cgtacaagag gtccgcgaag atagccaatg agaacgcaag aagcaacccc     120
aattctccta tttttttatt aaatatttct agaagaaagg gtaaattacg ccccacggtc     180
acaaaactat taataagatc atatatttat cactcaactt ccaaaagtta caaaatgatt     240
attaaactat tcaaaagttt tatttcaagt cattggattg ttaaaatagc atttgtatgg     300
atttccctgt tcacattgcc tacatcaatc gaagcctctc attccccttc tttttatag     360
attaagttt tttttataaa acaattttaa acatcatgaa tctctgaact aaaatttaaa     420
taacttttt cttcgatctt tgacattgat tgttaaatta acttgaatct aaggtttgtt     480
ctacttgttg ataaatacag atccatcgtg ttgatcattg aatcgtcact tggagctcac     540
tcatcggact taaaaaaaaa accttaacaa cctagtgact taaataaaac ttttgaatag     600
tttactgact attttgtaac tttttaaagt taagtgacta aaacgtgaac atactaatag     660
tttagtgacc tcggttgatt ttacccaaaa aattattatt caacctctcg tcctctcctt     720
tttacacctt tttattattt tttattttt ctctttactt tgttttttta gctatttcca     780
gcgactacta aacaaaataa aaattagccc aggacaggag gatctctcag ctacttttc     840
tctcaaaatt tctccaatta gctctgtaat tttctatttt gtttctcttt attttagatt     900
tttttggtc cgtgttaatc ttcgttgaag gcgatctagc tttgatttga atttcatttt     960
ttttcttttt ccttttaag atactttttt gtttgtttta gggtttaggc g             1011
```

<210> SEQ ID NO 10
<211> LENGTH: 766
<212> TYPE: DNA
<213> ORGANISM: Gossypium spp.

<400> SEQUENCE: 10

```
cctatttata gttgaggttc aaggaccaaa caataaatag cccattatct caaggacaaa      60
aaaaaaatta tcccatgcca cttttttcaaa gtcaacttta gggtgctaaa cttgcaccac     120
ttggattgtt tgccattaaa attgtctgcc attaatcata atgttaacat aggttaccat     180
tgagtaccga atgagttccc ttaatggcaa cattttaggt actaaaactc gaaggttcat     240
cgataccgct ttagcggcag cttcgggag gttttggtg aggaagaaac cgcagttgcc     300
ttgatcgtct tcgattcgag tgcagctacc atacgcttcg tcgatcgaac cgacatgggt     360
tcggaccaag tggttcagtt tcaaaatggc tcgatgttta agccctcttc tgttctttaa     420
aagcaaagaa caaccccta tacgaaaaag aatattaggg agcatcatgg acctttcttt     480
gcctacatac caattagggc ttaatgattc cgagctcaca acaatggcga attggttctt     540
atatgtttga aacaaatggt tcacaagatc aatggctata acactcgcac gacaaaaagg     600
acaacacaaa gagagatcaa aaaaacccga caccaagggg catcaagtaa taaacagccc     660
ccacagcttc aaactaagtt cctttctttc ttttttgac tttctttcaa gggaagaaag     720
gagagaaaga ttttatgctt ttttattat aaaataaata aaaaaa                     766
```

<210> SEQ ID NO 11
<211> LENGTH: 741
<212> TYPE: DNA
<213> ORGANISM: Artificial Sequence
<220> FEATURE:
<223> OTHER INFORMATION: Synthetic nucleotide sequence -continued

```
<400> SEQUENCE: 11
tcttttttcc ttttagtata aaatagttaa gtgatgttaa ttagtatgat tataataata      60
tagttgttat aattgtgaaa aaataattta taaatatatt gtttacataa acaacatagt     120
aatgtaaaaa aatatgacaa gtgatgtgta agacgaagaa gataaaagtt gagagtaagt     180
atattatttt taatgaattt gatcgaacat gtaagatgat atactagcat taatatttgt     240
tttaatcata atagtaattc tagctggttt gatgaattaa atatcaatga taaaatacta     300
tagtaaaaat aagaataaat aaattaaaat aatattttt tatgattaat agtttattat      360
ataattaaat atctatacca ttactaaata ttttagttta aaagttaata aatatttgt      420 tagaaattcc aatctgcttg taatttatca ataaacaaaa tattaaataa caagctaaag     480
taacaaataa tatcaaacta atagaaacag taatctaatg taacaaaaca taatctaatg     540
ctaatataac aaagcgcaag atctatcatt ttatatagta ttattttcaa tcaacattct     600
tattaatttc taaataatac ttgtagtttt attaacttct aaatggattg actattaatt     660
aaatgaatta gtcgaacatg aataaacaag gtaacatgya gatcatgtca ttgtgttatc     720
attgatctta catttggatt g                                               741

<210> SEQ ID NO 12
<211> LENGTH: 49
<212> TYPE: DNA
<213> ORGANISM: Artificial Sequence
<220> FEATURE:
<223> OTHER INFORMATION: Synthetic nucleotide sequence

<400> SEQUENCE: 12
ggggacaagt ttgtacaaaa aagcaggctg gtcatcaaat ctatatggc                  49

<210> SEQ ID NO 13
<211> LENGTH: 48
<212> TYPE: DNA
<213> ORGANISM: Artificial Sequence
<220> FEATURE:
<223> OTHER INFORMATION: Synthetic nucleotide sequence

<400> SEQUENCE: 13
ggggaccact ttgtacaaga aagctgggtg atttgtccca taattgtt                   48

<210> SEQ ID NO 14
<211> LENGTH: 20
<212> TYPE: DNA
<213> ORGANISM: Artificial Sequence
<220> FEATURE:
<223> OTHER INFORMATION: Synthetic nucleotide sequence

<400> SEQUENCE: 14
tccaagtcgt tgatgactgc                                                  20

<210> SEQ ID NO 15
<211> LENGTH: 28
<212> TYPE: DNA
<213> ORGANISM: Artificial Sequence
<220> FEATURE:
<223> OTHER INFORMATION: Synthetic nucleotide sequence

<400> SEQUENCE: 15
tcatcaaatc tatatggctg gttatgac                                         28

<210> SEQ ID NO 16
<211> LENGTH: 4729
```

```
<212> TYPE: DNA
<213> ORGANISM: Anthonomus grandis

<400> SEQUENCE: 16
gggattttga aatcatactt ggtaatggat attttgttag tatcaaataa aaattaatct      60
tatcgggaaa cacgtcactt cgaatgtcgt cggttgatcg tgtctttctc agttctatga     120
taatatgttt attttatttt taactaacgc acggtaaatc ggacctacga aactgaaaag     180
tgcagtcagt taagtgtttt gtgacccaat ttgtgttcta ccgcacaaat ggacgaggat     240
tttgacgact ttgacgattt tgacgacgag gattctttgt taggatcaac agagaggcag     300
ggcgaagaag tgaaaccatg gaacaccttc aaggtgatcc acaggaaaac ggccagcgga     360
tccacagtcg aaaacaaact ggtggacaat ggagtcaaat ttctcaaaat cgccaccatt     420
tttatcacat ttttggtggt actaggtacg gcagtactat ccaagggatt gattctctta     480
atgacctcac agatcaagaa gaacgtcact aggaattatt gcaataaagg actagatatt     540
tcaaggcagt acatcttctc agttcccgga gttgaaagag ccacctggat atggttttg      600 atgctcgcct actttgttcc tgaatttatg acattcttca ggtcaggacg aattctacta     660
ttcaaaacga gactctatcc aacccttacg gagtttctca gcctattagt aacagaatgt     720
ttaccagcaa taggcagcag tctgctaatt ttctgcgttc taccgaaact cgatgtggtc     780
aaaggagcca tgctcactaa cgcaatgtgt gtgattccag cattaatgtt ggttttacg      840 aaaattggta cgaaaaagat ctcaatagtc actgaaattg cggatatttt agcattgcta     900
gcgcagctat cagcgatgct cgcttggcca ctaataaatc acgacgaacc tatactgtgg     960
cttataccaa tttgtgccat tttaatctcg tttggttggt gggagaactt tgttccgtta    1020
tcatcaccaa taaaattggt acgacaattg gccaaatcca gaaaagagtt tcccacccgc    1080
aagtactttt gctactttat tatttcatcg gttaaatgta taattttctt cgcgaccact    1140
atagcttgca tatatttaa agatggcgat gtgaactttt tattcgagaa ctttttccgat    1200 atttttctgga atcatccgat gaccgttacc gaggttgttc cacaagtgac aggtaccaac    1260
atcaccgtag atgacgcaat cagcactggg atagtccaca taatctacag cgatatcaat    1320
cttcaggcag ccatttgggg cgtcagcgtc gtttccgctt atgcttgcta cgcctttggc    1380
aagtttgctt gcaaaattat gatccagggt tcaagttttg cttttccgat cgctttaact    1440 gtgccttttcc tcatatcagc tctggtgatc ttttgtggat tctatgccaa agacgtgtgt    1500
gccttctatg acttcttacc ggcatatctc ttctttaact caccacccct tgcttaacctc    1560 ttgaacttcg tggagactca acatccgtat ttatggctgt tttggctgct ttcccaaata    1620
tggatcacca ggcatatttg gaccaacaat aactcgaagc tggcttccac tgaaaagttg    1680
ttcatgcgtc ccatgtacga cgggatcctg atcgatcaat ccattgcaat gaatcgcaga    1740
aatgtcgtgg ataaacttgt agaggaggag aaactggcag acggattgga agcaagaat     1800 atcattgacg agaataaaat aacaagaatc tacgcttgcg ctaccatgtg gcacgagact    1860
ccggaggaaa tgatggagtt cttcaagtct attttcagga tggacgagga ccaagcttgc    1920
taccggattt ctaggcagta cttacagtac cccggcgaag ggtattatga gtgggaaaca    1980
cacatctttt ttgatgatgc ctatttgaga aaatcagtaa acgacaacga tccaatgcta    2040
aactcctacg tgaacgattt tattgcaacc atgcccaaag ccgcagaaga agtgcataag    2100
acaacagtaa aaattcgacc tcctacaata tatcccactc cttacggggg cagactaata    2160
tgggtcctac caggaagaac aaaactcatc gtacatttaa aagacaaggc taagattagg    2220
```

```
gctaaaaaga gatggtctca agtgatgtac atgtattacc tgttaggaca caagttaatg    2280
gataatgaag aaatggatga taaaaaggtt aagctaagat catttaacac gtacatcctg    2340
gccctcgacg gagacatcga tttccaaccg gaagcagtcg ctttactagt ccagtatatg    2400
caaaaaaaga gcaacttagg agctgcttgt gggcgtattc atcctgtagg ttctggaatt    2460
atggcctggt atcaaacgtt cgaatacgca gtgggccatt ggatgcaaaa agcgaccgaa    2520
cacgtcatag gttgcgttct ttgttcgcca ggttgtttct ctctctttag agctagtgcc    2580
cttatggacc acaatgtaat ggctagatat acgacgcgtt cttccgaggc taggcattat    2640
gtacaatatg atcagggcga agatagatgg ctctgcaccc tcctactgca aggggttac     2700
agagtggaat attctgctgc ctccgatgcc tatactcact gtccagaagg tttcatcgaa    2760
ttctacaatc aaagaaggag atggggaccg tctaccactg caaacatttt ggatctgctt    2820
gaggatagcg atcacatcaa gttggttaac gatgatatat cctctctata tatattttat    2880
caagtgattt taatgattgg cacagtgatt ggtcccggaa cgatatttct catgttggtc    2940
ggtgcgtttg ttacggtttt caatgtttcc cagtttacgg cgttgtggct caatgttggt    3000
cccatttttgt ttttcgtgct cacttgtata atatgcaaat cggatacgca gttaatggtg    3060
gcagcaatac tgagcgcgat ctacggccta gtaatgataa tggtgctcat aggtgtcgcg    3120
atgcagatct acgacgatgg tgttctggcc ccttcttctc tgttcttctt cttaatgatg    3180
ggcgaatacg tggtagctgc aatgctccat ccaaaagagt tctactgtct taaatatggc    3240
gccatctact tgatcaccgt tccaagcatg tacatgttgc tcatcatcta ctctgtgttt    3300
aacatgaata acgtcagttg gggcaccagg gacgtcagcg tagcacctcc actgccagag    3360
ggccaaccga aacctccacc aaaaaaagaa aagtccttcg tagaagacgt actcgataaa    3420
atgaagaagt tctttatggc atgttgctcg ggagactcca agcatttagt tatgatcagt    3480
aattctttga cgcacattca atcaaaagtg gaacaaaata gacagaaagt cgaggatttg    3540
gagcggatca ctttggatcc agatgcggca gtgccaagga aaaccatggg aaaaaggaaa    3600
accactatta ttgaagggtc tagggcgtcg agacagtcac tccggaaatc aacgatgaac    3660
aaaccagggg ccatcccaaa tgaaaacgcc aatgcctcta ttgccgaaga tgatgaagaa    3720
gattatgatg aggaagagtc catcggtagc tcagacgatc ttcaaaacaa tagctggttc    3780
tacgcgggtg aactcctaag gggacgagtg actttcttgg ataaaaagga ggaaaagttt    3840
tggaaggagt tgctagatgc gtatttgcat cctattgaag atgataagga aaaagtggcc    3900
aaagacttga agatctgag agacagaatg accatgagct tcttcgcact aaacgtattt    3960
tttgtcacgg tagtatttct tcttaccatt aagaaagaca tacttcactt aaattggccg    4020
ttcaatccca cggtgaactt cacttacagt gccgccagca gcatcaatga gattgtcgtt    4080
gaaaaaacct acttgcaact ggaacctata ggattcgtgt ttttgatctt cttcttcgcc    4140
ctcatggggt gcagttcttt gggatgttgc tccatcgatt tggcacgttt tccacaaatt    4200
atggccaaca ccgatgtcga gtttggagaa aagaagatag aaaacttgac cgaggacgaa    4260
ctactagaaa aagactctat aaaaatcgta aaaaaactgg tgaaactcaa aggcattaac    4320
ggtgacgacg agaagacgga ggaagtagac gctcacgtat ccagaaggaa aaccgtggcg    4380
gacttggcga aaaacaaaga cagaaaacgt gcagtcatca acgacttgga ttccgccttt    4440
taaagcccgt atggcaaaaa atacgtaaag gagaagacgc gtggagtggc tttacctagg    4500
aaaacttggc agcaattcac agaagaagaa caacagttct aagagaaaaa tcaatgatgc    4560
cgcagttcaa tcccagcgcg tttaaggcgt ttaatcagca ttatggagag gagagtccta    4620
```

```
gcaggactat acatcatata gagaatcccg ggtatgatga tgatcctgct gacgcgtaga    4680
ttttatgtgc tagttgtttt agaatttta ataaataatt ttgggtctt                4729

<210> SEQ ID NO 17
<211> LENGTH: 10017
<212> TYPE: DNA
<213> ORGANISM: Anthonomus grandis

<400> SEQUENCE: 17
gatccttatt accttgattt tattcatatt tgacaattta aaagtagttt agtagattta      60
ttaaaattta tctttgtccg tggaatattt tattttgtg ataataaagc atattttaat     120
ttgattttac gtatttaatt tatttataac cccacatatg gatgtgtaac gtttttttta     180 aatttttgt taaaaattca cctctcaagc tatttggaca gcatcatatt ttaatatatt      240
ggtctgtaaa atactatact gatttaacaa tctgcagcaa ttttattaca gaatttatat     300
ttacaagtca tgtaataatt ttttaaaccc ttctgtttac ttaattttt aaataattta      360 aaactggtac tggtgaggat cactcaacgt aaggtagaca aaactaaaaa ttttttttatt    420 ttttccacta tttcttataa attttagccc ataattaaaa atctctcatt aaagttcatt     480
tttaaaatta gtactgactt aatgtatcat agtttcaaaa agcatatact tgcaatatag     540
ttataaaaat aattatcact agaaaaacat gcaacgcaag ataaatcagt attccattca     600
taaatagcta atctttggca attcagctaa aactttagta taaatagtgc gggttttag      660 aagttcttca catttggtct gtgtctacat caccaatcaa gatgtggtca acagtggctt     720
tgtgtttgtt gggtaagtct aattattttc tatctttttt tttcacattt aatgattttt     780
cttgtaaaaa tatggtttat ggctgctttt aaatactatt ttttatttta tttttttact    840
tcatgcaata tataaaatat atttaagaga atttagaaaa ctggagaaaa aaaagtttaa     900
aattattatg aaataaaggt aaactctgat tggttttttg gctcaatact caatatattt     960
ttatttcaat acacttttta gcatacaaat ttcaaacatt ctacatatat aatattgact    1020
tttttctata tattatattg taccctagaa aaaataatg atattttgcc aagacaaaat     1080 caaatttat atttaaaagt gtaacagctt tatacataac tttagtatag agtaaaattt     1140
tgccaaatta ttagattttg aaaagaaaat atccgcgaca attatcaaat aaataattaa    1200
tattttattg cgtctgcata ggcttataaa atttaaaaca taaggtacat aaagacatta     1260
agaagagcag ttgcaaaata tatcaatatt actaaaattg ttccctctat aataacgtct    1320
tttcacatta gtaatccttc ttggcaatat gcagtttaac aaaattaaac aaaaactact    1380
ttgtttggta gccactactt tacttcaaca ttttctatc ctctctttct atttttctat     1440
tttcttcttt ccattgagga caaatgccaa agcgtagct gaatactact gttcttttaa    1500
tatattcaat tttatactta acagatatat taaactcaat atctaatcca acaaatattg    1560
catcagtcca ttaatgaagt aattaagggg acatgtgaat tgatcagggt tgatagtctg    1620
ccagctaatc aagatggaca gttcctggat aaactgataa ctgaacagta atcggcacct    1680
taaggaaaaa ttgatacatt aaaaaatgtc ctgaagaaaa cttatttgaa ataaactaaa    1740
taatatcttt tatcaaaaat aataaaacta atattcttt aataccatcg tcttgccatt     1800
tgccccatat atcggaagtt ttttggatat gtttaagaaa ttttaaaat taattttaga    1860 acacataatt gaaagcacta atcatttca tactttttcag aagtatttta ttaaaaggaa    1920
tcccaattct aaaatattaa atttcatata cagtgcctca gataatattg ataaattgat    1980
```

```
taactatttta tttgcgatac attctttgta ttaattttcc taattcaaca catttctgag    2040
acgttttatg aatattttaa tatccagtat attgctaata aattctgaat ttcagttaaa    2100
cattcgatta attaatgcta attagtgaaa tgtttataca aaatatatat tataatatat    2160
ataatatttt gaagtttgac taagaattct tagatttttt gtttgttaga attgctttgc    2220
aaatatttta ttttaatgat cttgtttttt atgtagtttc taggcgcaga tatctctgat    2280
taatatgata aaaaaattat atattttaaa atatataaaa attctattaa aatctaaagg    2340
ttataatata tatgctggaa aaattttggt attacattcc aggaatgttt aggatttatg    2400
cgatatatac taaataccta tgctatgtgt atattgctta caacatttcc agaatgtgta    2460 attaatagggg tagctatgat acattttatt tttcaaatta tacgtctaaa ataagaatat    2520
gatatgtcaa ctgcaaatgt tctttccctt gggccttcgt gacttcaata taaggctgct    2580
tggcgacatt attacccgca tgaatccaat taagttttca agttaagttt tactaaaatt    2640
catttccttg tgaggttttt ttaattttat ctgttagagt gcctcttttt taagagctat    2700
atctatcccc tatcatcata ataatataaa catttgaaat aataataaat acttaccata    2760
ttaataacat ttttcttttg ctttacagtt ggactttctt atgtctcctc atcctcgcca    2820
gcctggaaag ataatacgga gtatgtctat tcagtaaatg gtcgtacact aaccggactt    2880
gaagaaaccg ctgatcagta ttctggtgtc tttctagaag ccaaattaca tctctctatt    2940
cgtcctgatg gaaagctcca aggccgaatt tctgaaccta aatttgctca gattctctct    3000
cagttacctg atgggtggaa atcagagatt cctgattcac aaattagtta caagcaatta    3060
caactttctc aaaaaccatt tcaactggtt ttagagaacg gtttaattaa gagactgatt    3120
gtggagaagg acactctaaa ctgggaggcc aatatcatca aaagtattgt aagtcaattc    3180
caaatggatt tacagggaga aaatgccttg cagaacccca ccagcagctt tcccactaat    3240
gaatatatgg atgccgtttt taaaccatg gaagaaactg taacaggcaa aactgaaacg    3300
atctatgaca ttcaccgtct tccagaatat ttagttcaaa gtcaaccttg gattgctcct    3360
caatataaac tgaaaggtga aggagacctt attgaagtca taaaatcaaa gaattatacc    3420
aacgctcgtg ataggccttc gtaccactat ggctttggag aaattgaaga atcagaacca    3480
actgctaata aaatgggaca gttctttata agacaatcaa attctagagc tattcttact    3540
ggaaaaccct ctagatatat tattcaaagc acttataccg ttaacaagat catggttaat    3600
ccaattctta agaataaaga aatgggatct attacaagta tggtcaatgt cacattacta    3660
gaaattaaca accaacaaca acagcctgaa gaactttcca atccttaga cattggaaat    3720 ttagtataca cttatggaca acctaaaaac aaccaagtac attcaaaatt aaatgaaaat    3780
ctcatggaag attcatccag cgaagagagt agtgaacagg aaatgactca tagaagattc    3840
cgccggtcag ccaactctct tacaaaacaa tggagagaaa gttctgaaga atggaatcaa    3900
caacaacaac aaccccgtcc tcagttaact agagctccgc attccccact tcttccatca    3960
atggttggct atcacggaaa atcaattaaa gaaaataaag actttgatat cagacaaaat    4020
gttgaaaatc tagttacgga aatcagtgac gaaattaagc aatcagaaaa aaccatctct    4080
aaacatacct tggataaaata cactatcctg aatactcttg ttcgcctgat ggacgaagac    4140
gatattcaat ttgtagccga gcagatgtat tctcagatga aaaacggaca gcagcgttat    4200
acctggagca ttttccgtga ctccgtagct gaagctggaa ctggaccagc ccttttgaac    4260
attaagaaat ggatagaaac caaaaaaatc caaaaaactg aagctgcaca agtaattggt    4320
actctagccc aatcaacacg tttcccaact gaagaatata tgcgcaagtt ctttgaattg    4380
```

```
gcaactgaaa ctcaagtcag acaacaagaa acactgaatc aaacatgtat tctatcttat    4440
accaacttag ttcacaaagt atacatcaat agaaatgaat ctcacaatca gtttccggtt    4500
catgcctttg gaagtttcta tactaaaaaa ggaagagaat tgtcaagac tactgtaatc     4560 ccccatctca agcaggaatt agaaaaagcg attagcaatg ctgataacaa taaaattcat    4620
gtaatgatcc gagctcttgg aaacattggg cacaaatcta tcctaaacgt gttccaaccc    4680
tatttcgaag gagaaaagca agtttctcaa tttcagagat taatgatggt tgcctgtatg    4740
gaccgactgg ctgattgtta tccgcatatt gcacgttctg ttttttataa ggtaacttaa    4800
gacttaacac tgtattgata tatagcttta gtcaatttaa gcacccatta tataaaaacc    4860
aaaattaatt tttcagatct accaaaatac tgccgagctt cctgaaattc gtgttgtagc    4920
agttcatcaa cttatcagag ctaatccacc cgtagagatg cttcaacgca tggctcaata    4980
taccaacact gactcccaag aagaggttaa cgctgcagtt aaatctgtca tcgaaagctc    5040
atgtaaactt gaatcatcca acatgctga attgtaagaa atctagcttt taatttttt     5100 accgttataa cagagttttt catttactag acggaaagca gctcagtccg ctagaccttt    5160
gctcacgaag aagcaaatatg gaatggaaca aagttatatt aacttgcgtg attatgtggc    5220
tgaacaaatg ggtcttgaac ttcacgtgca aagaactagc catagtagtg ctgaaagcag    5280
tttcccgaag attatgaaat tccaactcca ccaacataac catggaatga acagcacat    5340 tctgtctacc gggggaatga tatccagcat cagggagctt ttgaatgttt tatatagaca    5400
aactgaagtc ttccaacaag aaaaatctca gaggtaaaaa tcaatcgtca gtcagtctac    5460
agatcagtta acatgaattc acgtgtatat tattattata aataacgaaa agtaaaatgc    5520
agttttgctt tcacagatcg caggaacaag gtaaagacaa cgaatggtcc agcgccaata    5580
ttgctcggtt aatgaactat gaacgcgatg aacgtgaaca gttagaagct attatttatg    5640
ctcaagttga agatgtacaa aaactttggt ctttcgataa ccaaacttta gagcatctcc    5700
cagaaggtaa gttttttagta tattcgatag agcactaata tatgaaaatg tttgaatatt    5760
tgtagttatt cgtcagcaag aagaaattta cagacaagga aaagatttta gctatgtcaa    5820
gcttaaacag ctaaatgaaa tggcactctc cttccctact gaaatgggtc tgcctttctt    5880
gtatacctat gatgtgcctg tgttgatgaa ggttgaagga aaaattagag ctcttgccaa    5940
ccctgctatt tccagaaaca acaaactcac taaacctgaa caaatttcta ctgaaattaa    6000
agctagagtt acctgtactg gcaaaactca aagccatttg tctttcgtaa ctccatttga    6060
tcatcaaatc tatatggctg gttatgacaa gaatatgtat gttagtatcc cagtcaacgc    6120
aaggctcgaa atggatgtga aatctaagga agctaaaatt gaattcgaag ttgaacaaca    6180
gcaacaagat tctcgtttag tgcacattac tagcactccc tacacctcaa gaagtgatgt    6240
tatggcaatt agtcctgtag ctttgagacc aaacacatat gtaattaagt cccacaggaa    6300
caaccacaga tattttgact tcaatttcgg caaaaaagaa actggtttaa cattccgggg    6360
atggggacac catcctgaac aaagtatcgg atttaatgat ttagtatcta tgtggcaatc    6420
acgcggagtt gctggtgtat gggaacaatt atgggacaaa tgttctactg aatatagcga    6480
agctaccatc agttttattc caagtcaatc tactacccgt aaagctactt tccgtattaa    6540
tgttgatcaa aaataccaga aacaacctga gactcaaagt ccagaagatc ttctaacctt    6600
aaatcaactt tcatctaaat tgcaaaaaga tgaacctaaa caacgtcaac aagaaattaa    6660
aaaacacgtc gggtccggta tcaacagcgc tttattgtca tgctccgaca tctcgcttga    6720
```

```
atttgaggga gataagaaat acgaacacgt agtcggtttt gccgttgcaa agagtaatgc    6780
tgatcctaaa tcaagagtta tgttctatta caaaaacaaa aatgaaaata acagggagc    6840 tttggaaatc agaagcgaaa ttcctaacac caatggattg aatctagatg attccttgga    6900
tactgagcct tccaccaaat acaacatgcg attgcagtac ggaaatagcg aaaatgatgc    6960
ttttgaaatt tctgctcaag ctcaacttag tagaagccag gaacgaaagc aatatttaat    7020
taaccaagat ccattgtacc atgtatgtaa ggagcaaatg caacaaaaga acttccaact    7080
accagcttgc caaaacatga ctattaaagc caacttcctc gaccacatta aatatcaagt    7140
tcagtatcaa aaattgaact ggaagctggt tgaaactttg gaaggaatgt ttaagggatt    7200
gagagtatta tactatccaa tgactgaaat taaatcaatt tcttctgtcg gtcaaaatgt    7260
cgtagaagga gaagttcaat tccagccaga agattttaga caagtcaatg taacagtaag    7320
aaatactgat gaagaaactg tattcttcaa catttcttta aataatgaac ttttgagaac    7380
gctcctggtc cctcatccag tgttccatgc taaatgtaga tttgctggtt taatgcaagg    7440
tcaacaaaat tacagacgta agtttaataa tttggttaat tttctgtaaa taactatatt    7500
tctatttgtt ttttctttta taatcataag ttttattatt ttagccacat gcgtgattga    7560
ccaaaccact gctcaaacgt tcagcaataa gacctactca gttaatcttg acaaagaacc    7620
cactgtagta atgcagtatg ttcccaaaga tgctagagtt aatggacagc agtcaaaatc    7680
cgttgaacaa ttactgagag aaagcattga aaactatgtt gttcttgtcc gtcaagtcgc    7740
tgccaatcaa aaagaagtaa tcatcaactt aaaccatccc agaactcaag gaaaaactgt    7800
taagattgaa atgaaaccat cagaagacag acaaaaatct gctcgcaacc cagctgctaa    7860
agtcactatt gatggacaag agatgcactt cgatgataag caaatcgccg ataagtgtga    7920
tggatatgtt caagtatatg ctttacccaa cggagaagtt aaacttgaag tggaagatgc    7980 ttttttacctg atttatgatg ggcaacgtgt caaagtaact gccactggca caagcttcg    8040 agactcagta tatggttttgt gtggaagatt cagtcaagat aaacatgaag actttacagt    8100
tccttcaaac tgtgttacaa gagatactcg taagtttgtg gaaagttacc aagttgaaaa    8160
gggtcaacaa tggcgcaact ctccttctga acaatgcata aagaaagtat taccattgta    8220
cactaatgta atctccaacc agaatggttc ccaaatgaga acaaaacttg ccagtggaac    8280
tgtaatgaaa caccgctaca ttgaagaaaa tggtgaaatt tgctttacca ttcgcccact    8340
accagtctgc aacacctcag tcaaacaagt cgtgacgaaa aacgttcctg ttcactgtat    8400
ccaaggaacc aagaccgctt attactacaa atccctaatt gatcaaggag gaaacccaga    8460
tttcagccgt aagagtgaaa ctaggacagc tcgcatggaa gtagcagcac aatgcaacta    8520
aaattattag ccaatgcata taggaagtaa atttatattt attatttagg acgagcataa    8580
aaaaatgtaa aaaaaatcta tataaaataa agatatcaca gtcaattaaa ttaccatttc    8640 ttttatttt ataccaatcc gcaaaaataa tttggcatat atacaacgtc accctgtagt    8700
tgatcttatt agtttgatgt ttaaaattct tgtgacattc ttcgtgaagt tcgttttat    8760 aaagaatgtt tcgaagaaaa aagaattta agagactag ataatcaaac taaatcaaat    8820
caaacatttt ttattaccat ttagaaatac aaacaattac acaactaata tgccttttaa    8880
gattcaacta taattaactg tttatcacga ataaatatac ttttctggta atcggagtgt    8940
tgcgtttttt taaaaccgat gcccgtgcga ttctgggcat gagcgtacaa cccgtgtaaa    9000
gacaaaatat tagaaataac tccatatgtg cattatagcc taaataaact tcaatcagct    9060
aagcaggtct atcacaagtg aaccctccaa ataacatata acggtagttg tgcatttaaa    9120
```

```
acgtaagatt taataaagat acttctaggt taacattttt ttaagtgatt aggtcgccgc      9180
aggtcattcc acatgcaaat attttttaac tttgtcagtc tgaactgtgg ctatctaatt      9240
ttgataatct tatatattaa attatacata tgaactttcc ttctattgct catatttaaa      9300
attgaatttg aatttaaatg agtggtgtga tttctaaatg gtatgttaaa tgagtatctc      9360
atacagctat tttgtaattt tttaatttta gataaataaa ttgttaaaga atcaccgtac      9420
acaatgtctc cgtaatcgag caatgataaa acatgcacat cacacagcta atacatattt      9480
tattttttta atcggacata agcggctcta atcttgttac tatatactta tttaactttt      9540
acaacatgtg ttgtaaaggt taaatttgag tcaattacca ctcctaaact attttttctca     9600 acaacaatgg gtatagcttt agcccttata attattttga aggtatccac ccataaatta      9660
tgccaaaggt tcagttctcc ggtgatatcc aggttataaa atgcttggaa tgcctctgcg      9720
ttcttgtcca aatccattgc aacagctcgc tgcaacgctt tttgaagcat ttcattactt      9780
attctatttc tgagaatgtt cttgatattt ttgatgtatt cccccaccga gatcatgtcg      9840
atcgatttag ctttcagtgc gctaaccact gaaactgctg aatatttggc tattgtttgc      9900
agagcaataa taataataat agtagagcaa taaatactag ttttgtaacg tgctgaatgc      9960
aactgatacg cagattttct ggtggcacaa ttttcctcta cggataacgt ttctaga       10017
```

<210> SEQ ID NO 18
<211> LENGTH: 23
<212> TYPE: DNA
<213> ORGANISM: Artificial Sequence
<220> FEATURE:
<223> OTHER INFORMATION: Synthetic nucleotide sequence

<400> SEQUENCE: 18

```
taatacgact cactataggg aga                                                 23
```

<210> SEQ ID NO 19
<211> LENGTH: 13954
<212> TYPE: DNA
<213> ORGANISM: Artificial Sequence
<220> FEATURE:
<223> OTHER INFORMATION: Synthetic nucleotide sequence

<400> SEQUENCE: 19

```
ctgacgcgcc ctgtagcggc gcattaagcg cggcgggtgt ggtggttacg cgcagcgtga        60
ccgctacact tgccagcgcc ctagcgcccg ctcctttcgc tttcttccct tcctttctcg       120
ccacgttcgc cggctttccc cgtcaagctc taaatcgggg gctcccttta gggttccgat       180
ttagtgcttt acggcacctc gaccccaaaa aacttgatta gggtgatggt tcacgtagtg       240
ggccatcgcc ctgatagacg ttttttcgcc ctttgacgtt ggagtccacg ttctttaata       300
gtggactctt gttccaaact ggaacaacac tcaaccctat ctcggtctat tcttttgatt       360
tataagggat tttgccgatt tcggcctatt ggttaaaaaa tgagctgatt taacaaaaat       420
ttaacgcgaa ttttaacaaa atattaacgc ttacaatttg ccattcgcca tcaggctgc       480 gcaactgttg ggaagggcga tcggtgcggg cctcttcgct attacgccag ctggcgaaag       540
ggggatgtgc tgcaaggcga ttaagttggg taacgccagg gttttcccag tcacgacgtt       600
gtaaaacgac ggccagtgaa ttgtaatacg acggatcctt atgtatttcc aactttcatt       660
aacaatataa tcgcatataa atgaaaaatc gtttccagga taatattttg atgaaatctc       720
atattattgt tcgtactcgg attgatgttg aaggcttgaa gcgcttcaaa ttatagacca       780
```

```
gattatttaa gttttctttt tgtttactcc atatcaattt gatccattat actacctaag    840
aaaatttagg taacatagaa ttatttattg ttatagtaaa aaaaaggaaa accacaaaaa    900
taatctactt ttacgtatat actatttca tgacataagt aattaagttg tacaactttt    960
ttttaatgaa aagagagagt aaatttatca tgttcatgtg tagttacctc gtgaataacc   1020
gacggttata tagacgccta acatgaattg ttcagttgaa gacagttcaa aacatgtgtt   1080
tcactctaaa atcctcaaca aaaaaaaagt gttaaaattt gtaaacctct ttcaagcaaa   1140
aaaagaaaaa gtgttagaat cccaagattc tttcataatc cggaatcttg gctgaaaacg   1200
tataaaagag attgacgtag taacaaggag tcttggtatg cttccatgct ttttatcctt   1260
ttttgtcatg gaaccatgat ttggttacca tttattatgt aaccgaaatt ttcattgtaa   1320
taatgaatat ttaaatttt agcaaaaaaa aacaaaaaaa aacaaggagt cttgtcttcg   1380
ttctcaaatt tcagagctct tgcactttc aagagtttta ctttgatgag tgagacattt   1440
gtctttttag tgtttatttt ctaaacttaa aatagtagca tcaacatcac tcaattataa   1500
ttcttaagat gttgtagaaa atatttat agatggaaag taatcgatat taagacaaat   1560
aagaaaccaa accggacttt gtgttcagac cgaatcaaat ctgaattgga gaaattatgg   1620
tggaggcgaa agtcaacgga actaaagtat aaaaccaaat gtcaaaaata aaacccaatt   1680
ttcatcctta aacgaacctg ctgaaaccct aatttcgatt accaatttcg atctaaaaag   1740
aagtcatgga agccattgat tccgcaatcg atcctctcag agatttcgct aagagcagtg   1800
ttcgtctcgt ccagcgctgt cacaaacccg atcgcaaggg taacgccttt tctcaaaaaa   1860
atctcatttc cgattttga tctgtagatt agggttttct gaaattttga tatcatttgt   1920
aattgaattg gttatcagaa ttcacgaaag tagctgtgcg tacggcgatt ggatttgtgg   1980
tgatgggatt cgttggattc ttcgtgaagc tcgtttcat cccaatcaac aacatcatcg   2040
ttggatcttc ttagtgtagt actttcttta cgaggtaatt gatctcgcat tatatatcta   2100
cattttggtt atgttacttg acatatagtc attgattcaa tagttctgtt aattcctta   2160 aagatcattt tgactagacc acattcttgg ttcattcctc ataatttgt aatcatattg   2220 gtggatatag aagtagattg gttatagatc agatagtgga agactttagg atgaatttca   2280
gctagttttt ttttttggct tattgtctca aaagattagt gctttgctgt ctccattgct   2340
tctgctatcg acacgcttct gtctccttgt atctttatta tatctattcg tcccatgagt   2400
tttgtttgtt ctgtattcgt tcgctctggt gtcatggatg gagtctctgt tccatgtttc   2460
tgtaatgcat gttgggttgt ttcatgcaag aaatgctgag ataaacactc atttgtgaaa   2520
gtttctaaac tctgaatcgc gctacaggca atgctccgag gagtaggagg agaagaacga   2580
accaaacgac attatcagcc cttgaggaa gctcttagtt ttgttattgt ttttgtagcc   2640
aaattctcca ttcttattcc attttcactt atctcttgtt ccttatagac cttataagtt   2700
ttttattcat gtatacaaat tatattgtca tcaagaagta tctttaaaat ctaaatctca   2760
aatcaccagg actatgtttt tgtccaattc gtggaaccaa cttgcagctt gtatccattc   2820
tcttaaccaa taaaaaaaga aagaaagatc aatttgataa atttctcagc cacaaattct   2880
acatttaggt tttagcatat cgaaggctca atcacaaata caatagatag actagagatt   2940
ccagcgtcac gtgagtttta tctataaata aaggaccaaa aatcaaatcc cgagggcatt   3000
ttcgtaatcc aacataaaac ccttaaactt caagtctcat ttttaaacaa atcatgttca   3060
caagtctctt cttcttctct gtttctctat ctccttgctca tctttctcct gaaccatggc   3120
ggcggcaaca acaacaacaa caacatcttc ttcgatctcc ttctccacca aaccatctcc   3180
```

```
ttcctcctcc aaatcaccat taccaatctc cagattctcc ctcccattct ccctaaaccc    3240
caacaaatca tcctcctcct cccgccgccg cggtatcaaa tccagctctc cctcctccat    3300
ctccgccgtg ctcaacacaa ccaccaatgt cacaaccact ccctctccaa ccaaacctac    3360
caaacccgaa acattcatct cccgattcgc tccagatcaa ccccgcaaag gcgctgatat    3420
cctcgtcgaa gctttagaac gtcaaggcgt agaaaccgta ttcgcttacc ctggaggtgc    3480
atcaatggag attcaccaag ccttaacccg ctcttcctca atccgtaacg tccttcctcg    3540
tcacgaacaa ggaggtgtat tcgcagcaga aggatacgct cgatcctcag gtaaaccagg    3600
tatctgtata gccacttcag gtcccggagc tacaaatctc gttagcggat tagccgatgc    3660
gttgttagat agtgttcctc ttgtagcaat cacaggacaa gtccctcgtc gtatgattgg    3720
tacagatgcg tttcaagaga ctccgattgt tgaggtaacg cgttcgatta cgaagcataa    3780
ctatcttgtg atggatgttg aagatatccc taggattatt gaggaagctt tcttttttagc   3840
```
(continuing...)

ttcctcctcc aaatcaccat taccaatctc cagattctcc ctcccattct ccctaaaccc    3240
caacaaatca tcctcctcct cccgccgccg cggtatcaaa tccagctctc cctcctccat    3300
ctccgccgtg ctcaacacaa ccaccaatgt cacaaccact ccctctccaa ccaaacctac    3360
caaacccgaa acattcatct cccgattcgc tccagatcaa ccccgcaaag gcgctgatat    3420
cctcgtcgaa gctttagaac gtcaaggcgt agaaaccgta ttcgcttacc ctggaggtgc    3480
atcaatggag attcaccaag ccttaacccg ctcttcctca atccgtaacg tccttcctcg    3540
tcacgaacaa ggaggtgtat tcgcagcaga aggatacgct cgatcctcag gtaaaccagg    3600
tatctgtata gccacttcag gtcccggagc tacaaatctc gttagcggat tagccgatgc    3660
gttgttagat agtgttcctc ttgtagcaat cacaggacaa gtccctcgtc gtatgattgg    3720
tacagatgcg tttcaagaga ctccgattgt tgaggtaacg cgttcgatta cgaagcataa    3780
ctatcttgtg atggatgttg aagatatccc taggattatt gaggaagctt tcttttttagc   3840 tacttctggt agacctggac ctgttttggt tgatgttcct aaagatattc aacaacagct    3900
tgcgattcct aattgggaac aggctatgag attacctggt tatatgtcta ggatgcctaa    3960
acctccggaa gattctcatt tggagcagat tgttaggttg atttctgagt ctaagaagcc    4020
tgtgttgtat gttggtggtg gttgtttgaa ttctagcgat gaattgggta ggtttgttga    4080
gcttacgggg atccctgttg cgagtacgtt gatggggctg ggatcttatc cttgtgatga    4140
tgagttgtcg ttacatatgc ttggaatgca tgggactgtg tatgcaaatt acgctgtgga    4200
gcatagtgat tgttgttgg cgtttggggt aaggtttgat gatcgtgtca cgggtaagct    4260
tgaggctttt gctagtaggg ctaagattgt tcatattgat attgactcgg ctgagattgg    4320
gaagaataag actcctcatg tgtctgtgtg tggtgatgtt aagctggctt tgcaagggat    4380
gaataaggtt cttgagaacc gagcggagga gcttaagctt gattttggag tttggaggaa    4440
tgagttgaac gtacagaaac agaagttttcc gttgagcttt aagacgtttg gggaagctat    4500
tcctccacag tatgcgatta aggtccttga tgagttgact gatggaaaag ccataataag    4560
tactggtgtc gggcaacatc aaatgtgggc ggcgcagttc tacaattaca agaaaccaag    4620
gcagtggcta tcatcaggag gccttggagc tatgggattt ggacttcctg ctgcgattgg    4680
agcgtctgtt gctaaccctg atgcgatagt tgtggatatt gacggagatg gaagctttat    4740
aatgaatgtg caagagctag ccactattcg tgtagagaat cttccagtga aggtactttt    4800
attaaacaac cagcatcttg gcatggttat gcaatgggaa gatcggttct acaaagctaa    4860
ccgagctcac acatttctcg gtgatccggc tcaggaggac gagatattcc gaacatgtt    4920 gctgtttgca gcagcttgcg ggattccagc ggcgagggtg acaaagaaag cagatctccg    4980
agaagctatt cagacaatgc tggatacacc aggaccttac ctgttggatg tgattttgtcc   5040 gcaccaagaa catgtgttgc cgatgatccc gaatggtggc actttcaacg atgtcataac    5100
ggaaggagat ggccggatta atactgaga gatgaaaccg gtgattatca gaaccttta    5160 tggtctttgt atgcatatgg taaaaaaact tagtttgcaa tttcctgttt gttttggtaa    5220
tttgagtttc ttttagttgt tgatctgcct gcttttttggt ttacgtcaga ctactactgc    5280
tgttgttgtt tggtttcctt tctttcattt tataaataaa taatccggtt cggtttactc    5340
cttgtgactg gctcagtttg gttattgcga aatgcgaatg gtaaattgag taattgaaat    5400
tcgttattag ggttctaagc tgttttaaca gtcactgggt taatatctct cgaatcttgc    5460
atggaaaatg ctcttaccat tggttttaa ttgaaatgtg ctcatatggg ccgtggtttc    5520

```
caaattaaat aaaactacga tgtcatcgag aagtaaaatc aactgtgtcc acattatcag    5580
ttttgtgtat acgatgaaat agggtaattc aaaatctagc ttgatatgcc ttttggttca    5640
ttttaacctt ctgtaaacat ttttcagat tttgaacaag taaatccaaa aaaaaaaaa     5700 aaaaatctca actcaacact aaattatttt aatgtataaa agatgcttaa acatttggc    5760 ttaaaagaaa gaagctaaaa acatagagaa ctcttgtaaa ttgaagtatg aaaatatact    5820
gaattgggta ttatatgaat ttttctgatt taggattcac atgatccaaa aaggaaatcc    5880
agaagcacta atcagacatt ggaagtagga atatttcaaa aagttttttt tttttaagta    5940
agtgacaaaa gcttttaaaa aatagaaaag aaactagtat taaagttgta aatttaataa    6000 acaaagaaa ttttttatat tttttcattt cttttccag catgaggtta tgatggcagg     6060
atgtggattt catttttttc cttttgatag cctttaatt gatctattat aattgacgaa     6120
aaaatattag ttaattatag atatatttta ggtagtatta gcaatttaca cttccaaaag    6180
actatgtaag ttgtaaatat gatgcgttga tctcttcatc attcaatggt tagtcaaaaa    6240
aataaaagct taactagtaa actaaagtag tcaaaaattg tactttagtt taaaatatta    6300
gaataatcca aaacgacatt tatgtgaaac aaaaacaata ctcgagagtg aagtagcaga    6360
gataatagtt attacagtag cagtaataaa ataaaataca ttttattaca aaaaaacgta    6420
caagaggtcc gcgaagatag ccaatgagaa cgcaagaaga caacccaatt ctcctatttt    6480
tttattaaat atttctagaa gaaagggtaa attacgcccc acggtcacaa aactattaat    6540
aagatcatat atttatcact caacttccaa aagttacaaa atgattatta aactattcaa    6600
aagttttatt tcaagtcatt ggattgttaa aatagcattt gtatggattt ccctgttcac    6660
attgcctaca tcaatcgaag cctctcattc cccttctttt ttatagatta agttttttt    6720 tataaaacaa ttttaaacat catgaatctc tgaactaaaa tttaaataac ttttttcttc    6780
gatctttgac attgattgtt aaattaactt gaatctaagg tttgttctac ttgttgataa    6840
atacagatcc atcgtgttga tcattgaatc gtcacttgga gctcactcat cggacttaaa    6900
aaaaaaacct taacaaccta gtgacttaaa taaaacttt gaatagttta ctgactattt     6960
tgtaactttt taaagttaag tgactaaaac gtgaacatac taatagttta gtgacctcgg    7020
ttgattttac ccaaaaaatt attattcaac ctctcgtcct ctcctttta cacctttta      7080 ttattttta ttttttctct ttactttgtt ttttagcta tttccagcga ctactaaaca      7140
aaataaaaat tagcccagga caggaggatc tctcagctac ttttttctc aaaatttctc     7200 caattagctc tgtaattttc tatttgtttt ctctttattt tagattttt ttggtccgtg     7260 ttaatcttcg ttgaaggcga tctagctttg atttgaattt cattttttt ctttttttcct    7320 tttaagatac ttttttgttt gttttagggt ttaggcgaag tagacgctca cgtatccaga    7380
aggaaaaccg tggcggactt ggcgaaaaac aaagacagaa aacgtgcagt catcaacgac    7440
ttggattccg ccttttaaag cccgtatggc aaaaaatacg taaaggagaa gacgcgtgga    7500
gtggctttac ctaggaaaac tttggcagca attcacagaa gatctttttt ccttttagta    7560
taaaatagtt aagtgatgtt aattagtatg attataataa tatagttgtt ataattgtga    7620
aaaaataatt tataaatata ttgttttacat aaacaacata gtaatgtaaa aaaatatgac   7680
aagtgatgtg taagacgaag aagataaaag ttgagagtaa gtatattatt tttaatgaat    7740
ttgatcgaac atgtaagatg atatactagc attaatattt gttttaatca taatagtaat    7800
tctagctggt ttgatgaatt aaatatcaat gataaaatac tatagtaaaa ataagaataa    7860
ataaattaaa ataatatttt tttatgatta atagtttatt atataattaa atatctatac    7920
```

```
cattactaaa tattttagtt taaaagttaa taaatatttt gttagaaatt ccaatctgct    7980
tgtaatttat caataaacaa aatattaaat aacaagctaa agtaacaaat aatatcaaac    8040
taatagaaac agtaatctaa tgtaacaaaa cataatctaa tgctaatata acaaagcgca    8100
agatctatca ttttatatag tattattttc aatcaacatt cttattaatt tctaaataat    8160
acttgtagtt ttattaactt ctaaatggat tgactattaa ttaaatgaat tagtcgaaca    8220
tgaataaaca aggtaacatg atagatcatg tcattgtgtt atcattgatc ttacatttgg    8280
attgtcttct gtgaattgct gccaaagttt cctaggtaa agccactcca cgcgtcttct     8340
cctttacgta ttttttgcca tacgggcttt aaaaggcgga atccaagtcg ttgatgactg    8400
cacgttttct gtctttgttt ttcgccaagt ccgccacggt tttccttctg gatacgtgag    8460
cgtctacttc gatcgttcaa acatttggca ataaagtttc ttaagattga atcctgttgc    8520
cggtcttgcg atgattatca tataattttct gttgaattac gttaagcatg taatatttaa   8580
catgtaatgc atgacgttat ttatgagatg ggttttttatg attagagtcc cgcaattata   8640
catttaatac gcgatagaaa acaaaatatc gcgcgcaaac ttggataaat tatcgcgcgc    8700
ggtgtcatct atgaggacta gatcggctcg agggtacccc tatttatagt tgaggttcaa    8760
ggaccaaaca ataaatagcc cattatctca aggacaaaaa aaaaattatc ccatgccact    8820
ttttcaaagt caactttagg gtgctaaact tgcaccactt ggattgtttg ccattaaaat    8880
tgtctgccat taatcataat gttaacatag gttaccattg agtaccgaat gagttccctt    8940
aatggcaaca ttttaggtac taaaactcga aggttcatcg ataccgcttt agcggcagct    9000
ttcgggaggt ttttggtgag gaagaaaccg cagttgcctt gatcgtcttc gattcgagtg    9060
cagctaccat acgcttcgtc gatcgaaccg acatggggttc ggaccaagtg gttcagtttc    9120
aaaatggctc gatgtttaag ccctcttctg ttctttaaaa gcaagaaaca accccctata    9180
cgaaaaagaa tattagggag catcatggac ctttctttgc ctacatacca attagggctt    9240
aatgattccg agctcacaac aatggcgaat tggttcttat atgtttgaaa caaatggttc    9300
acaagatcaa tggctataac actcgcacga caaaaaggac aacacaaaga gagatcaaaa    9360
aaacccgaca ccaaggggca tcaagtaata aacagccccc acagcttcaa actaagttcc    9420
tttctttctt ttttttgactt tcttttcaagg gaagaaagga gagaaagatt ttatgctttt    9480
tttattataa aataaataaa aaaacagctg gccgccatgg ggaggcactt gcttcatctt    9540
tatcttatga tccttcctga taccttgatg agaatgagac caaataatgc acttcagaac    9600
atgaattata aggattattt gagaatgtca gagggatatg acaacaagta ctttgccaat    9660
cctgaggttt tcgcagctcc aggtggaatc actactggta ttactatcgt tacaaaattg    9720
cttggttggc ttggattgcc attcgctggt gaaaccggaa tggcattgaa ttttattctt    9780
ggattgcttt ggccaacttc tggtaatcct tgggctgaat tgatgatatt ggtggaagaa    9840
ttgatcaatc aaaagattga ggagaccgtt aggaacaagg cacttgcaga tcttggaaac    9900
tcaggaagag ctcttcagtc atatcttaac gctttcgaag attggcaaaa gaatccaaat    9960
attttcagat caaagagct tgttaaggaa aggttctcta atgctgaaca ctcattgagg    10020
actgaaatgt catcattcgc aataagaggt tttgagattc tcttttggc tacatacgcc    10080 caagctgcta attgcatct tttcttgatc aaggatattc aaatctacgg taaggaatgg    10140
ggttacaccc aagcagacat cgacctttc tacagagaac aagttgaatt tactaaggaa    10200
tatacagagc actgtattaa tatctataat gatggattga accagcttaa gggatcaaac    10260
```

```
gctaagcagt ggattgcatt caacaggttt agaagggaaa tgacattgac agttttggac   10320
gttgtggctc ttttccctaa ctacgacgtg aggatgtatc ctatcaaaac taccacagag   10380
ttgaccagga caatatatac tgatcctttg ggttatacta agaccggttc atcatctact   10440
ccaccatggt gcaattatgg atcttctttt tcatacattg agtcagttgc tattcctgct   10500
ccttcattgg tgaaatggct ttctcaaata gaaatctact caaagtctgc tagggccaca   10560
cctcaatctg ctgactactg ggctggtcat accattacat accattactc aggtgatgat   10620
ggacaagcag ttgctaacta tggtgacagg actaatccag tgatagtgaa taggtacaac   10680
ttcgaacagg ctgatatata cagggtttca tcatctgttg cttcatcaac cacctctgga   10740
gttaagttgc ttactactaa ggctatattt gatggaatat caactaacaa cggacttgtt   10800
tcatacatgt acgaaaaact ttcaaatttt tttaatgagc ttaaagacac catcactgaa   10860
cttcctgtgc aaatttcttc tcctccaaca tacggtgacg cagaacagta ctctcacaga   10920
ttgtcttatg tgtctaatgc tcctacagag tactcttctg gaggacacct tattcttgga   10980
cttatacctg tgcttggttg gacccatacc tcacttaccc aaaccaacca aatccactca   11040
gattctatca cacaaattcc tgctgtgaag gcaaattctg tgtcttctta tgtgactgtt   11100
gaaaaaggta caggttttac tggaggagat ttggttaaat tttctacagg tttcatgtct   11160
actggtattc aattcaattt gaaaattgag gagggtaaaa gatacagaat tagaattaga   11220
tatgcagccg atgttaatgc cactctttct gcattgggtc ttaacgatgc cttcattaac   11280
attgagtcta caatgtcaca ggacactcct cttaaatata acgattttca gtatgccgag   11340
gccgataaaa cagttcattt gtataaccca agattctcat tgtatttgga gaactctgac   11400
cagtctggta aatctatcta tattgatagg atcgagttca tcccagttga taacggatct   11460
ttgaaccacc atcatcatca tcattaacga tcgttcaaac attttggcaat aaagtttctt   11520 aagattgaat cctgttgccg gtcttgcgat gattatcata taatttctgt tgaattacgt   11580
taagcatgta atatttaaca tgtaatgcat gacgttattt atgagatggg ttttttatgat   11640 tagagtcccg caattataca tttaatacgc gatagaaaac aaaatatcgc gcgcaaactt   11700
ggataaatta tcgcgcgcgg tgtcatctat gaggactaga tcggggtacc ggatcctcga   11760
ggttcccttt agtgagggtt aattgcgagc ttggcgtaat catggtcata gctgtttcct   11820
gtgtgaaatt gttatccgct cacaattcca cacaacatac gagccggaag cataaagtgt   11880
aaagcctggg gtgcctaatg agtgagctaa ctcacattaa ttgcgttgcg ctcactgccc   11940
gctttccagt cgggaaacct gtcgtgccag ctgcattaat gaatcggcca acgcgcgggg   12000
agaggcggtt tgcgtattgg gcgctcttcc gcttcctcgc tcactgactc gctgcgctcg   12060
gtcgttcggc tgcggcgagc ggtatcagct cactcaaagg cggtaatacg gttatccaca   12120
gaatcagggg ataacgcagg aaagaacatg tgagcaaaag gccagcaaaa ggccaggaac   12180
cgtaaaaagg ccgcgttgct ggcgtttttc cataggctcc gcccccctga cgagcatcac   12240
aaaaatcgac gctcaagtca gaggtggcga acccgacag gactataaag ataccaggcg   12300
tttccccctg gaagctccct cgtgcgctct cctgttccga ccctgccgct taccggatac   12360
ctgtccgcct ttctcccttc gggaagcgtg gcgctttctc atagctcacg ctgtaggtat   12420
ctcagttcgg tgtaggtcgt tcgctccaag ctgggctgtg tgcacgaacc cccgttcag   12480 cccgaccgct gcgccttatc cggtaactat cgtcttgagt ccaacccggt aagacacgac   12540
ttatcgccac tggcagcagc cactggtaac aggattagca gagcgaggta tgtaggcggt   12600
gctacagagt tcttgaagtg gtggcctaac tacggctaca ctagaagaac agtatttggt   12660
```

```
atctgcgctc tgctgaagcc agttaccttc ggaaaaagag ttggtagctc ttgatccggc   12720
aaacaaacca ccgctggtag cggtggtttt tttgtttgca agcagcagat tacgcgcaga   12780
aaaaaaggat ctcaagaaga tcctttgatc ttttctacgg ggtctgacgc tcagtggaac   12840
gaaaactcac gttaagggat tttggtcatg agattatcaa aaaggatctt cacctagatc   12900
cttttaaatt aaaaatgaag ttttaaatca atctaaagta tatatgagta aacttggtct   12960
gacagttacc aatgcttaat cagtgaggca cctatctcag cgatctgtct atttcgttca   13020
tccatagttg cctgactccc cgtcgtgtag ataactacga tacgggaggg cttaccatct   13080
ggccccagtg ctgcaatgat accgcgagac ccacgctcac cggctccaga tttatcagca   13140
ataaaccagc cagccggaag ggccgagcgc agaagtggtc ctgcaacttt atccgcctcc   13200
atccagtcta ttaattgttg ccgggaagct agagtaagta gttcgccagt taatagtttg   13260
cgcaacgttg ttgccattgc tacaggcatc gtggtgtcac gctcgtcgtt tggtatggct   13320
tcattcagct ccggttccca acgatcaagg cgagttacat gatcccccat gttgtgcaaa   13380
aaagcggtta gctccttcgg tcctccgatc gttgtcagaa gtaagttggc cgcagtgtta   13440
tcactcatgg ttatggcagc actgcataat tctcttactg tcatgccatc cgtaagatgc   13500
ttttctgtga ctggtgagta ctcaaccaag tcattctgag aatagtgtat gcggcgaccg   13560
agttgctctt gcccggcgtc aatacgggat aataccgcgc cacatagcag aactttaaaa   13620
gtgctcatca ttggaaaacg ttcttcgggg cgaaaactct caaggatctt accgctgttg   13680
agatccagtt cgatgtaacc cactcgtgca cccaactgat cttcagcatc ttttactttc   13740
accagcgttt ctgggtgagc aaaaacagga aggcaaaatg ccgcaaaaaa gggaataagg   13800
gcgacacgga aatgttgaat actcatactc ttcctttttc aatattattg aagcatttat   13860
cagggttatt gtctcatgag cggatacata tttgaatgta tttagaaaaa taaacaaata   13920
ggggttccgc gcacatttcc ccgaaaagtg ccac                              13954
```

<210> SEQ ID NO 20
<211> LENGTH: 13938
<212> TYPE: DNA
<213> ORGANISM: Artificial Sequence
<220> FEATURE:
<223> OTHER INFORMATION: Synthetic nucleotide sequence

<400> SEQUENCE: 20

```
ctgacgcgcc ctgtagcggc gcattaagcg cggcgggtgt ggtggttacg cgcagcgtga     60
ccgctacact tgccagcgcc ctagcgcccg ctcctttcgc tttcttccct tcctttctcg    120
ccacgttcgc cggctttccc cgtcaagctc taaatcgggg gctcccttta gggttccgat    180
ttagtgcttt acggcacctc gaccccaaaa aacttgatta gggtgatggt tcacgtagtg    240
ggccatcgcc ctgatagacg gttttttcgcc ctttgacgtt ggagtccacg ttctttaata    300
gtggactctt gttccaaact ggaacaacac tcaaccctat ctcggtctat tcttttgatt    360
tataagggat tttgccgatt tcggcctatt ggttaaaaaa tgagctgatt taacaaaaat    420
ttaacgcgaa ttttaacaaa atattaacgc ttacaatttg ccattcgcca ttcaggctgc    480
gcaactgttg ggaagggcga tcggtgcggg cctcttcgct attacgccag ctggcgaaag    540
ggggatgtgc tgcaaggcga ttaagttggg taacgccagg gttttcccag tcacgacgtt    600
gtaaaacgac ggccagtgaa ttgtaatacg acggatcctt atgtatttcc aactttcatt    660
aacaatataa tcgcatataa atgaaaaatc gtttccagga taatatttg atgaaatctc    720
```

```
atattattgt tcgtactcgg attgatgttg aaggcttgaa gcgcttcaaa ttatagacca      780
gattatttaa gtttttcttt tgtttactcc atatcaattt gatccattat actacctaag      840
aaaatttagg taacatagaa ttatttattg ttatagtaaa aaaaaggaaa accacaaaaa      900
taatctactt ttacgtatat actattttca tgacataagt aattaagttg tacaactttt      960
ttttaatgaa aagagagagt aaatttatca tgttcatgtg tagttacctc gtgaataacc     1020
gacggttata tagacgccta acatgaattg ttcagttgaa gacagttcaa aacatgtgtt     1080
tcactctaaa atcctcaaca aaaaaaagt gttaaaattt gtaaacctct ttcaagcaaa      1140
aaaagaaaaa gtgttagaat cccaagattc tttcataatc cggaatcttg gctgaaaacg     1200
tataaaagag attgacgtag taacaaggag tcttggtatg cttccatgct tttatcctt      1260 ttttgtcatg gaaccatgat ttggttacca tttattatgt aaccgaaatt ttcattgtaa     1320
taatgaatat ttaaattttt agcaaaaaaa aacaaaaaaa aacaaggagt cttgtcttcg     1380
ttctcaaatt tcagagctct tgcactttc aagagtttta ctttgatgag tgagacattt      1440 gtcttttag tgtttatttt ctaaacttaa aatagtagca tcaacatcac tcaattataa      1500
ttcttaagat gttgtagaaa atatttttat agatggaaag taatcgatat taagacaaat     1560
aagaaaccaa accggacttt gtgttcagac cgaatcaaat ctgaattgga gaaattatgg     1620
tggaggcgaa agtcaacgga actaaagtat aaaaccaaat gtcaaaaata aaacccaatt     1680
ttcatcctta aacgaacctg ctgaaaccct aatttcgatt accaattccg atctaaaaag     1740
aagtcatgga agccattgat tccgcaatcg atcctctcag agatttcgct aagagcagtg     1800
ttcgtctcgt ccagcgctgt cacaaacccg atcgcaaggg taacgccttt tctcaaaaaa     1860
atctcatttc cgattttga tctgtagatt agggttttct gaaattttga tatcatttgt      1920
aattgaattg gttatcagaa ttcacgaaag tagctgtgcg tacggcgatt ggatttgtgg     1980
tgatgggatt cgttggattc ttcgtgaagc tcgttttcat cccaatcaac aacatcatcg     2040
ttggatcttc ttagtgtagt actttcttta cgaggtaatt gatctcgcat tatatatcta     2100
cattttggtt atgttacttg acatatagtc attgattcaa tagttctgtt aattccttta     2160
aagatcattt tgactagacc acattcttgg ttcattcctc aataatttgt aatcatattg     2220
gtggatatag aagtagattg gttatagatc agatagtgga agactttagg atgaatttca     2280
gctagttttt tttttggct tattgtctca aaagattagt gctttgctgt ctccattgct      2340
tctgctatcg acacgcttct gtctccttgt atctttatta tatctattcg tcccatgagt     2400
tttgtttgtt ctgtattcgt tcgctctggt gtcatggatg gagtctctgt tccatgtttc     2460
tgtaatgcat gttgggttgt ttcatgcaag aaatgctgag ataaacactc atttgtgaaa     2520
gtttctaaac tctgaatcgc gctacaggca atgctccgag gagtaggagg agaagaacga     2580
accaaacgac attatcagcc ctttgaggaa gctcttagtt ttgttattgt ttttgtagcc     2640
aaattctcca ttcttattcc atttttcactt atctcttgtt ccttatagac cttataagtt     2700
ttttattcat gtatacaaat tatattgtca tcaagaagta tctttaaaat ctaaatctca     2760
aatcaccagg actatgtttt tgtccaattc gtggaaccaa cttgcagctt gtatccattc     2820
tcttaaccaa taaaaaaaga aagaaagatc aatttgataa atttctcagc cacaaattct     2880
acatttaggt tttagcatat cgaaggctca atcacaaata caatagatag actagagatt     2940
ccagcgtcac gtgagtttta tctataaata aaggaccaaa aatcaaatcc cgagggcatt     3000
ttcgtaatcc aacataaaac ccttaaactt caagtctcat ttttaaacaa atcatgttca     3060
caagtctctt cttcttctct gtttctctat ctcttgctca tctttctcct gaaccatggc     3120
```

```
ggcggcaaca acaacaacaa caacatcttc ttcgatctcc ttctccacca aaccatctcc    3180
ttcctcctcc aaatcaccat taccaatctc cagattctcc ctcccattct ccctaaaccc    3240
caacaaatca tcctcctcct cccgccgccg cggtatcaaa tccagctctc cctcctccat    3300
ctccgccgtg ctcaacacaa ccaccaatgt cacaaccact ccctctccaa ccaaacctac    3360
caaacccgaa acattcatct cccgattcgc tccagatcaa ccccgcaaag gcgctgatat    3420
cctcgtcgaa gctttagaac gtcaaggcgt agaaaccgta ttcgcttacc ctggaggtgc    3480
atcaatggag attcaccaag ccttaacccg ctcttcctca atccgtaacg tccttcctcg    3540
tcacgaacaa ggaggtgtat tcgcagcaga aggatacgct cgatcctcag gtaaaccagg    3600
tatctgtata gccacttcag gtcccggagc tacaaatctc gttagcggat tagccgatgc    3660
gttgttagat agtgttcctc ttgtagcaat cacaggacaa gtccctcgtc gtatgattgg    3720
tacagatgcg tttcaagaga ctccgattgt tgaggtaacg cgttcgatta cgaagcataa    3780
ctatcttgtg atggatgttg aagatatccc taggattatt gaggaagctt tcttttttagc    3840 tacttctggt agacctggac ctgttttggt tgatgttcct aaagatattc aacaacagct    3900
tgcgattcct aattgggaac aggctatgag attacctggt tatatgtcta ggatgcctaa    3960
acctccggaa gattctcatt tggagcagat tgttaggttg atttctgagt ctaagaagcc    4020
tgtgttgtat gttggtggtg gttgtttgaa ttctagcgat gaattgggta ggtttgttga    4080
gcttacgggt atccctgttg cgagtacgtt gatggggctg ggatcttatc cttgtgatga    4140
tgagttgtcg ttacatatgc ttggaatgca tgggactgtg tatgcaaatt acgctgtgga    4200
gcatagtgat ttgttgttgg cgtttggggt aaggtttgat gatcgtgtca cgggtaagct    4260
tgaggctttt gctagtaggg ctaagattgt tcatattgat attgactcgg ctgagattgg    4320
gaagaataag actcctcatg tgtctgtgtg tggtgatgtt aagctggctt tgcaagggat    4380
gaataaggtt cttgagaacc gagcggagga gcttaagctt gattttggag tttggaggaa    4440
tgagttgaac gtacagaaac agaagtttcc gttgagcttt aagacgtttg gggaagctat    4500
tcctccacag tatgcgatta aggtccttga tgagttgact gatggaaaag ccataataag    4560
tactggtgtc gggcaacatc aaatgtgggc ggcgcagttc tacaattaca agaaaccaag    4620
gcagtggcta tcatcaggag gccttggagc tatgggattt ggacttcctg ctgcgattgg    4680
agcgtctgtt gctaaccctg atgcgatagt tgtggatatt gacggagatg gaagctttat    4740
aatgaatgtg caagagctag ccactattcg tgtagagaat cttccagtga aggtactttt    4800
attaaacaac cagcatcttg gcatggttat gcaatgggaa gatcggttct acaaagctaa    4860
ccgagctcac acatttctcg gtgatccggc tcaggaggac gagatattcc gaacatgtt    4920 gctgttttgca gcagcttgcg ggattccagc ggcgagggtg acaaagaaag cagatctccg    4980
agaagctatt cagacaatgc tggatacacc aggaccttac ctgttggatg tgatttgtcc    5040
gcaccaagaa catgtgttgc cgatgatccc gaatggtggc actttcaacg atgtcataac    5100
ggaaggagat ggccggatta aatactgaga gatgaaaccg gtgattatca gaacctttta    5160
tggtctttgt atgcatatgg taaaaaaact tagtttgcaa tttcctgttt gttttggtaa    5220
tttgagtttc ttttagttgt tgatctgcct gcttttggt ttacgtcaga ctactactgc    5280
tgttgttgtt tggtttcctt tctttcattt tataaataaa taatccggtt cggtttactc    5340
cttgtgactg gctcagtttg gttattgcga aatgcgaatg gtaaattgag taattgaaat    5400
tcgttattag ggttctaagc tgtttaaaca gtcactgggt taatatctct cgaatcttgc    5460
```

```
atggaaaatg ctcttaccat tggttttta ttgaaatgtg ctcatatggg ccgtggtttc    5520
caaattaaat aaaactacga tgtcatcgag aagtaaaatc aactgtgtcc acattatcag    5580
ttttgtgtat acgatgaaat agggtaattc aaaatctagc ttgatatgcc ttttggttca    5640
ttttaacctt ctgtaaacat tttttcagat tttgaacaag taaatccaaa aaaaaaaaaa    5700
aaaaatctca actcaacact aaattatttt aatgtataaa agatgcttaa aacatttggc    5760
ttaaaagaaa gaagctaaaa acatagagaa ctcttgtaaa ttgaagtatg aaaatatact    5820
gaattgggta ttatatgaat ttttctgatt taggattcac atgatccaaa aaggaaatcc    5880
agaagcacta atcagacatt ggaagtagga atatttcaaa aagttttttt ttttaagta    5940 agtgacaaaa gcttttaaaa aatagaaaag aaactagtat taaagttgta aatttaataa    6000 acaaagaaa tttttatat tttttcattt ctttttccag catgaggtta tgatggcagg    6060
atgtggattt catttttttc cttttgatag ccttttaatt gatctattat aattgacgaa    6120
aaaatattag ttaattatag atatatttta ggtagtatta gcaatttaca cttccaaaag    6180
actatgtaag ttgtaaatat gatgcgttga tctcttcatc attcaatggt tagtcaaaaa    6240
aataaaagct taactagtaa actaaagtag tcaaaaattg tactttagtt taaaatatta    6300
gaataatcca aaacgacatt tatgtgaaac aaaaacaata ctcgagagtg aagtagcaga    6360
gataatagtt attacagtag cagtaataaa ataaaataca ttttattaca aaaaaacgta    6420
caagaggtcc gcgaagatag ccaatgagaa cgcaagaaga caacccaatt ctcctatttt    6480
tttattaaat atttctagaa gaaagggtaa attacgcccc acggtcacaa aactattaat    6540
aagatcatat atttatcact caacttccaa aagttacaaa atgattatta aactattcaa    6600 aagtttttatt tcaagtcatt ggattgttaa aatagcattt gtatggattt ccctgttcac    6660
attgcctaca tcaatcgaag cctctcattc cccttctttt ttatagatta agttttttt    6720 tataaacaa ttttaaacat catgaatctc tgaactaaaa tttaaataac tttttcttc    6780 gatctttgac attgattgtt aaattaactt gaatctaagg tttgttctac ttgttgataa    6840
atacagatcc atcgtgttga tcattgaatc gtcacttgga gctcactcat cggacttaaa    6900
aaaaaaacct taacaaccta gtgacttaaa taaaacttt gaatagttta ctgactattt    6960
tgtaactttt taaagttaag tgactaaaac gtgaacatac taatagttta gtgacctcgg    7020
ttgattttac ccaaaaaatt attattcaac ctctcgtcct ctccttttta caccttttta    7080
ttatttttta tttttctct ttactttgtt ttttagcta tttccagcga ctactaaaca    7140
aaataaaaat tagcccagga caggaggatc tctcagctac ttttctctc aaaatttctc    7200 caattagctc tgtaattttc tattttgttt ctctttattt tagattttt ttggtccgtg    7260 ttaatcttcg ttgaaggcga tctagctttg atttgaattt cattttttt cttttttcct    7320 tttaagatac ttttttgttt gtttagggt ttaggcgtca tcaaatctat atggctggtt    7380
atgacaagaa tatgtatgtt agtatcccag tcaacgcaag gctcgaaatg gatgtgaaat    7440
ctaaggaagc taaaattgaa ttcgaagttg aacaacagca acaagattct cgtttagtgc    7500
acattactag cactccctac acctcaagaa gtgatctttt ttcctttag tataaaatag    7560 ttaagtgatg ttaattagta tgattataat aatatagttg ttataattgt gaaaaaataa    7620
tttataaata tattgtttac ataaacaaca tagtaatgta aaaaaatatg acaagtgatg    7680
tgtaagacga agaagataaa agttgagagt aagtatatta tttttaatga atttgatcga    7740
acatgtaaga tgatatacta gcattaatat ttgttttaat cataatagta attctagctg    7800
gtttgatgaa ttaaatatca atgataaaat actatagtaa aaataagaat aaataaatta    7860
```

```
aaataatatt tttttatgat taatagttta ttatataatt aaatatctat accattacta    7920
aatattttag tttaaaagtt aataaatatt ttgttagaaa ttccaatctg cttgtaattt    7980
atcaataaac aaaatattaa ataacaagct aaagtaacaa ataatatcaa actaatagaa    8040
acagtaatct aatgtaacaa aacataatct aatgctaata taacaaagcg caagatctat    8100
cattttatat agtattattt tcaatcaaca ttcttattaa tttctaaata atacttgtag    8160
ttttattaac ttctaaatgg attgactatt aattaaatga attagtcgaa catgaataaa    8220
caaggtaaca tgatagatca tgtcattgtg ttatcattga tcttacattt ggattgtcac    8280
ttcttgaggt gtagggagtg ctagtaatgt gcactaaacg agaatcttgt tgctgttgtt    8340
caacttcgaa ttcaatttta gcttccttag atttcacatc catttcgagc cttgcgttga    8400
ctgggatact aacatacata ttcttgtcat aaccagccat atagatttga tgacgatcgt    8460
tcaaacattt ggcaataaag tttcttaaga ttgaatcctg ttgccggtct tgcgatgatt    8520
atcatataat ttctgttgaa ttacgttaag catgtaatat ttaacatgta atgcatgacg    8580
ttatttatga gatgggtttt tatgattaga gtcccgcaat tatacattta atacgcgata    8640
gaaaacaaaa tatcgcgcgc aaacttggat aaattatcgc gcgcggtgtc atctatgagg    8700
actagatcgg ctcgagggta cccctattta tagttgaggt tcaaggacca aacaataaat    8760
agcccattat ctcaaggaca aaaaaaaaat tatcccatgc cacttttttca aagtcaactt    8820
tagggtgcta aacttgcacc acttggattg tttgccatta aaattgtctg ccattaatca    8880
taatgttaac ataggttacc attgagtacc gaatgagttc ccttaatggc aacattttag    8940
gtactaaaac tcgaaggttc atcgataccg ctttagcggc agctttcggg aggttttttgg    9000
tgaggaagaa accgcagttg ccttgatcgt cttcgattcg agtgcagcta ccatacgctt    9060
cgtcgatcga accgacatgg gttcggacca agtggttcag tttcaaaatg gctcgatgtt    9120
taagccctct tctgttcttt aaaagcaaag aacaacccccc tatacgaaaa agaatattag    9180
ggagcatcat ggacctttct ttgcctacat accaattagg gcttaatgat tccgagctca    9240
caacaatggc gaattggttc ttatatgttt gaaacaaatg gttcacaaga tcaatggcta    9300
taacactcgc acgacaaaaa ggacaacaca aagagagatc aaaaaaaccc gacaccaagg    9360
ggcatcaagt aataaacagc ccccacagct tcaaactaag ttcctttctt tcttttttttg    9420
actttctttc aagggaagaa aggagagaaa gattttatgc tttttttatt ataaaataaa    9480
taaaaaaaca gctggccgcc atggggaggc acttgcttca tctttatctt atgatccttc    9540
ctgataccct tgatgagaatg agaccaaata atgcacttca gaacatgaat tataaggatt    9600
atttgagaat gtcagaggga tatgacaaca agtactttgc caatcctgag gttttcgcag    9660
ctccaggtgg aatcactact ggtattacta tcgttacaaa attgcttggt tggcttggat    9720
tgccattcgc tggtgaaacc ggaatggcat tgaatttttat tcttggattg ctttggccaa    9780
cttctggtaa tccttgggct gaattgatga tattggtgga agaattgatc aatcaaaaga    9840
ttgaggagac cgttaggaac aaggcacttg cagatcttgg aaactcagga agagctcttc    9900
agtcatatct taacgctttc gaagattggc aaaagaatcc aaatattttc agatcaaaag    9960
agcttgttaa ggaaaggttc tctaatgctg aacactcatt gaggactgaa atgtcatcat   10020
tcgcaataag aggttttgag attcctctctt tggctacata cgcccaagct gctaatttgc   10080
atcttttctt gatcaaggat attcaaatct acggtaagga atggggttac acccaagcag   10140
acatcgacct tttctacaga gaacaagttg aatttactaa ggaatataca gagcactgta   10200
```

```
ttaatatcta taatgatgga ttgaaccagc ttaagggatc aaacgctaag cagtggattg    10260
cattcaacag gtttagaagg gaaatgacat tgacagtttt ggacgttgtg gctctttttc    10320
ctaactacga cgtgaggatg tatcctatca aaactaccac agagttgacc aggacaatat    10380
atactgatcc tttgggttat actaagaccg gttcatcatc tactccacca tggtgcaatt    10440
atggatcttc ttttcatac attgagtcag ttgctattcc tgctccttca ttggtgaaat    10500
ggctttctca aatagaaatc tactcaaagt ctgctagggc cacacctcaa tctgctgact    10560
actgggctgg tcataccatt acataccatt actcaggtga tgatggacaa gcagttgcta    10620
actatggtga caggactaat ccagtgatag tgaataggta caacttcgaa caggctgata    10680
tatacagggt ttcatcatct gttgcttcat caaccacctc tggagttaag ttgcttacta    10740
ctaaggctat atttgatgga atatcaacta acaacggact tgtttcatac atgtacgaaa    10800
aactttcaaa tttttttaat gagcttaaag acaccatcac tgaacttcct gtgcaaattt    10860
cttctcctcc aacatacggt gacgcagaac agtactctca cagattgtct tatgtgtcta    10920
atgctcctac agagtactct tctggaggac accttattct tggacttata cctgtgcttg    10980
gttggaccca tacctcactt acccaaaacca accaaatcca ctcagattct atcacacaaa    11040
ttcctgctgt gaaggcaaat tctgtgtctt cttatgtgac tgttgaaaaa ggtacaggtt    11100
ttactggagg agatttggtt aaatttcta caggtttcat gtctactggt attcaattca    11160
atttgaaaat tgaggagggt aaaagataca gaattagaat tagatatgca gccgatgtta    11220
atgccactct ttctgcattg ggtcttaacg atgccttcat taacattgag tctacaatgt    11280
cacaggacac tcctctttaaa tataacgatt ttcagtatgc cgaggccgat aaaacagttc    11340
atttgtataa cccaagattc tcattgtatt tggagaactc tgaccagtct ggtaaatcta    11400
tctatattga taggatcgag ttcatcccag ttgataacgg atctttgaac caccatcatc    11460
atcatcatta acgatcgttc aaacatttgg caataaagtt tcttaagatt gaatcctgtt    11520
gccggtcttg cgatgattat catataattt ctgttgaatt acgttaagca tgtaatattt    11580
aacatgtaat gcatgacgtt atttatgaga tgggtttta tgattagagt cccgcaatta    11640
tacatttaat acgcgataga aaacaaaata tcgcgcgcaa acttggataa attatcgcgc    11700
gcggtgtcat ctatgaggac tagatcgggg taccggatcc tcgaggttcc ctttagtgag    11760
ggttaattgc gagcttggcg taatcatggt catagctgtt tcctgtgtga aattgttatc    11820
cgctcacaat tccacacaac atacgagccg gaagcataaa gtgtaaagcc tggggtgcct    11880
aatgagtgag ctaactcaca ttaattgcgt tgcgctcact gcccgctttc cagtcgggaa    11940
acctgtcgtg ccagctgcat taatgaatcg gccaacgcgc ggggagaggc ggtttgcgta    12000
ttgggcgctc ttccgcttcc tcgctcactg actcgctgcg ctcggtcgtt cggctgcggc    12060
gagcggtatc agctcactca aaggcggtaa tacggttatc cacagaatca ggggataacg    12120
caggaaagaa catgtgagca aaaggccagc aaaaggccag gaaccgtaaa aaggccgcgt    12180
tgctggcgtt tttccatagg ctccgccccc ctgacgagca tcacaaaaat cgacgctcaa    12240
gtcagaggtg gcgaaacccg acaggactat aaagatacca ggcgtttccc cctggaagct    12300
ccctcgtgcg ctctcctgtt ccgaccctgc cgcttaccgg atacctgtcc gcctttctcc    12360
cttcgggaag cgtggcgctt tctcatagct cacgctgtag gtatctcagt tcggtgtagg    12420
tcgttcgctc caagctgggc tgtgtgcacg aaccccccgt tcagcccgac cgctgcgcct    12480
tatccggtaa ctatcgtctt gagtccaacc cggtaagaca cgacttatcg ccactggcag    12540
cagccactgg taacaggatt agcagagcga ggtatgtagg cggtgctaca gagttcttga    12600
```

```
agtggtggcc taactacggc tacactagaa gaacagtatt tggtatctgc gctctgctga    12660
agccagttac cttcggaaaa agagttggta gctcttgatc cggcaaacaa accaccgctg    12720
gtagcggtgg ttttttttgtt tgcaagcagc agattacgcg cagaaaaaaa ggatctcaag   12780
aagatccttt gatcttttct acggggtctg acgctcagtg gaacgaaaac tcacgttaag    12840
ggattttggt catgagatta tcaaaaagga tcttcaccta gatccttttta aattaaaaat   12900
gaagttttaa atcaatctaa agtatatatg agtaaacttg gtctgacagt taccaatgct    12960
taatcagtga ggcacctatc tcagcgatct gtctatttcg ttcatccata gttgcctgac    13020
tccccgtcgt gtagataact acgatacggg agggcttacc atctggcccc agtgctgcaa    13080
tgataccgcg agacccacgc tcaccggctc cagatttatc agcaataaac cagccagccg    13140
gaagggccga gcgcagaagt ggtcctgcaa ctttatccgc ctccatccag tctattaatt    13200
gttgccggga agctagagta agtagttcgc cagttaatag tttgcgcaac gttgttgcca    13260
ttgctacagg catcgtggtg tcacgctcgt cgtttggtat ggcttcattc agctccggtt    13320
cccaacgatc aaggcgagtt acatgatccc ccatgttgtg caaaaaagcg gttagctcct    13380
tcggtcctcc gatcgttgtc agaagtaagt tggccgcagt gttatcactc atggttatgg    13440
cagcactgca taattctctt actgtcatgc catccgtaag atgcttttct gtgactggtg    13500
agtactcaac caagtcattc tgagaatagt gtatgcggcg accgagttgc tcttgcccgg    13560
cgtcaatacg ggataatacc gcgccacata gcagaacttt aaaagtgctc atcattggaa    13620
aacgttcttc ggggcgaaaa ctctcaagga tcttaccgct gttgagatcc agttcgatgt    13680
aacccactcg tgcacccaac tgatcttcag catcttttac tttcaccagc gtttctgggt    13740
gagcaaaaac aggaaggcaa aatgccgcaa aaagggaat aagggcgaca cggaaatgtt     13800
gaatactcat actcttcctt tttcaatatt attgaagcat ttatcagggt tattgtctca    13860
tgagcggata catatttgaa tgtatttaga aaaataaaca aatagggggtt ccgcgcacat   13920
ttccccgaaa agtgccac                                                  13938
```

METHOD AND COMPOSITIONS FOR CONTROLLING PEST INSECTS ON PLANTS BY SILENCING GENES OF THE CHITIN SYNTHASE AND OF THE VITELLOGENIN FAMILY, AS WELL AS ALTERNATIVELY BY EXPRESSING THE GENE OF A CRY TOXIN

CROSS REFERENCE TO RELATED APPLICATIONS

This application is a National Stage of International Application No. PCT/BR2014/050049 filed on Dec. 18, 2014, which claims priority from Brazilian Patent Application No. BR 102013032649.6 filed on Dec. 18, 2013, the contents of all of which are incorporated herein by reference in their entirety.

FIELD OF THE INVENTION

The present invention relates to the field of controlling insects-pest that attach crops, especially cotton-plants, by using specific gen constructs containing dsRNA of Chitin Synthase 2 of the cotton-weevil, dsRNA of Vitellogenin of cotton-weevil and alternatively toxin Cry8ka5, expressed on cotton-plants.

BACKGROUND OF THE INVENTION

Agriculture is nowadays one of the most important bases of the economy of developing countries. In Brazil, the main crops that support the economy are: cotton-plant, soybeans, coffee-beans, sugar-cane, among others (DANTAS, R. J. E. S.; LIMA, M. F. S.; WOSCH, L. F. O. et al. Conhecendo o Brasil em números. In: DEPLA, editor. Brasília, pp. 16. 2010). These crops are of great social and economic importance, contributing relevantly to the Brazilian Gross Domestic Product (GDP), besides the direct generation of jobs, be it in the production chain or in derived products (AVELAR, S. O. C.; VILELA, P. S. Evolução do número de pessoas ocupadas na agropecuária brasileira no período de 1990 a 2004. Revista Política Agrícola: 4-8. 2006).

However, most of these crops, like cotton-plant, are grown in large areas in a single-culture system, which favors the incidence of pests, the losses causes by insects reaching about 60% of the production (Abrapa. Relatório do Biênio 2008/2010. In: Abrapa, editor. 2010). The most widely used form of controlling pests on cotton plants is the chemical control, which increases the production costs substantially, besides causing damage to nature and health of the field workers. In the face of this situation, various studies have been carried out aiming at the development of more efficient control strategies (DIAS, S. C.; da SILVA, M. C. M.; TEIXEIRA, F. R. et al., Investigation of insecticidal activity of rye alpha-amylase inhibitor gene expressed in transgenic tobacco (*Nicotiana tabacum*) toward cotton boll weevil (*Anthonomus grandis*). Pesticide Biochemistry and Physiology, 98: 39-44. 2010). With the advent of the so-called Manejo Integrado de Pragas (MIP) (Integrated Pest Management), various strategies have been studied and used in harmony with success, gradually modifying the view of agriculturists with respect to the indiscriminate use of insecticides. Within this context, the use of biotechnological tools and the transformation of plants emerged as a promising strategy for obtaining more productive and resistant cultivars, besides causing less damage to the environment and reducing production costs (GALLO, D.; NAKANO, O.; SILVEIRA-NETO S. et al., Entomologia Agrícola. Piracicaba: FEALQ. 649 p. 2002).

The prospection for new genes and proteins, together with the production of transgenic plans is a promising strategy for the control of pest-insects in various stages of their life cycle. For example, genetically modified plants containing resistant genes, protein toxins like Cry de *Bacillus thuringiensis* (MAHON, R. J.; OLSEN, K. M. Limited survival of a Cry2Ab-resistant strain of *Helicoverpa armigera* (Lepidoptera: Noctuidae) on Bollgard II. Journal of Economic Entomology, 102: 708-716. 2009), or containing interfering RNA (BAUM, J. A.; BOGAERT, T.; CLINTON, W. et al., Control of coleopteran insect pests through RNA interference. Nature Biotechnology, 25: 1322-1326. 2007) may be used as new tools for controlling pests.

The growing use of insect-resistance transgenic plants has shown a number of economic, environmental benefits, as well as benefits for human health (CHRISTOU, P.; CAPELL, T.; KOHLI, A. et al., Recent developments and future prospects in insect pest control in transgenic crops. Trends in Plant Science, 11: 302-308. 2006). The main transgenic varieties with well-known entomotoxic effects on cotton-plant express toxins Cry de *Bacillus thuringiensis*. But at present special focus has been put on the use of the mechanism of interfering RNA for both clarifying gene functions and controlling pests by gene silencing. (BAUM, J. A.; BOGAERT, T.; CLINTON, W. et al., Control of coleopteran insect pests through RNA interference. Nature Biotechnology, 25: 1322-1326. 2007).

The mechanism of interfering RNA (RNAi) is a process that occurs naturally in the cells and in various eukaryotic organism. It was first described on plants, called post-transcriptional gene silencing, or PTGS (JORGENSEN, R. A.; CLUSTER, P. D.; ENGLISH, J., et al., Chalcone synthase cosuppression phenotypes in petunia flowers: comparison of sense vs. antisense constructs and single-copy vs. complex T-DNA sequences. Plant Molecular Biology, 31: 957-973. 1996). However, the first description of gene silencing on animals, as well as the better understanding thereof, was achieve in *Caenorhabditis elegans*, a free-live nematode and model organism in these studies (FIRE, A. RNA-triggered gene silencing. Trends in Genetics, 15: 358-363. 1999). In plants, it was initially believed that the mechanism of RNAi was used as defense against effects of the movement of transposons, that is, against infection by virus (VOINNET, O. RNA silencing: small RNAs as ubiquitous regulators of gene expression. Current Opinion in Plant Biology, 5: 444-451. 2002). However, at present it is known that this process participates in an integral manner in the regulation of the gene expression in various plants and other eukaryotes (LILLEY, C. J.; BAKHETIA, M.; CHARLTON, W. L. et al., Recent progress in the development of RNA interference for plant parasitic nematodes. Molecular Plant Pathology, 8. 2007).

In this context, RNAi has been proving to be a promising tool in helping to control pests. Its action mechanism is based chiefly on introducing a double-stranded RNA (dsRNA) into a garget organism, generally by ingestion (FIRE, A. RNA-triggered gene silencing. Trends in Genetics, 15: 358-363. 1999). This double-stranded RNA starts a post-transcriptional gene silencing process by degrading homologous mRNAs, causing a decrease in the synthesis of the corresponding protein (MEISTER, G.; TUSCHL, T. Mechanisms of gene silencing by double-stranded RNA. Nature, 431: 343-349, 2004), making the survival of the organism difficult, or even killing it.

This technique has already been used successfully for obtaining pest-resistant plants, as is the case of *Nicotiana tabacum* (YADAV, B. C.; VELUTHAMBI, K.; SUBRAMANIAM, K. Host-generated double stranded RNA induces RNAi in plant-parasitic nematodes and protects the host from infection. Molecular and Biochemical Parasitology, 148: 219-222. 2006), *Arabidopsis thaliana* (HUANG, G.; ALLEN, R.; DAVIS, E. L. et al., Engineering broad root-knot resistance in transgenic plants by RNAi silencing of a conserved and essential root-knot nematode parasitism gene. Proceedings of the National Academy of Sciences USA, 103: 14302-14306. 2006) e *Glycine max* (IBRAHIM, H. M.; ALKHAROUF, N. W., MEYER, S. L. et al., Post-transcriptional gene silencing of root-knot nematode in transformed soybean roots. Experimental Parasothology, 127: 90-99. 2011), presenting resistance above 90% to the phytoparasite *Meloidogyne incognita*.

Since the initial description of this technique, it has become a valuable tool for the functional genomics of insects, in particular with *Drosophila melanogaster* (XIE, X.; DUBROVSKAYA, V. A.; DUBROVSKY, E. B. RNAi knockdown of dRNaseZ, the *Drosophila* homolog of ELAC2, impairs growth of mitotic and endoreplicating tissues. Insect Biochemistry and Molecular Biology, 41: 167-177. 2011; KENNERDELL, J. R.; CARTHEW, R. W. Heritable gene silencing in *Drosophila* using double-stranded RNA. Nature Biotechnology, 18: 896-898. 2000). The most widely used methodology in most of the studies with insects is microinjection of dsRNA in the hemolymph of the insect, which is inviable for practical purposes, since it does not correspond to what happens in nature. However, a number of studies have been made with a view to incorporating the dsRNA into the artificial diet or water of the insect in order to assess the effects of silencing through ingestion of the double strand of RNA (ZHANG, J. Z.; LIU, X. J.; ZHANG, J. Q. et al., Silencing of two alternative splicing-derived mRNA variants of chitin synthase 1 gene by RNAi is lethal to the oriental migratory locust, *Locusta migratoria* manilensis (Meyen). Insect Biochemistry and Molecular Biology, 40: 824-833. 2010; ZHU, F.; XU, J. J., PALLI, R. et al., Ingested RNA interference for managing the populations of the Colorado potato beetle, *Leptinotarsa decemlineata*. Pest Management Science, 67: 175-182. 2011).

One of the main targets of the researches associated to the control of insect/pests is the perspective of understanding and interfering with the vital processes of the insect. Within this perspective the reproduction is the process by which the populations tend to grow and settle in the agricultural system. In this context, it is important to carry out researches that aim at interfering with the biochemistry and physiology of the reproduction, for the control of pest-insects, by interrupting the population growth.

Vitellogenin is a female-specific glycoprotein, precursor of the vitellus and produced by all the oviparous animals. It is generally synthesized in large amounts directly before the deposition of the vitellus, and it is of paramount importance in the reproduction (BYRNE, B. M.; GRUBER, M.; Aft G. The evolution of egg yolk proteins. Progress in Biophysics and Molecular Biology, 53: 33-69. 1989).

In insects, the larger part of the nutrients for oocytes is vitellogenin, usually produced out of the ovary, in the fatty bodies, secreted in the hemolymph, and recognized specifically by developing oocytes and deposited in the cytoplasm in its stock form, the vitellus (KLOWDEN, M. J. Physiological Systems in Insects. Moscow: Elsevier. 688 p. 2007).

An alternative use of vitellogenin is reported in working bees that do not produce eggs, even if they are females. The vitellogenin which they produce binds their hypopharyngeal glands and produce for feeding the future queen-bee. Used as a versatile stock protein which can be adopted in various metabolic processes, vitellogenin can supplement the metabolism of worker bees and the synthesis of royal jelly when the sources of pollen are scarce. Other insects can produce trophic eggs strengthened with vitellogenin and lay eggs only for consumption by the offspring (KLOWDEN, M. J. Physiological Systems in Insects. Moscow: Elsevier. 688 p. 2007).

Considering that cotton-boll weevil exhibits only a copy of the gen that encodes this protein (TREWITT, P. M.; HEILMANN, L. J.; DEGRUGGILLIER, S. S. et al., The boll weevil vitellogenin gene: nucleotide sequence, structure, and evolutionary relationship to nematode and vertebrate vitellogenin genes. Journal of Molecular Evolution, 34: 478-492. 1992), it becomes a promising target for gene silencing aimed at the control of this insect, since it is not possible to have a compensation effect, which might occur if there were another copy of this gene.

Another important target gene to be used in the strategy of the RNAi, especially to combat pest-insects is the chitin gene. Chitin, a linear polysaccharide formed by residues of N-acetyl-D-glycosamine United by $\beta$ (1-4) bonds, is widely spread among the insects, which use this versatile biopolymer in various anatomic structures. The two main extracellular structures where deposition of chitin takes place are the cuticle that involves the epidermis and the peritrophic membrane that covers the middle intestines. (MUTH-UKRISHNAN, S., et al., Chitin Metabolism in Insects. In Insect Molecular Biology and Biochemistry, 1 ed.; Gilbert, L. I., Ed. Elsevier: London, pp 193-225. 2012).

The peritrophic membrane is a functional structure that covers the middle intestine of insects. The main functions attributed to this membrane are that of mechanical protection against injury of the cells of the middle intestine (WIGGLESWORTH, V., The principles of insect physiology. 7 ed.; Chapman and Hall: London, Vol. p 827. 1972), a physical barrier against microorganisms (PETERS, W., Peritrophic membranes. Springer-Verlag New York, Vol. 1992), a selective barrier for digestive enzymes and digestion products (DAY, M. F.; WATERHOUSE, D. F., Functions of the alimentary system. John Wiley: New York, Vol. p 299-310. 1953) and actuation on the mechanism of recycling digestive enzymes, a phenomenon known as ectoendoperitrophic circulation (TERRA, W. R., Physiology and Biochemistry of Insect Digestion—an Evolutionary Perspective. Brazilian Journal of Medical and Biological Research, v. 21, n. 4. p. 675-734. 1988; TERRA, W. R.; FERREIRA, C., Insect Digestive Enzymes—Properties, Compartmentalization and Function. Comparative Biochemistry and Physiology Biochemistry & Molecular Biology, v. 109, n. 1. p. 1-62. 1994; TERRA, W. R., The origin and functions of the insect peritrophic membrane and peritrophic gel. Archives of Insect Biochemistry and Physiology, v. 47, n. 2. p. 47-61, 2001).

The cuticle of insects or exoskeleton is a multifunctional structure that serves as physical support, as well as gives the their form, enables them to move about, makes the body impermeable, and has a number of localized mechanical specializations, such as a high degree of adherence, resistance to wear and diffusion control. In this structure, its mechanical properties are attributed to its main constituent, namely: chitin (VINCENT, J. F., et al., Design and mechanical properties of insect cuticle. Arthropod Struct Dev, v. 33, n. 3. p. 187-199. 2004).

The synthesis and deposition of chitin on the cuticle and on the peritrophic membrane comprise a sequential number of complex biochemical, biophysical, intracellular and extracellular transformations, some of which are still little known (MOUSSIAN, B., et al., Assembly of the *Drosophila* larval exoskeleton requires controlled secretion and shaping of the apical plasma membrane. Matrix Biol, v. 26, n. 5. p. 337-347. 2007). Since the biosynthetic pathway of chitin is absent in plants and vertebrate animals, it is one of the main targets for the development of insecticides, since 1970 (VERLOOP, A., et al., Benzoylphenyl Ureas—A New Group of Larvicides Interfering with Chitin Deposition. In Pesticide Chemistry in the 20th Century, AMERICAN CHEMICAL SOCIETY: Vol. 37, pp 237-270. 1977). Among the enzymes involved in the synthesis of chitin in insects, a special approach has been given to the last step of the pathway which is mediated by the enzyme chitin synthase (EC 2.4.1.16), which catalyzes the polymerization of chitin from activated monomers of UDP-N-acetylglycosamine (MERZENDORFER, H., The cellular basis of chitin synthesis in fungi and insects: common principles and differences. Eur J Cell Biol, v. 90, n. 9. p. 759-769. 2011).

The interruption or decrease in the synthesis of enzymes that participate in the biosynthesis of constituents of the cuticle and of the peritrophic membrane of insects by means of the technology of RNAi is like a specific form of control of pest insects.

Chitin synthase A (or type 1) in insects is the main enzyme involved in the biosynthesis of chitin of the cuticle and of the trachea. However, chitin synthase B (or type 2) in insects is the main enzyme involved in the biosynthesis of chitin of the peritrophic membrane, both chitin synthases of insects have been studies as ideal targets for the development of strategies for the control of pest insects.

For the research on technologies aimed at providing products for the control of pest insects, it is strategic to have a continuous flow in the obtainment of new insecticidal molecules for application in different molecular strategies with a view to obtain genetically modified plants that are resistant to the target insect. These actions help to obtain elite events to aid in the control in a sustainable manner, since insects are capable of evolving and adapting themselves rapidly to the new conditions, managing to inactivate natural defense mechanisms or mechanisms inserted into the plants "artificially". At present, genes that encode entomotoxic toxins Cry of *Bacillus thuringiensis* (Bt) in transgenically modified plants sold for control of pest insects are widely used. However, there are a few reports of break of resistance, by insects that feed on these plants. In this context, the present invention has the characteristic of presenting methods of compositing gene constructs, using a strategy that combines the joint expression of toxicity to the target insect with the silencing of genes essential to the development of cotton-boll weevil, since this strategy makes the development of multiple resistance of the insect difficult, because the action mechanisms of the molecules used are very distinct.

Thus, the present invention uses both a gene construct containing the two ds RNA (Vitelolgenin and Chitin Synthase 2) and a specific gene construct containing toxin Cry8ka5, dsRNA of Chitin Synthase 2 of cotton-boll weevil and dsRNA of Vitellogenin of cotton weevil for expression in cotton plants. These strategies are useful for interrupting the life cycle of cotton boll weevil and trying to dribble the break of resistance. Besides, considering the effective adaptation capability of the insect to insecticidal molecules, the knowledge validated in the present invention presents actives for the Brazilian agriculture, which may be applied either separately or jointly (in pyrimidization strategy) in obtaining sustainable resistance of the plants GM.

SUMMARY OF THE INVENTION

The present invention relates to a method for obtaining cotton plants that are resistant or more tolerant to pest insects. Specifically, the present invention relates to the obtainment of cotton plants that are resistant or more tolerant to cotton-boll weevil (*Anthonomus grandis*).

In an embodiment of the invention, a gene construct is characterized by comprising:
(i) a promoter functional in plant;
(ii) a sense fragment substantially similar to the SEQ ID NO: 1;
(iii) a sense fragment substantially similar to the SEQ ID NO: 2;
(iv) a spacer sequence;
(v) an antisense fragment substantially similar to the SEQ ID NO: 3;
(vi) an antisense fragment substantially similar to the SEQ ID NO: 4;
(vii) a terminator functional in plant; and alternatively
(viii) promoter functional in plant;
(ix) a nucleotide sequence substantially similar to the SEQ ID NO 5;
(x) a terminator functional in plant.

In another embodiment of the invention, one describes a gene construct characterized by comprising:
(i) a promoter functional in plant;
(ii) a sense fragment substantially similar to the SEQ ID NO: 1;
(iii) a spacer sequence;
(iv) an antisense fragment substantially similar to the SEQ ID NO: 3;
(v) a terminator functional in plant;
(vi) a promoter functional in plant;
(vii) a nucleotide sequence substantially similar to the SEQ ID NO 5; e
(viii) a terminator functional in plant.

In another embodiment of the invention, one describes a gene construct characterized by comprising:
(i) a promoter functional in plant;
(ii) a sense fragment substantially similar to the SEQ ID NO: 2;
(iii) a spacer sequence;
(iv) an antisense fragment substantially similar to the SEQ ID NO: 4;
(v) a terminator functional in plant;
(vi) a promoter functional in plant;
(vii) a nucleotide sequence substantially similar to the SEQ ID NO 5; and
(viii) a terminator functional in plant.

The invention further describes a method for producing transgenic plants capable of producing dsRNA of interest, so that the pest insect, upon feeding on these plants, will have the target gene silenced, characterized by comprising the steps of:
I) providing a gen construct characterized by comprising:
(i) a promoter functional in plant;
(ii) a sense fragment substantially similar to the SEQ ID NO: 1;

(iii) a sense fragment substantially similar to the SEQ ID NO: 2;
(iv) a spacer sequence;
(v) an antisense fragment substantially similar to the SEQ ID NO: 3;
(vi) an antisense fragment substantially similar to the SEQ ID NO: 4;
(vii) a terminator functional in plant; and alternatively
(viii) a promoter functional in plant;
(ix) a nucleotide sequence substantially similar to the SEQ ID NO 5;
(x) a terminator functional in plant.
II) inserting the molecule obtained in "I" into a plant cell or cells to produce a transgenic cell or transgenic cells; and
III) growing or regenerating transgenic plant from the transgenic cell or cells.

The invention also describes a method to produce transgenic plants capable of producing dsRNA of interest, so that the pest insect, upon feeding on these plants, will have the garget gen silenced, characterized by comprising the steps of:
I) providing a gene construct characterized by comprising:
(i) a promoter functional in plant;
(ii) a sense fragment substantially similar to the SEQ ID NO: 1;
(iii) a spacer sequence;
(iv) an antisense fragment substantially similar to the SEQ ID NO: 3;
(v) a terminator functional in plant;
(vi) a promoter functional in plant;
(vii) a nucleotide sequence substantially similar to the SEQ ID NO 5; e
(viii) a terminator functional in plan;
II) inserting the molecule obtained in "I" into a plant cell or cells to produce a transgenic cell or transgenic cells; and
III) growing or regenerating a transgenic plant from the transgenic cell or cells.

The invention also describes a method for producing transgenic plants capable of producing dsRNA of interest, so that the pest insect, upon feeding on these plants, will have the target gene silenced, characterized by comprising the steps of:
I) providing a gene construct characterized by comprising:
(i) a promoter functional in plant;
(ii) a sense fragment substantially similar to the SEQ ID NO: 2;
(iii) a spacer sequence;
(iv) an antisense fragment substantially similar to the SEQ ID NO: 4;
(v) a terminator functional in plant;
(vi) a promoter functional in plant;
(vii) a nucleotide sequence substantially similar to the SEQ ID NO 5; e
(viii) a terminator functional in plant;
II) inserting the molecule obtained in "I" into a plant cell or cells to produce a transgenic cell or transgenic cells; and
III) growing or regenerating transgenic plant from the transgenic cell or cells.

Another embodiment of the invention is a method for controlling pest insects, characterized in that it comprises making available, in their diet, an agent comprising a double-stranded ribonucleic acid sequence produced from the gene construct characterized by comprising:
(i) a promoter functional in plant;
(ii) a sense fragment substantially similar to the SEQ ID NO: 1;
(iii) a sense fragment substantially similar to the SEQ ID NO: 2;
(iv) a spacer sequence;
(v) an antisense fragment substantially similar to the SEQ ID NO: 3;
(vi) an antisense fragment substantially similar to the SEQ ID NO: 4;
(vii) a terminator functional in plant; and alternatively
(viii) a promoter functional in plant;
(ix) a nucleotide sequence substantially similar to the SEQ ID NO 5;
(x) a terminator functional in plant.

The invention also relates to a method for controlling pest plants, in that it makes available, their diet, an agent comprising a double-stranded ribonucleotide sequence produced from the gen construct characterized by comprising:
(i) a functional promotor in plant;
(ii) a sense fragment substantially similar to the SEQ ID NO: 1;
(iii) a spacer sequence;
(iv) an antisense fragment substantially similar to the SEQ ID NO: 3;
(v) a terminator functional in plant;
(vi) a promoter functional in plant;
(vii) a nucleotide sequence substantially similar to the SEQ ID NO 5; and
(viii) a terminator functional in plant.

The invention also provides a method for controlling pest insects characterized in that it comprises making available, in their diet, an agent comprising a double-stranded ribonucleotide sequence produced from the gen construct characterized by comprising:
(i) a promoter functional in plant;
(ii) a sense fragment substantially similar to the SEQ ID NO: 2;
(iii) a spacer sequence;
(iv) an antisense fragment substantially similar to the SEQ ID NO: 4;
(v) a terminator functional in plant;
(vi) a promoter functional in plant;
(vii) a nucleotide sequence substantially similar to the SEQ ID NO 5; and
(viii) a terminator functional in plant.

Another embodiment of the invention is a method for improving the yield of cultivated plants, subject to infestation by pest insects, characterized by comprising the steps of:
I. Obtaining a transgenic plant by introducing a genic construct comprising:
(i) a promoter functional in plant;
(ii) a sense fragment substantially similar to the SEQ ID NO: 1;
(iii) a sense fragment substantially similar to the SEQ ID NO: 2;
(iv) a spacer sequence;
(v) an antisense fragment substantially similar to the SEQ ID NO: 3;
(vi) an antisense fragment substantially similar to the SEQ ID NO: 4;
(vii) a terminator functional in plant; and alternatively
(viii) a promoter functional in plant;
(ix) a nucleotide sequence substantially similar to the SEQ ID NO 5;
(x) a terminator functional in plant;
II. growing the plant obtained in "I", so that it will express the sequences of interest of said gene construct, in order for the products of this expression to produce or suppress the population of the pest insects.

A further embodiment of the invention is a method to improve the yield of cultivated plants, subject to infestation by pest insects, characterized by comprising the steps of:
I. Obtaining a transgenic plant by introducing a gene construct comprising:
(i) a promoter functional in plant;
(ii) a sense fragment substantially similar to the SEQ ID NO: 1;
(iii) a spacer sequence;
(iv) an antisense fragment substantially similar to the SEQ ID NO: 3;
(v) a terminator functional in plant;
(vi) a promoter functional in plant;
(vii) a nucleotide sequence substantially similar to the SEQ ID NO 5; e
(viii) a terminator functional in plant;
II. growing a plant obtained in "I", so that it will express the sequences of interest of said gen construct, in order for the products of this expression to produce or suppress the population of the pest insects.

Another embodiment of the invention is a method for improving the yield of cultivated plants, subject to infestation by pest insects, characterized by comprising the steps of:
I. obtaining a transgenic plant by introducing a gene construct comprising:
(i) a promoter functional in plant;
(ii) a sense fragment substantially similar to the SEQ ID NO: 2;
(iii) a spacer sequence;
(iv) an antisense fragment substantially similar to the SEQ ID NO: 4;
(v) a terminator functional in plant;
(vi) a promoter functional in plant;
(vii) a nucleotide sequence substantially similar to the SEQ ID NO 5; and
(viii) a terminator functional in plant.
II. Cultivating a plant obtained in "I", so that it will express the sequences of interest of said gen construction, in order for the products of this expression to produce or suppress the population of pest insects.

The invention further describes a method of producing a product characterized in that it comprises obtaining a plant containing the gen construct of the present invention, or a part thereof, and preparing its from the whole or a part of this plant, in order for it to be made available in the diet of insects of interest, with a view to reduce or suppress the population thereof.

The present invention further provides nucleic acid primers comprising a first and a second nucleic acid molecule capable of amplifying a gene construct of the present invention.

It is a further feature of the present invention to provide a kit for identifying a nucleic acid molecule of a biologic sample, characterized by comprising a first and a second nucleic acid primer, where these are capable of amplifying a molecule substantially similar to the SEQ ID No 7 or SEQ ID NO 8 or SEQ ID NO 19 or SEQ ID NO 20 or a fragment thereof.

Another objective of the present invention is to provide a method for identifying a plant containing the gene construct of the present invention, characterized by comprising the following steps:
a. forming a mixture comprising a biologic sample containing plant DNA and a first and a second nucleic acid primer capable of amplifying a nucleic acid molecule substantially similar to the SEQ ID No 7 or SEQ ID NO 8 or SEQ ID NO 19 or SEQ ID NO 20 or a fragment thereof;
b. reacting the mixture under conditions that enable the first and the second primers to amplify a nucleic acid molecule substantially similar to the SEQ ID No 7 or SEQ ID NO 8 or SEQ ID NO 19 or SEQ ID NO 20 or a fragment thereof; and
c. detecting the presence of an amplified fragment of a nucleic acid molecule substantially similar to the SEQ ID No 7 or SEQ ID NO 8 or SEQ ID NO 19 or SEQ ID NO 20 or a fragment thereof, where the presence of the specific nucleic acid molecule in the plant indicates that the latter is an event of genetically modified plant.

It is a further object of the invention to provide a method of identifying a plant containing any one of the gene constructions of the present invention, characterized by comprising the following steps:
a. forming a mixture comprising a biologic sample containing a plant DNA and a nucleic acid molecule probe capable of hybridizing a nucleic acid molecule substantially similar to the SEQ ID No 7 or SEQ ID NO 8 or SEQ ID No 19 or SEQ ID NO 20 or a fragment thereof;
b. reacting the mixture under conditions that enable the nucleic acid molecule probe to hybridize a nucleic acid molecule substantially similar to the SEQ ID No 7 or SEQ ID NO 8 or SEQ ID No 19 or SEQ ID NO 20 or a fragment thereof; and
c. detecting the hybridization of the probe to the DNA, where the presence of hybridization of the nucleic acid molecule probe to the plant DNA Another objective of the present invention is to provide a method of reproducing a plant that is resistant to pest insects, characterized by comprising the following steps:
a. crossing a plant comprising a nucleic acid molecule substantially similar to the SEQ ID NO 7 or SEQ ID NO 8 or SEQ ID NO 19 or SEQ ID NO 20 or a fragment thereof with a second plant;
b. obtaining seed from the crossing of step (a);
c. obtaining a DNA sample of the seed embryo; and
d. detecting the presence of a nucleic acid molecule substantially similar to the SEQ ID NO 7 or SEQ ID NO 8 or SEQ ID NO 19 or SEQ ID NO 20 or a fragment thereof, where the presence thereof indicates that the seed is capable of producing a plant resistant to the pest insect.

The invention also describes a method for growing a plant, characterized by comprising the following steps:
a. providing seed or seedling comprising a nucleic acid molecule substantially similar to the SEQ ID No 7 or SEQ ID NO 8 or SEQ ID NO 19 or SEQ ID NO 20 or a fragment thereof;
b. planting or sewing the material obtained in steps (a) in a substrate, soil or environment suitable to adequate germination or sprouting and development, aiming at vegetable production, the assembly becoming a cultivation system where populations of pest insects are controlled.

The invention also relates to transformation vectors and expression, transgenic cells and plants, methods for expressing the molecules of the present invention in these plants, as well as the use of these molecules in controlling pest insects.

DETAILED DESCRIPTION OF THE INVENTION

Figure 1:
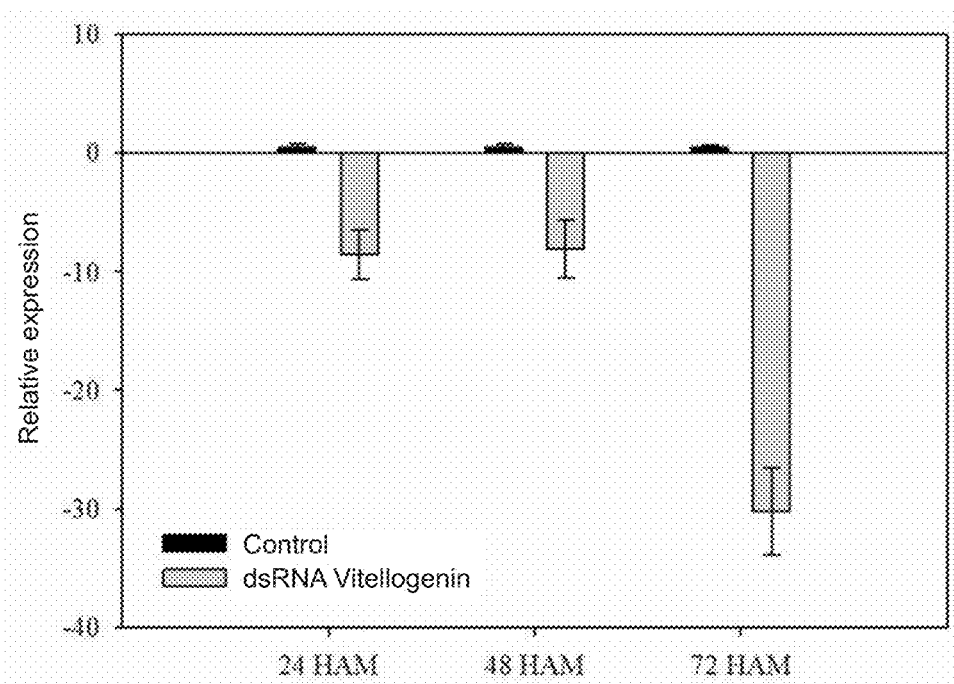
FIG. 1: Analysis of the relative expression of transcripts of Vitellogenin 24, 48 and 72 hours after microinjection (HAM) of dsRNA molecules, using GAPDH and beta-actin as reference genes. The control fragment consisted of cDNA synthesized from RNA from females microinjected with doped H2O. In the treatment of microinjection of dsRNA of Vitellogenin, 500 ng de dsRNA were injected.

The present invention describes methods and compositions for controlling pests, especially cotton pests. For example, the present invention provides recombinant DNA Technologies to repress or inhibit post-transcriptionally the expression of target sequences in the cell of a pest. This effect is achieved after feeding to one or more pests double-stranded RNA or fragments of RNA (miRNA or siRNA) transcribed from the whole or a part of a target encoding sequence, thus controlling the infestation. As a result, the present invention relates to specific sequences of inhibition of the expression. of coding sequences, using double-stranded RNA (dsRNA), including small interfering RNA i (siRNA), to reach the intended levels of pest control.

The present invention provides a method for inhibiting the expression of target genes in coleopteran. In certain embodiments, the method comprises modulating or inhibiting the expression of one or more target genes of coleoptera, preventing the development, reproduction and/or infectivity and possible results in the death of the insect. More specifically, the present invention relates to the inhibition of the gene of the Family of chitin synthase and/or the gene of vitellogenin in coleopteran, resulting in the interruption of the development and malformation of larva and adult insect, and may result in the death of the insect. The method comprises introducing double-stranded RNA (dsRNA) in partial form, stabilized, including its modified forms, such as small interfering RNA (siRNA), into the cells or into an extracellular environment, such as the middle intestine, into coleopteran in which the dsRNA gets into the cells and inhibits the expression of at least one or more target genes, and where the inhibition exerts a deleterious effect on the pest. The methods and compositions associated may be used to limit or eliminate infestation of coleoptera or in any pest host, symbiont pest, or environment in which the pest is present by means of one or more compositions that comprise the dsRNA molecule described herein in the diet of the pests.

Besides the inhibition of the expression of two target genes in coleopteron, the present invention further enables one to obtain cotton plants that are resistant or more tolerant to pest insects by virtue of the possibility of expression of the toxineCry8ka5 (SEQ ID No 5—Cry8ka5 and SEQ ID No 6—Cry8ka5_aa). The present invention further comprises fragments and variants of the sequences described in the present invention related to the toxin Cry8ka5 (SEQ ID No 5—Cry8ka5 and SEQ ID No 6—Cry8ka5_aa). The entomotoxic proteins described are biologically active against some pest insects belonging to the order Coleoptera, as for example: cotton-boll weevil, *Anthonomus grandis*; the worm of the western maize root, *Diabrotica virgifera virgifera*; the so-called "vaquinha" (*Diabrotica longicornis barberi*); the so-called "o besouro do pepino" (*Diabrotica undecimpunctata howardi*). Additional pests include: larvae of elateridae such as *Melanotus, Eleodes, Conderus* and *Aeolus* spp; the so-called "besouro japonês" (*Popillia japonica*); white larva, *Phyllophaga crinita*; the so-called "pulguinha do milho e do arroz" (*Chaetocnema pulicaria*); the so-called "besouro do caule de girasol" (*Cylindrocupturus adspersus*); the so-called "besouro de semente de girassol cinza" (*Smicronyx sordidus*); the so-called "besouro de girasol" (*Zygogramma exclamationis*); the so-called "besouro de alfafa" (*Hypera nigrirostris*); the so-called "besouro 'sem asa' de crucíferas" (*Phyllotreta cruciferae*); the so-called "besouro da batata Colorado" (*Leptinotarsa decemlineata*); the so-called "besouro 'sem asa' listrado" (*Phyllotreta striolata*); the so-called "besouro 'sem asa' listrado da raiz de mostarda" (*Phyllotreta nemorum*) and the so-called "besouro de *Brassica*" (*Meligethes aeneus*).

The present invention further provides examples of nucleic acid compositions that are homologous to at least one portion of the sequences selected from the group consisting of SEQ ID No 1, SEQ ID No 2, SEQ ID No 3, SEQ ID No 4, SEQ ID No 5, SEQ ID No 7, SEQ ID No 8, SEQ ID NO 19 or SEQ ID NO 20 or fragments or complements thereof.

In a further embodiment, the invention provides a method for suppressing the expression of the gen of a coleoptera pest, such as cotton-boll weevil or related species, which comprises the step of providing, in the diet of the pest, an amount of a gene that suppressed at least one dsRNA, molecule transcribed from a nucleotide sequence as described herein, at least one segment of which is complementary to a miRNA sequence within the cells of the pest. The method may further comprise the death, dwarfism, or cessation of the feeding of the pest. A dsRNA molecule including its modified form like a siRNA molecule, fed to the pest according to the invention, may have at least about 80, 81, 82, 83, 84, 85, 86, 87, 88 89, 90, 91, 92, 93, 94, 95, 96, 97, 98, 99, or about 100% identity with an RNA molecule transcribed from the sequences selected from the group consisting of SEQ ID No 1, SEQ ID No 2, SEQ ID No 3, SEQ ID No 4 or fragments or complements thereof.

Besides, the invention further provides a fragment or concatamer of as nucleic acid sequence selected from the sequences selected from the group consisting of SEQ ID No 1, SEQ ID No 2, SEQ ID No 3, SEQ ID No 4 or fragments or complements thereof. The fragment may be defined as causing death or impairing the development of a harmful organism when expressed as a dsRNA and supplied to the pest. The fragment may, for instance, comprise at least about 19, 21, 23, 25, 40, 60, 80, 100, 125 or more contiguous nucleotides of the sequences selected from the group consisting of SEQ ID No 1, SEQ ID No 2, SEQ ID No 3, SEQ ID No 4, or fragments or complements thereof, of a complement thereof. DNA fragment suitable for use in the present invention is up to least 19 to about 23, or about 23 to about 100 nucleotides up to about 2000 nucleotides or more in length. Particularly suitable for the present invention are DNA sequences, including about 19 to about 400 nucleotides homologous to a garget sequence of pests. The invention also provides a ribonucleic acid expressed from any of such sequences, including a dsRNA. The sequence selected for use in the expression. of a gene suppressing agent may be constituted from a single sequence derived from one or more target pests and intended to be used in the expression of an RNA that functions in suppressing a single gene or a family of genes in one or more target pests, or the DNA sequence may be constituted as a chimera of a plurality of DNA sequences. Specifically for the present invention, this family of genes is related to the Family of the genes of chitin synthase, specifically to chitin synthase 2, and to the family of the vitellogenin genes.

In another embodiment, the invention provides DNA constructs that comprise a nucleic acid molecule encoding a dsRNA molecule described herein. The dsRNA may be formed by strand of transcription of the molecule of a nucleotide sequence that is at least about 80% to about 100% identical to the sequences selected from the group consisting of SEQ ID No 1, SEQ ID No 2, SEQ ID No 3, SEQ ID No 4, or fragments or complements thereof. Such recombinant DNA constructs may be defined as the production of dsRNA molecules, capable of inhibiting or reducing the expression of the endogenous target gene (s) in a pest cell after ingestion. The construct may include a nucleotide sequence of the invention, operatively bounded to a promoter sequence that functions in the host cell. The present invention may make use of tissue-specific or constitutive promoters. Preferably, for the present invention the tissue-specific promoters may be, but not limited to specific promoters for flower buds of cotton plants. Preferably, the present invention used the promoter uceA 1.7 (SEQ ID No 9) for expression of the dsRNAs and the promoter GHPGFS1 (SEQ ID No 10) for expression of the protein Cry8ka5.

Nucleic acid constructs according to the present invention may comprise at least one nucleotide sequence that does not occur naturally and that may be transcribed in a single-chain RNA, capable of forming a dsRNA molecule in vivo by hybridization. Such dsRNA sequences may be supplied in the diet of a coleoptera pest to achieve the desired inhibition.

A recombinant DNA construct may contain sequences substantially similar to the sequences selected from the group consisting of SEQ ID No 1, SEQ ID No 2, SEQ ID No 3, SEQ ID No 4, SEQ ID No 5, SEQ ID No 7, SEQ ID No 8, SEQ ID NO 19 or SEQ ID NO 20 or fragments or complements thereof. The dsRNAs may express from constructs introduced in various different transformation events, or may be introduced into a single nucleic acid molecule. The dsRNAs may be expressed using a single or multiple promoters. In an embodiment, the invention enables a recombinant host cell to have, in its genome, at least one recombinant DNA sequence that is transcribed to produce a dsRNA molecule, which functions when ingested by a coleoptera pest to inhibit or reduce the expression of a target gene in a pest. The dsRNA molecule may be encoded by the sequences selected from the group consisting of SEQ ID No 1, SEQ ID No 2, SEQ ID No 3, SEQ ID No 4 or fragments or complements thereof. The present invention also provides a transformed vegetable cell having, in its genome, at least a recombinant DNA sequence described herein. The transgenic plants that comprise such a transformed plant cell are also supplied, including the progeny plants of any generation, the seeds and vegetable products, each comprising the recombinant DNA. Preferably, the constructs of the present invention are substantially similar to the SEQ ID No 7, SEQ ID No 8, SEQ ID No 19 and SEQ ID No 20.

The methods and compositions of the present invention can be applied to any monocotyledonous or dicotyledonous plant, depending on the desired control of coleopteran pests. Thus, the present invention describes a transformed plant with a recombinant DNA sequence, as described in the sequences selected from the group consisting of SEQ ID No 1, SEQ ID No 2, SEQ ID No 3, SEQ ID No 4, SEQ ID No 5, SEQ ID No 7, SEQ ID No 8, SEQ ID No 19 and SEQ ID No 20 or fragments, or concatamers or complements thereof, which is transcribed to produce at least one dsRNA molecule, which functions when ingested by a coleopteran pest to inhibit or reduce the expression of a target gene.

The invention also provides combinations of methods and compositions to control infestations of coleoptera pests. A means of providing dsRNA method as described for protecting plants against infestation by insects is, in conjunction, one or more insecticidal agents that exhibit characteristics other than those exhibited by the dsRNA methods and compositions. For example, one or more Bt proteins may be made available in the diet of insects, in combination with one or more dsRNAs as described herein. The composition formulated for topical or derived application, using a transgenic approach, which combines the methods and compositions of dsRNA with Bt, may be used for creating synergisms that were not known before in the art to control infestation by insects. A synergism is the reduction in the level of expression necessary for the dsRNA (s) or the protein of Bt (s). When combined, the smallest effective dose of each of the pest controlling agents may be used. It is believed that the insecticidal proteins of Bt creates entry pores through which the dsRNA molecules are capable of penetrating more effectively remote spaces from the intestines of insect pest, or in a more effective manner for cells in the proximity of injuries created by the protein Bt Bt, thus requiring a smaller amount of Bt or dsRNA to achieve the desired result of insecticidal action or desired inhibition or suppression of a specific biologic function in the target pest.

The present invention provides, therefore, a composition containing one or more different toxic pesticidal agents for the same pest or species of insects where, at least one of which comprises a dsRNA described herein. In certain embodiments, the second agent may be one selected from the group consisting of patatin, an insecticidal protein of *Bacillus thuringiensis*, an insecticidal protein of *Xenorhabdus*, in insecticidal protein of *Photorhabdus*, an insecticidal protein of *Bacillus laterosporous*, an insecticidal protein of *Bacillus sphaericus*, enzymes of the family of chitinase and lignin. An insecticidal protein of *Bacillus thuringiensis* may be any one of a number of insecticidal proteins, including, but not limited to CryI, Cry8, Cry10, Cry35 TIC851, CryET70, Cry225 TIC901, TIC1201, TIC407, TIC417, insecticidal protein CryET33 and binary CryET34, insecticidal binary protein CryET80 and CryET76, insecticidal binary protein TICIOO and TICIOI, insecticidal binary of protein PS 149BI, insecticidal protein VIP, protein TIC900 or the like, or combinations of the insecticidal proteins ET29 or ET37 with insecticidal proteins TIC810 or TIC812 and insecticidal chimeras of any one of the above-cited proteins. Particularly for the present invention one uses the toxin Cry8ka5 (SEQ ID No 5—Cry8ka5 and SEQ ID No 6—Cry8ka5_aa).

A nucleic acid that is made available in the diet may be included in an artificial diet formulated to meet the special nutritional needs for a determined pest. The diet may also be recombinant cell transformed with a DNA sequence constructed for the expression. of the target agent, RNA or a gen suppressing agent. After ingestion of one of more transformed cells by the pest, the desired result is phenotypically observed, indicating that the agent has been used for inhibiting or reducing the expression of a target nucleotide sequence that is within the cell of the pest.

A target gene can code for the suppression of an essential protein. For the present invention, the target genes are of the Family of chitin synthase, the function of which is the constitution of the formation of the cuticle, trachea and chitin of the peritrophic membrane, and the genes of the vitellogenin family, which are of great importance in the reproduction of the insects. Therefore, the inhibition or reduction of the expression of such genes may affect functions that are essential to the survival of the insect to be selected from the differentiation group and development of the cuticle, larval maturation, transcription of the larval stage, pupation, digestion and assimilation of nutrients, protection against pathogens.

The invention further provides, in conjunction with the suppression of genes that are essential to the insects, the expression of a toxin Cry to improve the action response of the plants against the pest insects. Particularly for the present invention, one sues a protein described and isolated in patent application PI0906128-2, the toxin Cry8ka5 (SEQ ID No 5—Cry8ka5 and SEQ ID No 6—Cry8ka5_aa).

Thus, the invention provides a gene construct characterized by comprising:
(i) a promoter functional in plant;
(ii) a sense fragment substantially similar to the SEQ ID NO: 1;
(iii) a sense fragment substantially similar to the SEQ ID NO: 2;
(iv) a spacer sequence;
(v) an antisense fragment substantially similar to the SEQ ID NO: 3;
(vi) an antisense fragment substantially similar to the SEQ ID NO: 4;
(vii) a terminator functional in plant; and alternatively
(viii) a promoter functional in plant;
(ix) a nucleotide sequence substantially similar to the SEQ ID NO 5;
(x) um terminador funcional em planta.

The invention further describes a gene construct characterized by comprising:
(i) a promoter functional in plant;
(ii) a sense fragment substantially similar to the SEQ ID NO: 1;
(iii) a spacer sequence;
(iv) an antisense fragment substantially similar to the SEQ ID NO: 3;
(v) a terminator functional in plant;
(vi) a promoter functional in plant;
(vii) a nucleotide sequence substantially similar to the SEQ ID NO 5; and
(viii) a terminator functional in plant.

In a further embodiment, the invention describes a gene construct characterized by comprising:
(i) a promoter functional in plant;
(ii) a sense fragment substantially similar to the SEQ ID NO: 2;
(iii) s spacer sequence;
(iv) an antisense fragment substantially similar to the SEQ ID NO: 4;
(v) a terminator functional in plant;
(vi) a promoter functional in plant;
(vii) a nucleotide sequence substantially similar to the SEQ ID NO 5; and
(viii) a terminator functional in plant.

The invention further describes a method for producing transgenic plants capable of producing dsRNA of interest in order for the pest insect, upon feeding on these plants, will the target gene silences, characterized by comprising the steps of:
I) providing a gene sequence characterized by comprising:
(i) a promoter functional in plant;
(ii) a sense fragment substantially similar to the SEQ ID NO: 1;
(iii) a sense fragment substantially similar to the SEQ ID NO: 2;
(iv) a spacer sequence;
(v) an antisense fragment substantially similar to the SEQ ID NO: 3;
(vi) an antisense fragment substantially similar to the SEQ ID NO: 4;
(vii) a terminator functional in plant; and alternatively
(viii) a promoter functional in plant;
(ix) a nucleotide sequence substantially similar to the SEQ ID NO 5;
(x) a terminator functional in plant;
II) inserting the molecule obtained in "I" into a plant cell or cells to produce a transgenic cell or cells; and
III) growing or regenerating a transgenic plant from the transgenic cell or cells.

The invention also describes a method for producing transgenic plants capable of producing dsRNA of interest in order for the pest insect, upon feeding o these plants, will have the target gene silenced, characterized by comprising the steps of:

I) providing a gene construct characterized by comprising:
(i) a promoter functional in plant;
(ii) a sense fragment substantially similar to the SEQ ID NO: 1;
(iii) a spacer sequence;
(iv) an antisense fragment substantially similar to the SEQ ID NO: 3;
(v) a terminator functional in plant;
(vi) a promoter functional in plant;
(vii) a nucleotide sequence substantially similar to the SEQ ID NO 5; and
(viii) a terminator functional in plant.
II) inserting the molecule obtained in "I" into a plant cell or cells to produce a transgenic cell or cells; and
III) growing or regenerating a transgenic plant from the transgenic cell or cells.

The invention also describes a method for producing transgenic plants capable of producing dsRNA of interest in order for the pest insect, upon feeding on these plants, will have the target gene silenced, characterized by comprising the steps of:

I) providing a genic construction characterized by comprising:
(i) a promoter functional in plant;
(ii) a sense fragment substantially similar to the SEQ ID NO: 2;
(iii) a spacer sequence;
(iv) an antisense fragment substantially similar to the SEQ ID NO: 4;
(v) a terminator functional in plant;
(vi) a promoter functional in plant;
(vii) a nucleotide sequence substantially similar to the SEQ ID NO 5; and
(viii) a terminator functional in plant;
II) inserting the molecule obtained in "I" into a plant cell or cells to produce a transgenic cell or cells; and
III) growing or regenerating a transgenic plant from the transgenic cell or cells.

Another embodiment of the invention is a method for controlling pest insects, characterized in that is comprises making available, in their diet, an agent comprising a double-stranded ribonucleotide sequence produced from the gene construct characterized by comprising:
(i) a promoter functional in plant;
(ii) a sense fragment substantially similar to the SEQ ID NO: 1;
(iii) a sense fragment substantially similar to the SEQ ID NO: 2;
(iv) a spacer sequence;
(v) an antisense fragment substantially similar to the SEQ ID NO: 3;
(vi) an antisense fragment substantially similar to the SEQ ID NO: 4;
(vii) a terminator functional in plant; and alternatively
(viii) a promoter functional in plant;
(ix) a nucleotide sequence substantially similar to the SEQ ID NO 5;
(x) a terminator functional in plant.

The invention also provides a method for controlling pest insects, characterized in that it comprises making available, in their diet, an agent comprising a double-stranded ribonucleotide sequence produced from the gene construction characterized by comprising:
(i) a promoter functional in plan;
(ii) a sense fragment substantially similar to the SEQ ID NO: 1;
(iii) a spacer sequence;
(iv) an antisense fragment substantially similar to the SEQ ID NO: 3;
(v) a terminator functional in plan;
(vi) a promoter functional in plant;
(vii) a nucleotide sequence substantially similar to the SEQ ID NO 5; e
(viii) a terminator functional in plant.

The invention also provides a method for controlling pest insects, characterized in that it comprises making available, in their diet, an agent comprising a double-stranded ribonucleic sequence produced from the gene construct characterized by comprising:
(i) a promoter functional in plant;
(ii) a sense fragment substantially similar to the SEQ ID NO: 2;
(iii) a spacer sequence;
(iv) an antisense fragment substantially similar to the SEQ ID NO: 4;
(v) a terminator functional in plant;
(vi) a promoter functional in plant;
(vii) a nucleotide sequence substantially similar to the SEQ ID NO 5; and
(viii) a terminator functional in plant.

Another embodiment of the invention is a method for improving the yield of cultivated plants, subject to infection by pest insects, characterized by comprising the steps of:
II. obtaining a transgenic plant by introducing a gene construct comprising:
(i) a promoter functional in plant;
(ii) a sense fragment substantially similar to the SEQ ID NO: 1;
(iii) a sense fragment substantially similar to the SEQ ID NO: 2;
(iv) a spacer sequence;
(v) an antisense fragment substantially similar to the SEQ ID NO: 3;
(vi) an antisense fragment substantially similar to the SEQ ID NO: 4;
(vii) a terminator functional in plant; and alternatively
(viii) a promoter functional in plan;
(ix) a nucleotide sequence substantially similar to the SEQ ID NO 5;
(x) a terminator functional in plant.
II. Growing the plant obtained in "I" so that it will express the sequences of interest of said gen construction, in order that the products of this expression will reproduce or suppress the population of pest insects.

Still a further embodiment of the invention is a method for improving the yield of cultivated plants, subject to infestation by pest insects, characterized by comprising the steps of:
II. obtaining a transgenic plant by introducing a gene construct comprising:
(i) a promoter functional in plant;
(ii) a sense fragment substantially similar to the SEQ ID NO: 1;
(iii) a spacer sequence;
(iv) an antisense fragment substantially similar to the SEQ ID NO: 3;
(v) a terminator functional in plant;
(vi) a promoter functional in plant;
(vii) a nucleotide sequence substantially similar to the SEQ ID NO 5; e
(viii) a terminator functional in plant;

II. growing the plant obtained in "I" so that it will express the sequences of interest of said gene construction, in order for the products of this expression will reproduce or suppress the population of pest insects.

A further embodiment of the invention is a method for improving the yield of cultivated plants, subject to infestation by pest insects, characterized by comprising the steps of:
I. obtaining a transgenic plant by introducing a gene construct comprising:
(i) a promoter functional in plant;
(ii) a sense fragment substantially similar to the SEQ ID NO: 2;
(iii) a spacer sequence;
(iv) an antisense fragment substantially similar to the SEQ ID NO: 4;
(v) a terminator functional in plant;
(vi) a promoter functional in plant;
(vii) a nucleotide sequence substantially similar to the SEQ ID NO 5; e
(viii) a terminator functional in plant;
II. growing the plant obtained in "I" so that it will express the sequences of interest of said gene construct, in order that the products of this expression will reproduce or suppress the population of pest insects.

The invention further describes a method of producing a product characterized in that it comprises obtaining a plant containing the gene construct of the present invention, or a part thereof, preparing it from the whole or a part of this plant, so that the latter will be made available in the diet of insects of interest, with a view to reduce or suppress their population. A invenção prevê ainda iniciadores de ácido nucleico compreendendo uma primeira e segunda molécula de ácido nucleico capaz de amplificar uma construção gênica da presente invenção.

It is a further objective of the present invention to provide a kit for identifying a nucleic acid molecule of a biologic sample characterized by comprising a first and a second nucleic acid primer, where these are capable of amplifying a molecule substantially similar to the SEQ ID No 7 or SEQ ID NO 8 or SEQ ID NO 19 or SEQ ID NO 20 or a fragment thereof.

Another objective of the present invention is a method of identifying a plant containing the gene construct of the present invention, characterized by comprising the following steps:
a. forming a mixture comprising a biologic sample containing a plant DNA and a first and a second nucleic acid primer capable of amplifying a nucleic acid molecule substantially similar to the SEQ ID No 7 or SEQ ID NO 8 or SEQ ID NO 19 or SEQ ID NO 20 or a fragment thereof;
b. reacting the mixture under conditions that enable the first and the second primers to amplify a nucleic acid molecule substantially similar to the SEQ ID No 7 or SEQ ID NO 8 or SEQ ID NO 19 or SEQ ID NO 20 or a fragment thereof; and
c. detecting the presence of an amplified fragment of a nucleic acid molecule substantially similar to the SEQ ID No 7 or SEQ ID NO 8 or SEQ ID NO 19 or SEQ ID NO 20 or a fragment thereof, wherein the presence of the specific nucleic acid molecule in the plant indicates that the latter is an event of genetically modified plant.

It is a further objective of the present invention to provide a method of identifying a plant containing any of the gene constructs of the present invention, characterized by comprising the following steps:
a. forming a mixture comprising a biologic sample containing a plant DNA and a nucleic acid molecule probe capable of hybridizing a nucleic acid molecule substantially similar to the SEQ ID No 7 or SEQ ID NO 8 or a fragment thereof;
b. reacting the mixture under conditions that enable the nucleic acid molecule probe to hybridize a nucleic acid molecule substantially similar to the SEQ ID No 7 or SEQ ID NO 8 or a fragment thereof; and
c. detecting the hybridization of the probe to the DNA, wherein the presence of hybridization of the nucleic acid molecule probe to the plant DNA indicates that that latter is an event of genetically modified plant.

Another objective of the present invention relates to a method of reproducing a plant resistant to pest insects, characterized by comprising the following steps:
a. crossing a plant comprising a nucleic acid molecule substantially similar to the SEQ ID No 7 or SEQ ID NO 8 or SEQ ID NO 19 or SEQ ID NO 20 or a fragment thereof with a second plant;
b. obtaining seed from the crossing of step (a);
c. obtaining a sample of the DNA of the seed; and
d. detecting the presence of a nucleic acid molecule substantially similar to the SEQ ID No 7 or SEQ ID NO 8 or a fragment thereof, wherein the presence of the latter indicates that the seed is capable of producing a plant resistant to pest insects.

The invention also describes a method for growing a plant, characterized by comprising the following steps:
a. providing a seed or seedling comprising a nucleic acid molecule substantially similar to the SEQ ID No 7 or SEQ ID NO 8 or SEQ ID NO 19 or SEQ ID NO 20 or a fragment thereof;
b. planting or sewing the material obtained in steps (a) in a substrate, soil or environment suitable for germination or sprouting, growing and development with a view to vegetable production, the assembly constituting a cultivation system in which populations of pest insects are controlled.

Other features of the invention are transformation and expression vectors, cells and transgenic plants, methods for the expression of the molecules of the present invention in these plants, as well as the use of these molecules in controlling pest insects.

In the context of this description, numberless terms will be used, and so the will be better detailed hereinafter.

The term "nucleic acid" refers to a big molecule which may be a single-stranded or a double-stranded one, composed by monomers (nucleotides) containing a sugar, a phosphate and a purine or pyrimidine base. A "fragment of nucleic acid" is a fraction of a given nucleic acid molecule. "Complementarity" refers to the specific pairing of purine and pyridine bases that consists of nucleic acids: pairs of adenine with thymine and pairs of guanine with cytosine. Then, the "complement" of a first fragment of nucleic acid refers to the second fragment of nucleic acid whose nucleotide sequence is complementary to the first nucleotide sequence.

In more developed plants, deoxyribonucleic acid (DNA) is the genetic material, whereas ribonucleic acid (RNA) is involved in the transfer of information of the DNA in proteins. A "genome" is the whole main part of the genetic material contained in each cell of an organism. The term "nucleotide sequence" refers to the sequences of nucleotide polymers, forming a DND or RNA strand, which may be single strand or double strands, optionally synthetic, non-natural or with altered nucleotide bases capable of incorporation into DNA or RNA polymers. The term "oligomer" refers to short nucleotide sequences, usually up to 100 bases in length. The term "homologous" refers to the linkage between the nucleotide sequences of two nucleic acid molecules or between the amino acid sequences of two protein molecules. The estimate of such homology is provides by hybridizing DNA-DNA or RNA-RNA under stringency conditions, as defined in the prior art (as mentioned in document US20030074685, Hames and Higgins, Ed. (1985) Nucleic Acid Hybridization, IRL Press, Oxford, U.K); or by incorporation of similarity of sequence between two nucleic acid molecules or proteins (as mentioned in document US20030074685, Needleman et al., J. Mol. Biol. (1970) 48:443-453).

"Gene" refers to the nucleotide fragment that expresses a specific protein, including preceding regulatory sequences (5' untranslated regions) and subsequent (3' untranslated region) to the coding region. "Native gene" refers to an isolated gene with its own regulatory sequence found in nature. "Chimeric gene" refers to the gene that comprises coding, regulating and heterogeneous sequences, not found in nature. The chimeric gene of the present invention comprises isolated nucleic acid molecules in the sense or antisense orientation, bounded optionally to active promoters. Gene constructs of the present invention may contain one or more chimeric genes and may or may not exhibit introns. "Endogenous gene" refers to the native gene that is normally found in its natural location in the genome and is not isolated. An "exogenous gene" refers to a gene that is not normally found in the host organism, but that is introduced by gene transfer. "Pseudogene" refers to a nucleotide sequence that does not encode a functional enzyme.

"Coding sequence" refers to the DNA sequence that encodes a specific protein and excludes the non-coding sequence. An "interrupted coding sequence" means the sequence that acts as a separator (for example, one or more introns bounded by junctions). An "intron" is a nucleotide sequence that is transcribed and is present in the pre-mRNA, but is removed by cleavage and re-binding of the mRNA within the cell, generating a mature mRNA that may be translated into a protein. Examples of introns include, but are not limited to intron pdk2, catalase intron of castor, intron Delta 12 desnaturase of cotton-plant, Delta 12 desnaturase de *Arabidopsis*, intron ubiquitin of maize, intron of SV40, introns of the gene of malate synthase.

"RNA transcript" refers to the product resulting from the transcription catalyzed by the RNA polymerase of a DNA sequence. When the RNA transcript is a perfect copy of the DAN sequence, it is referred to as a primary transcript or it may be an RNA sequence derived from a post-transcriptional process of the primary transcript and is then referred to as a mature transcript. "Messenger RNA (mRNA)" refers to the RNA that is without introns. "Sense RNA" refers to an RNA transcript that includes the mRNA. "Antisense RNA" refers to an RNA a transcript that is complementary to all the parts of a primary transcript or mRNA and that can block the expression of a target gene by interference in the processing, transport and/or translation of its primary or mRNA transcript. The complementarity of an antisense RNA may be with any part of the specific gene transcript, that is, untranslated 5' sequence, untranslated 3' sequence, introns or coding sequence. Besides the antisense RNA may contain regions of ribozyme sequences that increase the efficacy of the antisense RNA to block the gene expression. "Ribozyme" refers to the catalytic RNA and includes specific sequences of endoribonucleases. "DsRNA (double-stranded)" refers to the structure clamp structure formed between the sequence of the sense mRNA or RNA, the sequence of a spacing region and the sequence of the antisense RNA. "Spacing region" refers to the nucleotide sequence that is not related to the sequence of the target gene, like the sequence of an intro.

The term "vector" refers to a replicon, as a plasmid, phage or virus, in which other genetic sequences or elements (be they of DNA or RNA) may be bounded. Thus, the genes may be replicated together with the vector. The term "recombinant vector" results from the combination of a commercial vector with nucleic acid nucleic acid molecules of the present invention bounded to a promoter of interest and a termination signal. Such vectors may be obtained commercially, including those supplied by Clontech Laboratories, Inc (Palo Alto, Calif.), Stratagene (La Jolla, Calif.), Invitrogen (Carlsbad, Calif.), New England Biolabs (Beverly, Mass.) and Promega (Madison, Wis.). A few examples of vectors used in the present invention, but not limited thereto, are the vectors of the series pCambia (BioForge Co.), pBI121 (Chen, Po-Yen; Wang, Chen-Kuen; Soong, Shaw-Ching; To, Kin-Ying. Complete sequence of the binary vector pBI121 and its application in cloning T-DNA insertion from transgenic plants. Molecular Breeding vol. 11 issue 4 May 2003. p. 287-293), pBSK (Addgene Co.), pGEM-T easy (Promega Corporation), pET101/D-TOPO (Invitrogen). The obtainment of recombinant vectors comprising promoters bounded to nucleic acids is known from the prior art and can be found in Sambrook et al. (Sambrook, J., Russell, D. W., Molecular Cloning, A Laboratory Manual, 2nd ed., Cold Spring Harbor Laboratory Press. 1989).

"Substantially similar" or "substantial similarity" refers to nucleic acid fragments in which changes in one or more nucleotide bases do not affect the capability of the nucleic acid fragment to mediate the alteration of the gene expression by gene silencing, for instance, of the antisense technology, co-suppression or RNA of interference (RNAi). Substantially similar nucleic acid fragments of the present invention may be characterized also by the percentage of similarity of their nucleotide sequences to the nucleotide sequences of the nucleic acid fragments described herein (SEQ ID NO 1, SEQ ID NO 2, SEQ ID NO 3, SEQ ID NO 4, SEQ ID NO 5, SEQ ID NO 7, SEQ ID NO 8, SEQ ID NO 19 and SEQ ID NO 20), as determined by a few common algorithms employed in the prior art. The preferred nucleic acid fragments are those whose nucleotide sequences have at least about 40 or 45% sequence identity, preferably about 50% or 55% sequence identity, more preferably about 60% or 65% sequence identity, more preferably about 70% or 75% sequence identity, more preferably about 80% or 85% sequence identity, still more preferably with about 90%, 91%, 92%, 93%, 94%, 95%, 96%, 97%, 98% or 99% sequence identity as compared to the reference sequence.

One of the ways of forming the dsRNA is establishing in the DNA molecule the nucleotide sequence of the target gene in the sense orientation, and a nucleotide sequence in the antisense orientation, and there may be or may not be a spacing region between the sense and antisense nucleotide sequences. The nucleotide sequences mentioned may be constituted by about 19 nt to 2000 nt or still about 5000 nucleotides or more, each having substantial similarity of total sequence with about 40% to 100%. The longer the sequence, the lesser stringency is required for total substantial similarity of the sequence. The fragments containing at least about 19 nucleotides should be preferably about 90%, 91%, 92%, 93%, 94%, 95%, 96%, 97%, 98% or 99% sequence similarity as compared to the reference sequence, with possibility of having about 2 non-contiguous different nucleotides. Preferably one uses fragments above 60 pb, still more preferably fragments between 100 and 600 pb.

In one of the embodiments of the invention, the dsRNA molecule may contain one or more regions having substantial sequence similarity with at least about 19 consecutive nucleotides of the sense nucleotides of the target gene, defined as first region and, one or more regions having substantial sequence similarity to the regions with 19 consecutive nucleotides of the complement of the sense nucleotides of the target gene, defined as second region, wherein these regions may have pairs of bases separating them from each other.

Consequently the dsRNA (double-stranded RNA) as described may be introduced into the host cells by introducing and possibly integrating a gene construct containing the nucleic acid molecules of the present invention, transcription of thereof for production of the dsRNA.

"Promoter" refers to the DNA sequence in which a gene, usually located upstream from the coding sequence, which controls the expression of the coding sequence providing the knowledge by the RNA polymerase and other factors required for the transcription itself. In an artificial DNA construct, promoters may also be used to transcribe dsRNA. Promoters may also contain DNA sequences that are involved in the binding of protein factors which control the effect of the beginning of the transcription in response to physiological conditions or development conditions.

In one of the aspects of the invention, the promoter is a constitutive one. In another aspect of the invention, the activity of the promoter is stimulated by external or internal factors such as, for example, but not limited to hormones, chemical compounds, mechanical impulses, and biologic or abiotic stress conditions. The activity of the promoter may also be regulated in a time and space manner (as for example, tissue-specific ones and promoters regulates during the development).

The promoter may contain enhancers. An enhancer is a DNA sequence that can stimulate the promoter activity. It may be an innate element of the promoter or a heterologous element inserted to raise the level and/or the tissue-specificity of a promoter. "Constitutive promoters" refer to those which direct the gene expression. in all the tissues and all the time. "Tissue-specific" or "development-specific" promoters are those that direct the gene expression almost exclusively in specific tissues, such as leaves, roots, stems, flowers, fruits or seeds, or in specific development stages in a tissue, as in the beginning or at the end of embryogenesis. The term "expression." refers to the transcription and stable accumulation of the dsRNA derived from the nucleic acid fragments of the invention which, in conjunction with the protein production apparatus, results in altered levels of myo-inositol 1-phosphatesynthase. "Inhibition by interference" refers to the production of dsRNA transcripts capable of preventing the expression of the target protein.

"Suitable regulatory sequences" refer to the nucleotide sequences in native or chimeric nucleotides that are bounded above (untranslated 5' region) within and/or below (untranslated 3' region) of the nucleic acid fragments of the invention, which control the expression of the nucleic acid fragments of the invention.

"Altered levels" refer to the production of genic products in transgenic organisms in amounts or proportions that differ from those in normal or non-transgenic organisms. The present invention also discloses vectors, which include sequences of the gene of the enzyme chitin 2 and vitellogenin gene in the sense and antisense orientation, and host cells which are genetically engineered with vectors of the invention. "Transformation" refers to the transfer of the exogenous gene into a host organism and its genetically stable heritage.

"Plants" relate to photosynthetic organism, both eukaryote and prokaryote, wherein the term "developed plants" refer to eukaryote plants. The nucleic acids of the invention may be used to impart traits that are desired in essentially any plant. Then, the invention has use on various species of plants, including species of the genera *Anacardium, Anona, Arachis, Artocarpus, Asparagus, Atropa, Avena, Brassica, Carica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoseyamus, Lactuca, Linum, Lolium, Lupinus, Lycopersicon, Malus, Manihot, Majorana, Medicago, Nicotiana, Olea, Oryza, Panieum, Pannesetum, Passiflora, Persea, Phaseolus, Pistachia, Pisum, Pyrus, Prunus, Psidium, Raphanus, Ricinus, Secale, Senecio, Sinapis, Solanum, Sorghum, Theobromus, Trigonella, Triticum, Vicia, Vitis, Vigna*, and *Zea*.

In one of the aspects of the invention, the promoter is a promoter expressed in plants. As used herein, the term "promoter expressed in plants" means a DNA sequence that is capable of initiating and/or controlling the transcription of a plant cell. This includes any promoter of vegetable origin, any promoter of non-vegetable origin which is capable of directing the expression in a vegetable cell, for example promoters of viral or bacterial origin, such as CaMV35S (as mentioned in patent application US20030175783, Hapster et al., 1988 Mol. Gen. Genet. 212, 182-190) and promoters of the gene present in the T-DNA of *Agrobacterium*; tissue-specific or organ-specific promoters, including, but not limited to seed-specific promoters (WO8903887), organ-primordia specific promote (as mentioned in patent application US20030175783, An et al., 1996 The Plant Cell 8, 15-30), stem-specific promoters (as mentioned in patent application US20030175783, Keller et al., 1988 EMBO J. 7: 3625-3633), leaf-specific promoters (as mentioned in patent application US20030175783, Hudspeth et al., 1989 Plant Mol Biol 12:579-589), mesophyll-specific promoters, root-specific promoters (as mentioned in patent application US20030175783, Keller et al., 1989 Genes Devel. 3:1639-1646), tuber-specific promoters (as mentioned in patent application US20030175783, Keil et al., 1989 EMBO J. 8: 1323:1330), vascular-tissue-specific promoters (as mentioned in patent application US20030175783, Peleman et al., 1989 Gene 84: 359-369), stamen-specific promotes (WO8910396, WO9213956), dehiscence zone-specific promoters (WO9713865); and the like.

The termination signal of the transcription and the polyadenylation region of the present invention includes, but is not limited to termination signal SV40, adenylation signal of HSV TK, termination signal of the gene of nopaline synthetase of *Agrobacterium tumefasciens* (nos), termination signal of the gene RNA 35S do CaMV, termination signal of the virus that attacks *Trifolium subterranean* (SCSV), termination signal of the gene trpC of *Aspergillus nidulans*, and other similar ones.

The present invention also includes providing dsRNA molecules which can be obtained by transcription of the molecules contained in the gene constructs, and which are useful to the methods according to the present invention.

Another objective of the present invention is to provide eukaryote cells and eukaryote organisms containing dsRNAm molecules of the invention or containing the chimeric genes or the gene constructs capable of producing dsRNA molecules of the invention. The gene constructs may be stably integrated in the genome of the cells of eukaryote organisms.

In another embodiment of the invention, the gene constructs may be provided in a DNA molecule capable of replicating autonomously in the cells of eukaryote organisms such as viral vectors. The gen construct or the dsRNA may also be arranged in a transient form in the cells of eukaryote organisms.

The gene constructs or chimeric gene of the present invention may be introduced into the genome of the host plant by various conventional techniques. For example, it may be introduced directly into the genomic DNA of the vegetable cell by using such techniques as electroporation and microinjection of protoplasts of plant cells, or the construct may be introduced directly into the vegetable tissue by using ballistic methods such as bombardment of DNA-covered particles.

Microinjection techniques are known from the prior art and well described in scientific and patent literature. The introduction of gene constructs by using precipitations of polyethylene glycol is described in Paszkowski et al. Embo J. 3:2717-2722, 1984 (as mentioned in patent application US20020152501). Electroporation techniques are described in From et al. Proc. Natl. Acad. Sci. USA 82:5824, 1985 (as mentioned in patent application US20020152501). Ballistic transformation techniques are described in Klein et al. Nature 327:70-73, 1987 (as mentioned in patent application US20020152501).

Alternatively, the gene constructions may be combined with suitable T-DNA-flanked regions introduced into the host conventional vector *Agrobacterium tumefasciens*. The virulence function of the host *Agrobacterium tumefasciens* will direct the insertion of the gene constructs and adjacent marker into the DNA of the vegetable cell when the cell is infected by the bacteria. Transformation techniques mediated by *Agrobacterium tumefasciens*, including disarmament and the use of binary vectors, are well-known in the scientific literature (as mentioned in patent application US 20020152501, Horsch et al. Science 233:496-498, 1984; and Fraley et al. Proc. Natl. Acad. Sci. USA 80:4803, 1983).

Transformed cell plants that are derived from any one of the above-described transformation techniques may be grown to generate a whole plant that has the transformed genotype and then the desired phenotype, such as absence or reduction of the formation of chitinous structures of coleopteran insects such as the cuticle and/or peritrophic membrane. Such regeneration techniques rely upon manipulation of certain phytohormones in a tissue culture medium, typically containing a biocidal marker and/or herbicide, which should be introduced together with the desired nucleotide sequence. Regeneration of plants from a protoplast culture is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985 (as mentioned in patent application US20020152501). The regeneration may also be achieved through plant calli, explants, organs, or a part thereof. Such regeneration techniques are described generally in Klee et al., Ann. Ver. Of Plant Phys. 38:467-486, 1987 1985 (as mentioned in patent application US20020152501).

Without restricting the invention to a particular action mode, it is expected that the enzyme in eukaryote cells responsible for generating small RNA molecules with about 21 dsRNA nucleotides (like DICER in *Drosophila*) can be saturated by including excess dsRNA sequences (that is, complementary RNA molecules) which are not related to the nucleotide sequence of the target gene or of the gene to be silenced.

The natural variation in the post-transcriptional regulation of the expression of the target gene occurring between different lines of eukaryote organisms comprising the same dsRNA molecule will be replaced by manipulating the gene silencing spectrum. This fact may occur by including extra dsRNA nucleotide sequences, not related to the target gene, which are optionally linked to the dsRNA formed by the first and second regions.

The embodiments of the present invention can be effective against a variety of pests. For the purposes of the present invention, the pests include, but are not limited to insects, fungi, bacteria, nematode, mites, protozoan pathogens, animal parasites, and the like. Pests of particular interest are pest insects, particularly pest insects that cause significant damage to agricultural plants. By "pest insects" one understands insects and other similar pests, such as insects of the orders Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularmente Coleoptera, especially *Anthonomus grandis, Diabrotica virgifera, Tenebrio molitor, Tribolium castaneum, Phoracantha semipunctata, Lixus angustatus, Acanthoscelides obtectus* and other coleopteran that cause damage to agronomically important wood and plants of the families Scolytidae, Cerambycidae, Curculionidae and Bostrichida. Pest insects of the present invention of most cultivars include, but are not limited to: Milho (Maize plant)—*Ostrinia nubilalis, Agrotis ipsilon, Helicoverpa zea, Spodoptera frugiperda, Diatraea grandiosella, Elasmopalpus lignosellus, Diatraea saccharalis, Diabrotica virgifera virgifera, Diabrotica longicornis barberi, Diabrotica undecimpunctata howardi, Melanotus* spp., *Cyclocephala borealis, Cyclocephala immaculata, Popillia japonica, Chaetocnema pulicaria, Sphenophorus maidis, Rhopalosiphum maidis, Anuraphis maidiradicis, Blissus leucopterus leucopterus, Melanoplus femurrubrum, Melanoplus sanguinipes, Hylemya platura, Agromyza parvicornis, Anaphothrips obscrurus, Solenopsis milesta, Tetranychus urticae;* Sorgo—*Chilo partellus, Spodoptera frugiperda, Helicoverpa zea, Elasmopalpus lignosellus, Feltia subterranea, Phyllophaga crinita, Eleodes, Conoderus,* and *Aeolus* spp., *Oulema melanopus, Chaetocnema pulicaria, Sphenophorus maidis, Rhopalosiphum maidis, Sipha flava, Blissus leucopterus leucopterus, Contarinia sorghicola, Tetranychus cinnabarinus, Tetranychus urticae;* Trigo (wheat plant)—*Pseudaletia unipunctata, Spodoptera frugiperda, Elasmopalpus lignosellus, Agrotis orthogonia, Elasmopalpus lignosellus, Oulema melanopus, Hypera punctata, Diabrotica undecimpunctata howardi, Schizaphis graminum, Macrosiphum avenae, Melanoplus femurrubrum, Melanoplus differentialis, Melanoplus sanguinipes, Mayetiola destructor, Sitodiplosis mosellana, Meromyza americana, Hylemya coarctata, Frankliniella fusca, Cephus cinctus, Aceria tulipae;* Girassol—*Cylindrocupturus adspersus, Smicronyx fulus, Smicronyx sordidus, Suleima helianthana, Homoeosoma electellum, Zygogramma exclamationis, Bothyrus gibbosus, Neolasioptera murtfeldtiana;* Algodão (cotton plant)—*Heliothis virescens,* lagarta-das-maçãs (apple caterpillar); *Helicoverpa zea,* lagarta da espiga do milho (maize spike caterpillar); *Spodoptera exigua,* lagarta do cartucho (cartridge caterpillar); *Pectinophora gossypiella,* lagarta rosada (rosy caterpillar); *Anthonomus grandis,* bicudo-do-algodoeiro (cotton-boll weevil); *Aphis gossypii,* pulgão-do-algodoeiro (cotton-plant-leaf louse); *Pseudatomoscelis seriatus,* pulga saltadora do algodão (cotton-plant jumping louse); *Trialeurodes abutilonea, mosca branca* (white fly) *Bemisia tabaci; Melanoplus femurrubrum, gafanhoto* (grasshopper); *Melanoplus differentialis, gafanhoto* (grasshopper); *Thrips tabaci*, tripes-do-fumo (tobacco tripes); *Franklinkiella fusca*, tripes; *Tetranychus cinnabarinus*, ácaro vermelho (red mite); *Tetranychus urticae*, ácaro-rajado (striped mite); Arroz (rice plant)—*Diatraea saccharalis, Spodoptera frugiperda, Helicoverpa zea, Colaspis brunnea, Lissorhoptrus oryzophilus, Sitophilus oryzae, Nephotettix nigropictus, Blissus leucopterus leucopterus, Acrosternum hilare*; Soja (soybean plant)—*Pseudoplusia includens, Anticarsia gemmatalis, Plathypena scabra, Ostrinia nubilalis, Agrotis ipsilon, Spodoptera exigua, Heliothis virescens, Helicoverpa zea, Epilachna varivestis, Myzus persicae, Empoasca fabae, Acrosternum hilare, Melanoplus femurrubrum, Melanoplus differentialis, Hylemya platura, Sericothrips variabilis, Thrips tabaci, Tetranychus turkestani, Tetranychus urticae*; Cevada (barley plant)—*Ostrinia nubilalis, Agrotis ipsilon, Schizaphis graminum, Blissus leucopterus leucopterus; Acrosternum hilare, Euschistus servus, Jylemya platura, Mayetiola destructor, Petrobia latens*; Canola (canola plant)—*Vrevicoryne brassicae, Phyllotreta cruciferae, Phyllotreta striolata, Phyllotreta nemorum, Meligethes aeneus, Meligethes rufimanus, Meligethes nigrescens, Meligethes canadianus*, and *Meligethes viridescens*; Batata (potato plant)—*Leptinotarsa decemlineata*. Particularly for the present invention the pest of interest is the *Anthonomus grandis*.

EXAMPLES

The present invention is further defined in the following Examples. It should be understood that these Examples, when they indicate a part of the invention, are given by way of illustration alone, without being limitative of the scope of the present inventions.

Usual techniques of molecular biology such as transformation of bacteria and electrophoresis in gel of nucleic acid agarose are referred to through common terms to know them. Details of the practice of these techniques, which are well known from the prior art, are described in Sambrook, et al. (Molecular Cloning, A Laboratory Manual, 2nd ed. (1989), Cold Spring Harbor Laboratory Press). Various solutions used in experimental handling are referred by their common names like "lysis solution", "SSC", "SDS", etc. The compositions of these solutions can be found in reference Sambrook, et al. (cited above).

Example 1

Identification of Nucleotide Sequence of the Protein Vitellogenin of *Anthonomus grandis* for Preparing the dsRNA Eggs, larvae and adult insects of *A. grandis* were obtained from the Laboratório de bioecologia e semioquímicos de insetos da Embrapa Recursos Genéticos e Biotecnologia em Brasília-DF (Laboratory of bioecology and semiochemicals of insects of the EMBRAPA Genetic Resources and Biotechnology in Brasília-DF) R. The colony is fed with an artificial diet as described in by Oliveira et al (2011) and kept at 26±2° C., relative unit of 60±10% and 12-hour photoperiod. For cloning and sequencing vitellogenin of *A. grandis*, the total RNA was isolated from adult insects using Trizol (Invitrogen), following the protocol indicated by the maker The cDNA was synthesized from □□g of total RNA using the kit Superscript II™ First-Strand Synthesis System for RT-PCR (Invitrogen) using oligo d(T)-AP. For initial amplification of the gene fragment of vitellogenin of *A. grandis*, one used specific primers, vit F (SEQ ID NO 12)-e VitR SEQ ID NO 13) taking as a reference the vitellogenin sequence deposited at the public databank NCBI (access code: M72980.1). One carried out a PCR step using specific primers for cloning the gen fragment. The PCR reactions were carried out by using the following conditions: 94° C. for 1 min, annealing temperature and 55° C. and extension at 72° C. for 1 minute per 30 cycles. The design of the double-stranded RNA segment consisting in choosing a fragment of 400 pb (SEQ ID NO 2), using, as a mold, the sequence of the cDNA of Vitellogenin. One used the program BLOCK-iT™ RNAi Designer (available on rnaidesignerinvitrogen.com/rnaiexpress), which analyzes the sequences and indicates regions of greater possibility for use in gene silencing.

The double-stranded RNAs were synthesized from products of the PCRs flanked by the minimum sequence of the promoter T7 (SEQ ID NO 18). The products of the PCRs were cloned and sequenced. After confirmation of the sequence, the synthesis of dsRNA was carried out using 0.5 µg of product of PCR as a mold for the transcription reaction volume of 20 µL, as described in the protocol of the manual of the kit MEGAscript® T7 High Yield (Ambion). The reaction was incubated for 16 hs at 37° C., followed by treatment with DNAse I RNase-free (Ambion, Invitrogen) for 15 minutes. For alignment of the double-stranded RNA, the reaction products were incubated at 70° C. for 5 minutes and cooled at room temperature (22° C.). for purification of the products from the transcription, one followed an extraction with phenol/chloroform and then precipitation with isopropyl alcohol, according to protocol described by the maker of the product (Ambion). The dsRNA was dissolved in water treated with DEPC, and the quantification was obtained by spectrophotometry.

Example 2

Bioassays of Microinjection of dsRNA in *Anthonomus grandis*

Samples of double-stranded RNA (dsRNA) were carried out in bioassays against cotton-boll weevil. The dsRNA was prepared from sequences identified as described in example 1. For the microinjection bioassays, the dsRNA molecules in all the treatments were injected into the dorsal abdominal region of adult females with up to 24 hours' emergency 24. In order to carry out this procedure, it was necessary to raise one of the elytra so as to expose the microinjection site. After the injection, the females were kept under standard feeding conditions on artificial diet, and couples were formed to enable copulation.

In order to evaluate the effect of the dsRNA on the expression of the target transcript, one used the PCR technique in real time and the reference genes: GAPDH and beta-Actina. In the microinjection assays aiming at the effect of silencing the vitellogenin, one evaluated a few variables as described hereinafter: 1—persistence of the gene silencing for 5 days after microinjection; 2—effect of the gene silencing on the oviposition of females of *A. grandis;* 3—effect of the gene silencing on the viability of the eggs of the insect.

Each experimental unit consisted of 15 microinjected adult females and 10 non-microinjected adult males the experimental period was of 15 days. The bioassay consisted of three biological replicas with three technical replicas. The control treatment consisted in applying dsRNA of a non-related gene, in this case one used the dsRNA with sequence of the gene of Beta-glucuronidade (GUS) of *Escherichia coli*, and microinjection of water treated with DEPC (diethylpyrocarbonate) as technical control. In order to analyze the data obtained in the bioassays, one applied a variance analysis, followed by the multiple comparison test of Turkey, at the level of 5% significance. The results of the bioassay of the microinjection of dsRNA for Vitellogenin exhibited an effect that culminated in infertility of females in comparison with the controls, as described hereinafter.

Example 3

Results of the Bioassays of Microinjection of dsRNA and Evaluation of Gene Silencing for the Protein Vitellogenin on *A. grandis*

One identified the sequence fragment of cDNA of the gene of the Vitellogenin of *A. grandis*, the size of which was of 400 nucleotides (SEQ ID NO 2), which served as a mold for the synthesis of dsRNA molecules, as described in example 1. One verified, by means of the microinjection bioassays and by the results of the PCT analysis in real time that the dsRNA molecules were capable of reducing the number of transcripts of Vitellogenin (FIG. 1). Also by PCR analyses in real time, one observed that in adult insects, microinjections of de 500 ng of dsRNA were sufficient for causing, after 72 hours, a drastic reduction of the number of transcripts (FIG. 1).

Figure 2:
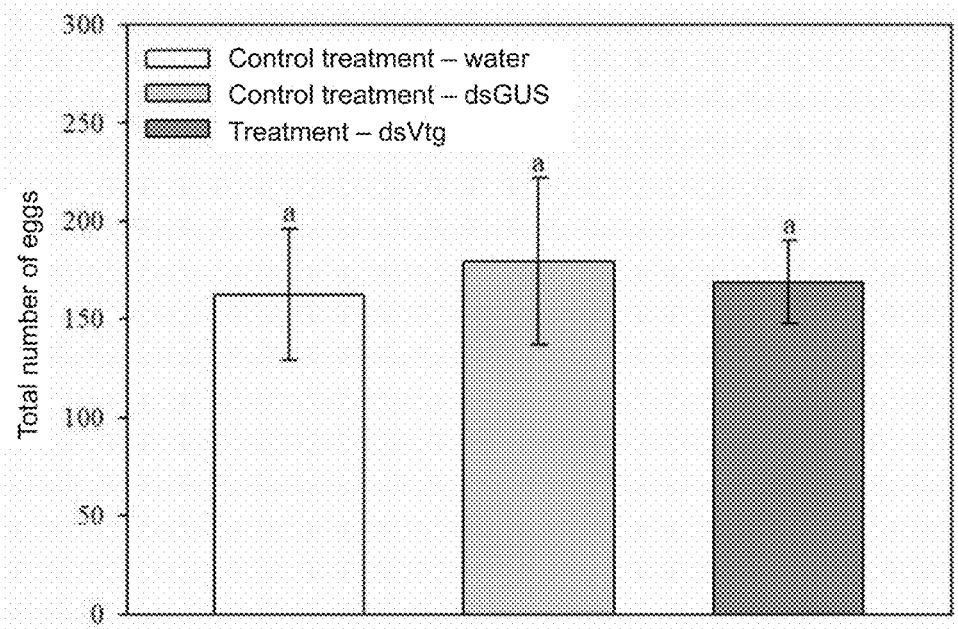
FIG. 2: Mean of the total number of eggs laid by the females of *A. grandis* from the treatments of microinjection with doped H2O, dsRNA of GUS and dsRNA of Vitellogenin for 15 days from the bioassay.
Figure 3:
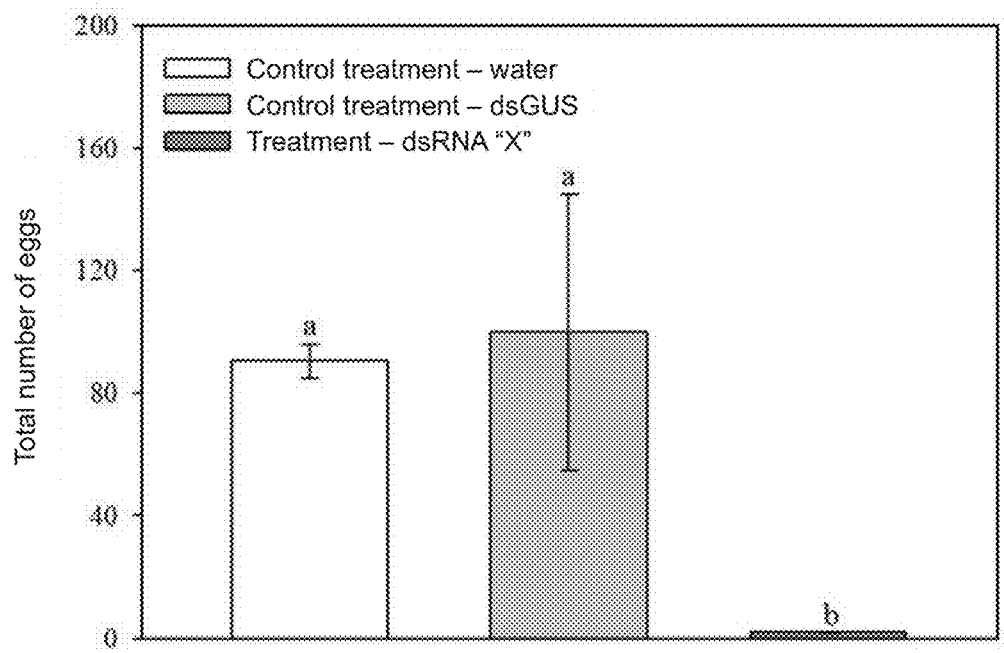
FIG. 3: Mean of the total number of larvae enclosed from the eggs laid by the females of *A. grandis* from the treatments of microinjection with doped H2O, dsRNA of GUS and dsRNA of Vitellogenin for 15 days from the bioassay.
Figure 4:
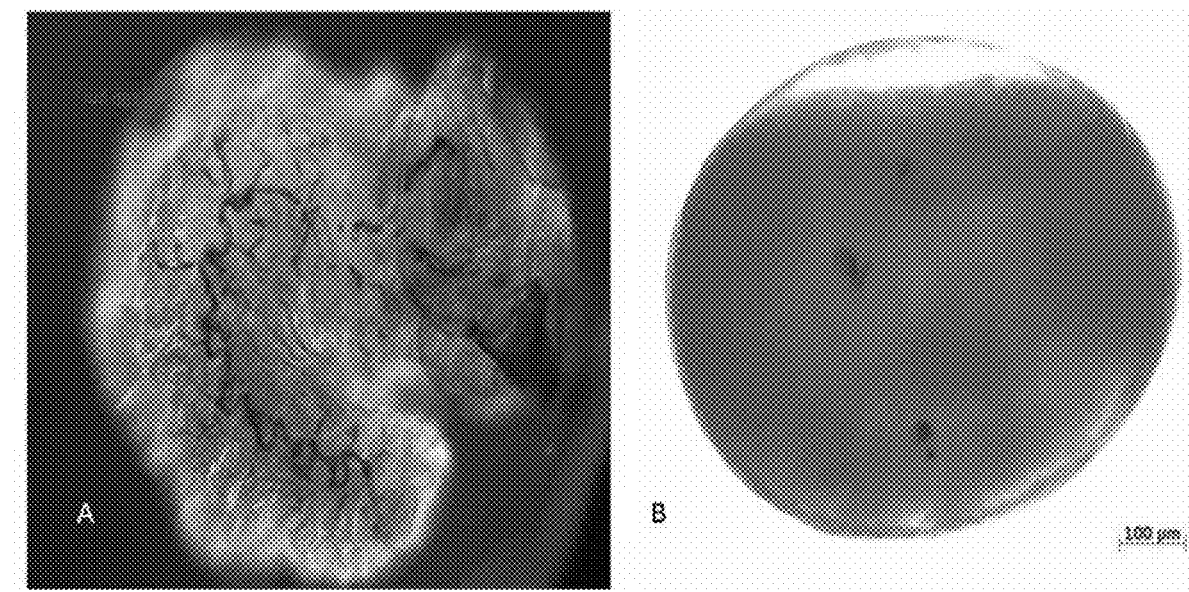
FIG. 4: Larvae/eggs of *A. grandis* 96 hours after oviposition by females microinjected with doped H2O, dsRNA of GUS and dsRNA of Vitellogenin. (A) is larva enclosed 96 hours after oviposition by microinjected female from the control treatment showing a development typical to this time, characteristic of the eggs from the control treatments; and (B) is egg with development aborted after 96 hours from oviposition, demonstrating interruption in the development of the embryo.

In the evaluation of phenotypical parameters caused by microinjection of the dsRNA of Vitellogenin, one verified that the females were capable of carrying out oviposition in the same way as the females from the control treatments (FIG. 2). However 99% of the eggs were completely inviable (FIG. 3). Besides, microscopy studies confirmed the blockage of the development of the embryo inside the eggs, which explains this low viability (FIG. 4, Attachment 1).

Example 4

Development of the Gene Construct for Expression of dsRNAs in Cotton Plant (pBSK-AdsVitCHS)

For the present invention, aiming at the effect of silencing the genes of chitin synthase 2 (SEQ ID NO 16) an vitellogenin (SEQ ID NO 17) in controlling cotton-boll weevil, one synthesized a gene construct for expression of target genes in genetically modified cotton-plant (FIG. 7, SEQ ID NO 7), containing the following sequences Ahas for expression of Imazapyr (marker for selection of the genetically modified plants), under regulation of the sequences of the promoter and terminator of the gene Ahas); promotor UCEA1.7 (PI 0701230-6, SEQ ID No 9); of the specific sense sequence for expression of dsRNA of Chitin Synthase 2 of cotton weevil (SEQ ID NO 1, BR 10 2012 033539-5); specific sense sequence for expression of dsRNA of Vitellogenin of cotton-boll weevil (SEQ ID NO 2), intron (SEQ ID No 11), specific antisense sequence for expression of dsRNA of Chitin Synthase 2 of cotton weevil (SEQ ID NO 3, BR 10 2012 033539-5); specific antisense sequence for expression of dsRNA of Vitellogenin of cotton weevil (SEQ ID NO 4) and the terminator of Nopalina sintase (tNOS—Depicker et al, 1982 (Depicker A, Stachel S, Dhaese P, Zambryski P, Goodman H M. (1982) Nopaline synthase: transcript mapping and DNA sequence. J. Mol. Appl. Genet. 1: 561-573).

The gene construct has, in its skeleton, the sequence of the plasmid pBSK containing the gene bla, which encodes beta lactamase, the most widely used marker in molecular biology for resistance to Ampicilina (selection of genetically transformed bacteria). Said construct (pBSK-AdsVitCHS) has the following arrangement of parts in the SEQ ID NO 7: Cassette Ahas: promoter AHAS+gene ahas+terminator ahas (674-6375 pb of SEQ ID NO 7), Promoter UCEA1.7 (6381-7392 pb of SEQ ID NO 7), Fragment of the gene of Vitellogenin in the sense orientation (7393-7569 pb of SEQ ID NO 7), Fragment of the gene of Chitin Synthase 2 in the sense orientation (7570-7754 pb of SEQ ID NO 7), intron Pdk (7755-8496 pb of the SEQ ID NO 7), Fragment of the gene of Chitin Synthase 2 in the reverse complementary orientation (8535-8681 pb of SEQ ID NO 7), Fragment of the gene of Vitellogenin in the reverse complementary orientation (8682-8858 pb of SEQ ID NO 7), Terminator-NOS (8859-9115 pb of SEQ ID NO 7), pBluescript II (1-673 pb of SEQ ID NO 7) and (9116-11340 pb of SEQ ID NO 7).

The gene construct pBSK-AdsVitCHS described above (FIG. 7, SEQ ID NO 7) was inserted into cotton plants through bioballistics for obtaining the genetically modified cotton plants, to impart resistance to cotton weevil.

Example 5

Development of the Gene Construction for Expression of dsRNAs in Conjunction with the Gene for the Toxin Cry8Ka5 in Cotton Plant (pBSK-AdsVitCHS-Cry8)

Figure 5:
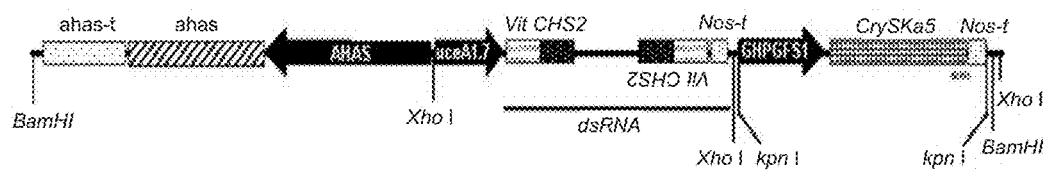
FIG. 5: A scheme representing the expression cassette of the gen construct pBSK-AdsVitCHS-Cry8 used for transforming cotton plant with a view to silencing target genes and suppressing expression of toxins Cry. The construct has the promoter, gene and terminator Ahas, promoter UCEA 1.7, dsRNA of chitin synthase 2 of cotton weevil, dsRNA of vitellogenin of cotton weevil, the promoter GHPGFS1 of expression in flower bud, isolated from *Arabidopsis*, the gene for toxin Cry8ka5 and the terminator of Nopalina Synthase (tNOS).

For the present invention, aiming at the effect of silencing the genes of chitin synthase 2 (SEQ ID NO 16) and vitellogenin (SEQ ID NO 17) and super expression of toxin Cry8ka5 (PI0906128-2, (SEQ ID No 5—Cry8ka5 and SEQ ID No 6—Cry8ka5_aa) in controlling cotton-boll weevil, one synthesized a gene construction for expression of target genes in genetically modified cotton plants (FIG. 5, SEQ ID NO 8), containing the following sequences: gene Ahas for expression of Imazapyr (marker for selection of the genetically modified plants) under regulation of the sequences of the promoter and terminator of the gene Ahas); promoter UCEA1.7 (PI 0701230-6); of the specific sense sequence for expression of dsRNA of Chitin Synthase 2 of cotton weevil (SEQ ID NO 1, BR 10 2012 033539-5); specific sense sequence for expression of dsRNA of Vitelfogenin of cotton weevil (SEQ ID NO 2), intron (SEQ ID No 11), specific antisense sequence for expression of dsRNA of Chitin Synthase 2 of cotton weevil (SEQ ID NO 3, BR 10 2012 033539-5); specific antisense sequence for expression of dsRNA of Vitellogenin of cotton weevil (SEQ ID NO 4), promoter GHPGFS1, isolated from plants of *Arabidopsis* (BR 10 2012 015993-7, SEQ ID No 10), used for directing the expression of the toxin Cry8ka5 for the blower bud and the terminator of Nopalina synthase (tNOS—Depicker et al, 1982 (Depicker A, Stachel S, Dhaese P, Zambryski P, Goodman H M. (1982) Nopaline synthase: transcript mapping and DNA sequence. J. Mol. Appl. Genet. 1: 561-573). The gene construct has, in its skeleton, the sequence of the plasmid pBSK containing the gene bla, which encodes beta lactamase, the most widely used marker in molecular biology for resistance to Ampicilina (selection of genetically transformed bacteria). Said construct (pBSK-AdsVitCHS-Cry8) has the following arrangement of parts in SEQ ID NO 8: Cassete Ahas: promoter AHAS+gene ahas+terminator ahas (674-6375 pb of SEQ ID NO 8), Promoter UCEA1.7 (6381-7392 pb of SEQ ID NO 8), Fragment of the gene of Vitellogenin in the sense orientation (7393-7569 pb of SEQ ID NO 8), Fragment of the gene of Chitin synthase 2 in the sense orientation (7570-7754 pb of SEQ ID NO 8), intron Pdk (7755-8496 pb of SEQ ID NO 8), Fragment of the gene of Chitin synthase 2 in the reverse complementary orientation (8535-8681 pb of SEQ ID NO 8), Fragment of the gene of Vitellogenin in the reverse complementary orientation (8682-8858 pb of SEQ ID NO 8), Terminator-NOS (8859-9115 pb of SEQ ID NO 8), Promoter GhPGFS (9127-9893 pb of SEQ ID NO 8), Cry8ka5+TagHis (9905-11870 pb of SEQ ID NO 8), terminator-NOS (11871-12130 pb of SEQ ID NO 8), pBluescript II (1-673 pb of SEQ ID NO 8) and (12131-14364 pb of SEQ ID NO 8).

The gene construct pBSK-AdsVitCHS-Cry8 described above (FIG. 5, SEQ ID NO 8) was inserted into cotton plants through biolistics for obtaining the genetically modified cotton plants, to impart resistance to cotton weevil.

Example 6

Development of the Gene Construct for Expression of dsRNA of Chitin Synthase in Conjunction with the Gene for the Toxin Cry8Ka5 in Cotton Plant pBSK-AdsCHS-Cry8

Figure 8:
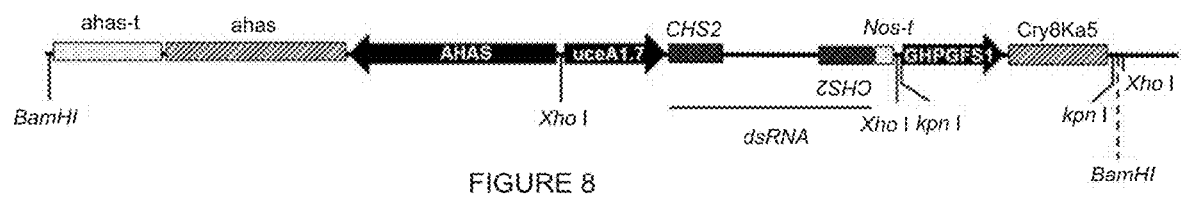
FIG. 8: A scheme representative of the expression cassette of the gene construct pBSK-AdsCHS-Cry8 used for transforming cotton plants with a view to silencing the target gene and suppressing the expression of toxins Cry. The construct has the promotor, gene and terminator Ahas, promotor UCEA 1.7, dsRNA of chitin synthase 2 of cotton weevil, the promoter GHPGFS1 of expression in flower bud, isolated from *Arabidopsis*, the gent for toxin Cry8ka5 and the terminator of Nopalina Synthase (tNOS).

For the present invention, aiming at silencing the genes of the chitin synthase 2 (SEQ ID NO 16) and superexpression of toxin Cry8ka5 (PI0906128-2, SEQ ID No 5—Cry8ka5 and SEQ ID No 6—Cry8ka5_aa) in controlling cotton-boll weevil, one synthesized a gene construct for expression of target genes in genetically modified cotton plants (FIG. 8, SEQ ID NO 19), containing the following sequences: gene Ahas for expression of Imazapyr (marker for selection of the genetically modified plants) under regulation of the sequences of the promoter and terminator of the gene Ahas); promoter UCEA1.7 (PI 0701230-6); of the specific sense sequence for expression of dsRNA of Chitin Synthase 2 of cotton weevil (SEQ ID NO 1, BR 10 2012 033539-5); intron (SEQ ID No 11), specific antisense sequence for expression of dsRNA of Chitin Synthase 2 of cotton weevil (SEQ ID NO 3, BR 10 2012 033539-5); promoter GHPGFS1, isolated from plants of *Arabidopsis* (BR 10 2012 015993-7, SEQ ID No 10), used for directing the expression of the toxin Cry8ka5 for the flower bud and the terminator of Nopalina sintase (tNOS—Depicker et al, 1982 (Depicker A, Stachel S, Dhaese P, Zambryski P, Goodman H M. (1982) Nopaline synthase: transcript mapping and DNA sequence, J. Mol. Appl. Genet. 1: 561-573). The gene construction has, in its skeleton, the sequence of the plasmid pBSK containing the gene bla, which encodes beta lactamase, the most widely used marker in molecular biology for resistance to Ampicilina (selection of genetically transformed bacteria). Said construct (pBSK-AdsCHS-Cry8) has the following arrangement of parts in the SEQ ID NO 19: Cassette Ahas: promoter AHAS+gene ahas+terminator ahas (639-6375 pb of SEQ ID NO 19), Promoter UCEA1.7 (6381-7392 pb of SEQ ID NO 19), Fragment of the gene of Chitin synthase 2 in the sense orientation (7358-7542 pb of SEQ ID NO 19), intron Pdk (7543-8284 pb of SEQ ID NO 19), Fragment of the gene of Chitin synthase 2 in the reverse complementary orientation (8285-8469 pb of SEQ ID NO 19), Terminator-NOS (8470-8726 pb of SEQ ID NO 19), Promoter GhPGFS (8738-9504 pb of SEQ ID NO 19), Cry8ka5+TagHis (9511-11480 pb of SEQ ID NO 19), terminator-NOS (11484-11740 pb of SEQ ID NO 19), pBluescript II (1-632 pb of SEQ ID NO 19) and (11741-13954 pb of SEQ ID NO 19).

The gene construct pBSK-AdsCHS-Cry8 described above (FIG. 8, SEQ ID NO 19) was inserted into cotton plants through bioballistics for obtaining the genetically modified cotton plants, to impart resistance to cotton weevil.

Example 7

Development of the Gene Construct for Expression of dsRNA of Vitellogenin in Conjunction of the Gene for the Toxin Cry8Ka5 in Cotton Plant pBSK-AdsVit-Cry8

Figure 9:
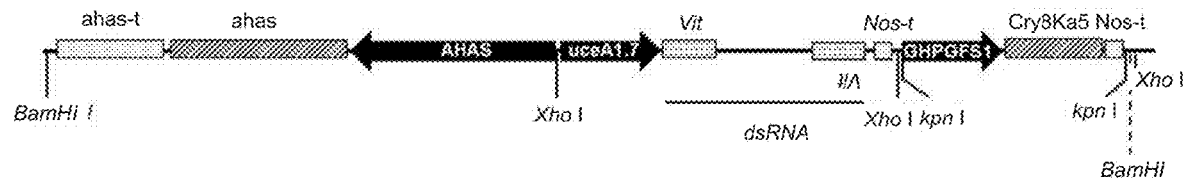
FIG. 9: A scheme representative of the expression cassette of the gene construct pBSK-AdsVit-Cry8 used for transforming cotton plants with a view to silencing target genes and suppressing the expression of toxins Cry. The construct has the promoter, gene and terminator Ahas, promoter UCEA 1.7, dsRNA of vitellogenin of cotton weevil, the promoter GHPGFS1 of expression in flower bud, isolated from *Arabidopsis*, the gene for toxin Cry8ka5 and the terminator of Nopalina Synthase (tNOS).

For the present invention, aiming at the effect of silencing the gene of vitellogenin (SEQ ID NO 17) and superexpression of the toxin Cry8ka5 (PI0906128-2, SEQ ID No 5—Cry8ka5 and SEQ ID No 6—Cry8ka5_aa) in controlling cotton-boll weevil, one synthesized a gene construct for expression of target genes in genetically modified cotton plants (FIG. 9, SEQ ID NO 20), containing the following sequences: gene Ahas for expression of Imazapyr (marker for selection of the genetically modified plants) under regulation of the sequences of the promoter and terminator of the gene Ahas); promoter UCEA1.7 (PI 0701230-6); specific sense sequence for expression of dsRNA of Vitellogenin of cotton weevil (SEQ ID NO 2), intron (SEQ ID No 11), specific antisense sequence for expression of dsRNA de Vitellogenin of cotton weevil (SEQ ID NO 4), promoter GHPGFS1, isolated from plants of *Arabidopsis* (BR 10 2012 015993-7, SEQ ID No 10), used for directing the expression of the toxin Cry8ka5 for the flower bud and the terminator of Nopalina synthase (tNOS—Depicker et al, 1982 (Depicker A, Stachel S, Dhaese P, Zambryski P, Goodman H M. (1982) Nopaline synthase: transcript mapping and DNA sequence. J. Mol. Appl. Genet. 1: 561-573). The gene construct has, in its skeleton, the sequence of the plasmid pBSK containing the gene bla, which encodes beta lactamase, the most widely used marker in molecular biology for resistance to Ampicilina (selection of genetically transformed bacteria). Said construct (pBSK-AdsVit-Cry8) has the following arrangement of parts in the SEQ ID NO 20: Cassette Ahas: promoter AHAS+gene ahas+terminator ahas (639-6340 pb of SEQ ID NO 20), Promoter UCEA1.7 (6347-7357 pb of SEQ ID NO 20), Fragment of the gene of Vitellogenin in the sense orientation (7358-7534 pb of SEQ ID NO 20), intron Pdk (7535-8276 pb of SEQ ID NO 20), Fragment for the gene of vitellogenin in the reverse complementary sequence (8277-8453 pb of SEQ ID NO 20), Terminator-NOS (8454-8710 pb of SEQ ID NO 20), Promotor GhPGFS (8724-9488 pb of SEQ ID NO 20), Cry8ka5+TagHis (9494-11470 pb of SEQ ID NO 20), terminator-NOS (11471-11720 pb of SEQ ID NO 20), pBluescript II (1-632 pb of SEQ ID NO 20) and (11721-13938 pb of SEQ ID NO 20).

The gene construct pBSK-AdsVit-Cry8 described above (FIG. 9, SEQ ID NO 20) was inserted into cotton plants through bioballistic for obtaining the genetically modified cotton plants, to impart resistance to cotton weevil.

Example 8

Insertion of the Gene Constructs into Cotton Plants

Figure 6:
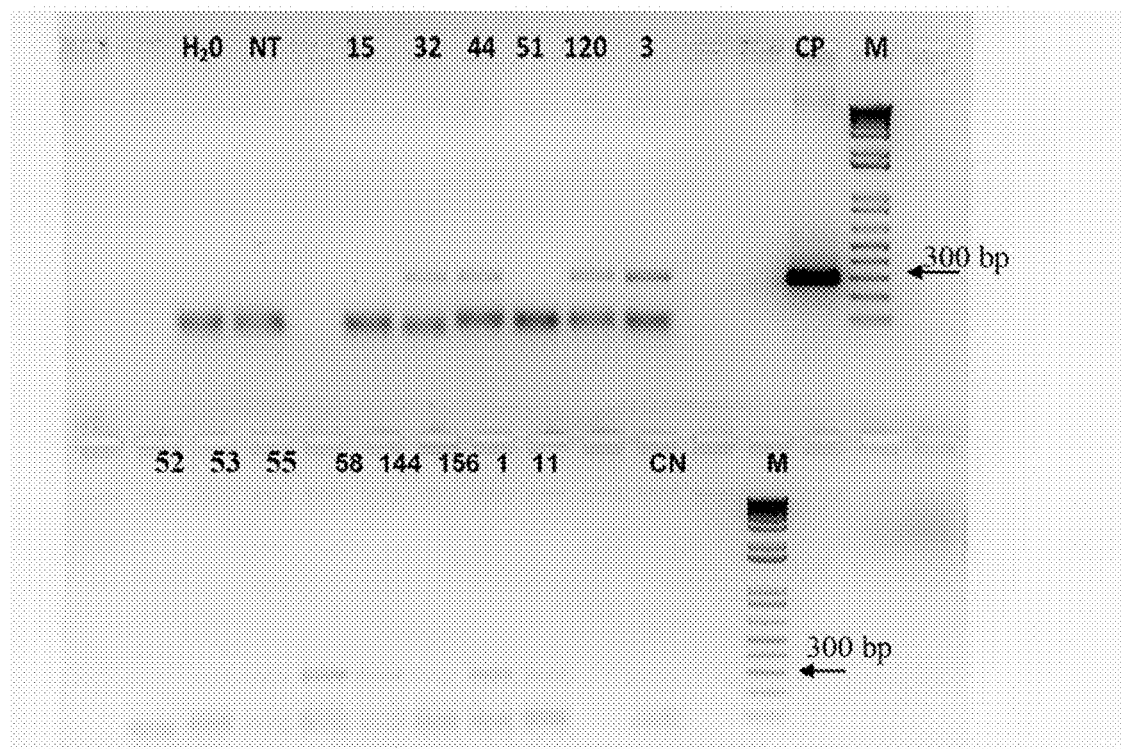
FIG. 6: Analysis of the product of PCR using genic DNA of cotton plant genetically transformed with the construct pBSK-AdsVitCHS-Cry8. The Numbers indicate various plants T0, CP (positive control, DNA plasmidial); CN (negative control, only the reaction mixture without addition of DNA). The arrow indicates amplicon of 300 bp representing the amplification with oligos for the dsRNA (CHS2 and Vit).
Figure 7:
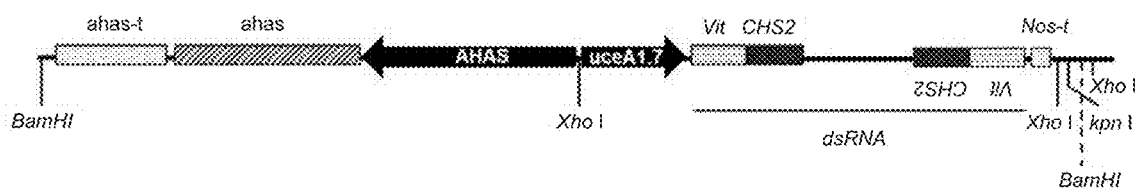
FIG. 7: A scheme representative of the expression cassette of the gene construction pBSK-AdsVitCHS used for transforming cotton plants with a view to silencing target genes. The construct has the promoter, gene and terminator Ahas, promoter UCEA 1.7, dsRNA of chitin synthase 2 of cotton weevil, dsRNA of vitellogenin of cotton weevil and the terminator of Nopalina Synthase (tNOS).

The plasmidial DNA of the gene construct described in example 5 was digested with the restriction enzyme BamH I and the fragment comprising the expression cassette containing the genes for Ahas, Cry8ka5 and dsRNA for Chitin Synthase 2 and vitellogenin, was analyzed in 1% agarose gel electrophoresis. After separation of the fragment of 11.460 pb was eluted from the gel by electric field. FIG. 6 indicates the presence of the construct pBSK-AdsVitCHS-Cry8 through amplification with the oligos CHS2 and Vit (SEQ ID NO 14 and SEQ ID NO 15, respectively) generating a fragment of 300 pb. Alternatively the plasmidial DNA of the gene construct described in example 4 was digested with restriction enzyme BamH I and enzyme Kpn I and the fragment comprising the expression cassette containing the genes for Ahas, dsRNA for Chitin Synthase 2 and vitellogenin, was analyzed in 1% agarose gel electrophoresis. After separation the fragment of 8442 pb was eluted from the gel by electric filed. FIG. 7 indicates the scheme illustrating the construct pBSK-AdsVitCHS. The product of the elution was quantified and the DNAs used separately in the gene transformation methodology via bioballistics, according to the protocol developed at the Embrapa Recursos Genéticos e Biotecnologia por Rech et al., 2008 (RECH E. L.; VIANNA, G. R. & ARAGAO, F. J. L. (2008). High-efficiency transformation by biolistics of soybean, common bean and cotton transgenic plants. Nature Protocols, 3: 410-418). The varieties of cotton used for the transformation protocol were Coker 310 and varieties of the Embrapa. The in vitro selection of transformants was carried out with the herbicidal Imazapir and the acclimatized plants cultivates in greenhouse for molecular characterization of the progenies.

The invention claimed is:

1. A gene construct comprising:
   (i) a promoter sequence functional in a plant;
   (ii) a first sense fragment comprising a nucleotide sequence having 95% or higher sequence identity to at least 23 contiguous nucleotides of SEQ ID NO: 1;
   (iii) a second sense fragment comprising a nucleotide sequence having 95% or higher sequence identity to at least 23 contiguous nucleotides of SEQ ID NO: 2;
   (iv) a spacer sequence;
   (v) a first antisense fragment comprising a nucleotide sequence entirely complementary to said nucleotide sequence in said first sense fragment;
   (vi) a second antisense fragment comprising a nucleotide sequence entirely complementary to said nucleotide sequence in said second sense fragment; and
   (vii) a terminator sequence functional in a plant,
   wherein said gene construct encodes a double-stranded ribonucleotide sequence that, upon ingestion by *Anthonornus grandis*, inhibits or reduces the proliferation of said *Anthonomus grandis*.

2. A gene construct comprising:
   (i) a promoter sequence functional in a plant;
   (ii) a first sense fragment comprising a nucleotide sequence having 95% or higher sequence identity to at least 23 contiguous nucleotides of SEQ ID NO: 1;
   (iii) a second sense fragment comprising a nucleotide sequence having 95% or higher sequence identity to at least 23 contiguous nucleotides of SEQ ID NO: 2;
   (iv) a spacer sequence;
   (v) a first antisense fragment comprising a nucleotide sequence entirely complementary to said nucleotide sequence in said first sense fragment;
   (vi) a second antisense fragment comprising a nucleotide sequence entirely complementary to said nucleotide sequence in said second sense fragment;
   (vii) a terminator functional in a plant; and wherein the construct further comprises
   (viii) a further promoter sequence functional in a plant;
   (ix) a nucleotide sequence having 95% or higher sequence identity to the nucleotide sequence of SEQ ID NO: 5; and
   (x) a further terminator sequence functional in a plant,
   wherein said gene construct encodes a double-stranded ribonucleotide sequence that, upon ingestion by *Anthonornus grandis*, inhibits or reduces the proliferation of said *Anthonomus grandis*.

3. A gene construct comprising:
   (i) a promoter sequence functional in a plant;
   (ii) a sense fragment comprising a nucleotide sequence having 95% or higher sequence identity to at least 23 contiguous nucleotides of SEQ ID NO: 2;

(iii) a spacer sequence;
(iv) an antisense fragment comprising a nucleotide sequence entirely complementary to said nucleotide sequence in said sense fragment;
(v) a terminator sequence functional in a plant; and wherein the construct further comprises
(vi) a further promoter sequence functional in a plant;
(vii) a nucleotide sequence having 95% or higher sequence identity to the nucleotide sequence of SEQ ID NO: 5; and
(viii) a further terminator sequence functional in a plant, wherein said gene construct encodes a double-stranded ribonucleotide sequence that, upon ingestion by *Anthonornus grandis*, inhibits or reduces the proliferation of said *Anthonomus grandis*.

4. The gene construct according to claim 1, wherein said promoter sequence comprises a nucleotide sequence having at least 95% sequence identity to the nucleotide sequence of SEQ ID NO: 9 or SEQ ID NO: 10.

5. The gene construct according to claim 1, wherein the spacer sequence is an intron.

6. The gene construct according to claim 5, wherein the intron is selected from the group consisting of intron pdk, intron catalase of castor, intron Delta 12 desnaturase of cotton plant, Delta 12 desnaturase of *Arabidopsis*, intron ubiquitin of maize, intron of SV40, and intron of the malate synthase.

7. The gene construct according to claim 6, wherein the intron comprises a nucleotide sequence having at least 95% sequence identity to the nucleotide sequence of SEQ ID NO: 11.

8. The gene construct according to claim 1, wherein said construct comprises a nucleotide sequence having at least 95% sequence identity to the nucleotide sequence of SEQ ID NO: 7.

9. The gene construct according to claim 2, wherein said construct comprises a nucleotide sequence having at least 95% sequence identity to the nucleotide sequence of SEQ ID NO: 8.

10. The gene construct according to claim 3, wherein said construct comprises a nucleotide sequence having at least 95% sequence identity to the nucleotide sequence of SEQ ID NO: 20.

11. A vector comprising the gene construct of claim 1.

12. A transformed cell comprising the gene construct according to claim 1.

13. The cell according to claim 12, wherein said cell is a prokaryote cell.

14. The cell according to claim 12, wherein said cell is a eukaryote cell.

15. The cell according to claim 12, wherein said cell is a plant cell or a bacterial cell.

16. A transformed plant comprising the gene construct according to claim 1.

17. The plant according to claim 16, wherein in said plant, said gene construct is expressed in a cell of said plant, in the form of a double-stranded ribonucleotide sequence, and wherein upon ingestion by a pest insect, said double-stranded ribonucleic sequence inhibits or reduces the proliferation of said pest insect, wherein said pest insect is *Anthonomus grandis*.

18. A transformed plant comprising the gene construct according to claim 2.

19. A product produced by the plant according to claim 16, wherein said product comprises a detectable amount of the gene construct, or of a ribonucleotide or of a protein expressed therefrom.

20. A method for producing transgenic plants capable of producing dsRNA of interest, comprising the steps of:

providing a gene construct according to claim 1;

delivering said gene construct to a plant cell or plant cells, to produce a transgenic plant cell or plant cells; and growing or regenerating a transgenic plant from the transgenic cell or cells.

21. A method for controlling a pest insect, comprising making available, to a pest insect for ingestion, an agent comprising a double-stranded ribonucleotide sequence expressed from the gene construct according to claim 1, wherein said pest insect is *Anthonomus grandis*.

22. A method for controlling a pest insect, comprising making available, to a pest insect for ingestion, an agent comprising a double-stranded ribonucleotide sequence expressed from the gene construct according to claim 2, wherein said pest insect is *Anthonomus grandis*.

23. The method according to claim 21, wherein said double-stranded ribonucleotide sequence, upon being ingested by said pest insect, suppresses or reduces the expression of a gene that performs a function essential to the survival of the pest insect.

24. The method according to claim 23, wherein the function essential to the survival of the insect is selected from the group consisting of cellular apoptosis, differentiation and cellular development, egg formation, larval maturation, larval stage transition, pupation, cell division, energetic metabolism, respiration and formation and hardening of the cuticle.

25. A method for improving the yield of cultivated plants, subject to infestation by *Anthonomus grandis*, said method comprising the steps of:

obtaining a transgenic plant, by introducing a gene construct according to claim 1 into a plant; and growing said transgenic plant, whereby said transgenic plant expresses said gene construct, and wherein a double-stranded ribonucleotide sequence expressed from said gene construct can reduce or suppress the population of *Anthonomus grandis*.

26. The method according to claim 25, wherein the expression of the sense and antisense sequences of said gene construct produce RNA molecules that suppress a first and a second target gene in *Anthonomus grandis* upon ingestion of a portion of said plant, wherein said target genes perform a function essential to the survival of *Anthonomus grandis* that is selected from the group consisting of cellular apoptosis, differentiation and cellular development, egg formation, larval maturation, larval stage transition, pupation, cell division, energetic metabolism, respiration and formation and hardening of the cuticle.

27. A method for producing a product that reduces or suppresses a pest insect when ingested by said pest insect, wherein said method comprises obtaining the plant of claim 16, or a part thereof, and producing a processed product therefrom, wherein said pest insect is *Anthonomus grandis*.

28. A method for producing food or feed, wherein said method comprises obtaining the plant of claim 16, or a part thereof, and preparing food or feed from said plant or a part thereof.

29. A method of producing a plant resistant to *Anthonomus grandis*, said method comprising:

a. crossing a plant comprising a nucleic acid molecule comprising a nucleotide sequence having at least 95% sequence identity to a nucleotide sequence selected from the group consisting of SEQ ID NOs: 7 and 8 with a second plant;

b. obtaining seed from the crossing of step (a);

c. obtaining a DNA sample of the embryo of the seed; and d. detecting the presence of, in the DNA sample, a nucleic acid molecule comprising a nucleotide sequence having at least 95% sequence identity to a nucleotide sequence selected from the group consisting of SEQ ID NOs: 7 and 8, wherein the presence thereof indicates that the seed is capable of producing a plant resistant to *Anthonomus grandis*.

30. A method for growing a plant, comprising the following steps:

a. providing a seed or seedling comprising a nucleic acid molecule comprising a nucleotide sequence having at least 95% sequence identity to a nucleotide sequence selected from the group consisting of SEQ ID NOs: 7 and 8; and b. planting or sewing the material provided in step (a) in a substrate, soil or environment suitable for appropriate germination or sprouting, growth and development.

\* \* \* \* \*